(12) United States Patent
Alster et al.

(10) Patent No.: US 7,220,000 B2
(45) Date of Patent: May 22, 2007

(54) METHODS, DEVICES AND SYSTEMS FOR ASSESSING EYE DISEASE

(75) Inventors: Yair Alster, Tel Aviv (IL); Omer Rafaeli, Givatayim (IL); Barak Azmon, Tel Aviv (IL)

(73) Assignee: Notal Vision Inc., New Castle, DE (US)

( * ) Notice: Subject to any disclaimer, the term of this patent is extended or adjusted under 35 U.S.C. 154(b) by 621 days.

(21) Appl. No.: 10/368,002

(22) Filed: Feb. 19, 2003

(65) Prior Publication Data

US 2003/0223038 A1 Dec. 4, 2003

Related U.S. Application Data

(60) Provisional application No. 60/357,115, filed on Feb. 19, 2002.

(51) Int. Cl.
*A61B 3/02* (2006.01)

(52) U.S. Cl. ............... 351/224; 351/237; 351/239

(58) Field of Classification Search ............ 351/200, 351/222, 246, 239, 237, 224; 600/558
See application file for complete search history.

(56) References Cited

U.S. PATENT DOCUMENTS

| | | | | |
|---|---|---|---|---|
| 4,349,250 A | * | 9/1982 | Gelius | ............ 351/239 |
| 4,634,243 A | | 1/1987 | Massof et al. | |
| 4,798,456 A | | 1/1989 | Enoch et al. | |
| 4,822,162 A | | 4/1989 | Richardson et al. | |
| 4,995,717 A | | 2/1991 | Damato | |
| 5,061,060 A | | 10/1991 | Aulhorn et al. | |
| 5,412,561 A | | 5/1995 | Rosenshein et al. | |
| 5,463,431 A | | 10/1995 | Suzuki et al. | |
| 5,506,633 A | | 4/1996 | Sperling | |
| 5,539,482 A | * | 7/1996 | James et al. | ............ 351/246 |
| 5,565,949 A | * | 10/1996 | Kasha, Jr. | ............ 351/224 |
| 5,589,897 A | | 12/1996 | Sinclair et al. | |
| 5,864,384 A | * | 1/1999 | McClure et al. | ............ 351/224 |
| 5,883,692 A | * | 3/1999 | Agonis et al. | ............ 351/224 |
| 5,892,570 A | * | 4/1999 | Stevens | ............ 351/237 |
| 5,946,075 A | | 8/1999 | Horn | |

(Continued)

OTHER PUBLICATIONS

Jay M. Enoch et al., "Hyperacuity Perrimetry: Assessment of Macular Function Through Ocular Opacities" Arch Ophthalmol, vol. 112, Aug. 1984, pp. 1164-1168.

(Continued)

*Primary Examiner*—Ricky Mack
*Assistant Examiner*—Jerry Fang
(74) *Attorney, Agent, or Firm*—Daniel J. Swirsky; AlphaPatent Accociates Ltd.

(57) ABSTRACT

Methods and devices for detecting eye disease and for assessing the clinical stage of an eye disease in an individual. The methods include projecting test patterns onto the retina of a tested eye and subjecting the individual to a competing sensory stimuli. The competing stimuli may be of various different sensory modalities including visual, auditory, or other sensory modalities. If the individual perceives a difference in at least one localized part of the perceived image of a test pattern as compared to a predefined reference pattern, the individual provides a response indicative of the difference or differences. The responses are processed to assess the severity of eye disease if a disease is detected, or to determine the clinical stage of a detected eye disease.

64 Claims, 19 Drawing Sheets

U.S. PATENT DOCUMENTS

| | | | |
|---|---|---|---|
| 6,027,217 | A | 2/2000 | McClure et al. |
| 6,033,076 | A | 3/2000 | Braeuning et al. |
| 6,260,970 | B1 | 7/2001 | Horn |
| 6,406,437 | B1 | 6/2002 | Zur et al. |
| 6,513,931 | B1 | 2/2003 | Torrey et al. |
| 6,520,640 | B1 | 2/2003 | Binnun |
| 6,527,391 | B1 | 3/2003 | Heijl et al. |
| 6,572,229 | B2 | 6/2003 | Wei |
| 6,578,966 | B2 | 6/2003 | Fink et al. |
| 6,585,376 | B1 * | 7/2003 | Matsumoto ............. 351/239 |
| 6,688,746 | B2 | 2/2004 | Malov |
| 6,742,894 | B2 * | 6/2004 | Stewart ............. 351/237 |
| 2002/0042580 | A1 | 4/2002 | Alster et al. |

OTHER PUBLICATIONS

Michael Wall and Alfredo A. Saun, "Threshold Amsler Grid Testinng: Cross-Polarizing Lenses Enhance Yield", Arch Ophthalmol, vol. 104, Apr. 1986, pp. 520-523.

Stuart L. Fina and the Macular Photocoagulation Study Group, "Early Detection of Extrafoveal Neovascular Membranes by Daily Central Field Evaluation", Wilmer Ophthalmological Institute, John Hopkins University, Johns Hopkins University, presented at meeting which took place between Oct. 30-Nov. 3, 1984, pp. 603-609.

Vasudevan Lakshminarayanan et al., "Quantifications of Metamorphopsia Using Hyperaculty Techniques", Optometry and Vision Science, vol. 68, No. 12,, 1991, pp. 942-945.

Michael J. Tolentino et al., "Visual Field Deficits in Early Age-Related Macular Degeneration", Vision Res., vol. 34, No. 3, pp. 409-413, 1994.

Reginald G. Ariyasu et al., "Sensitivity, Specificity and Predictive Values of Screening Tests for Eye Conditions in a Clinic-Based Population", Ophthamology, vol. 103, No. 11, Nov. 1996, pp. 1751-1760.

Michael L. Slavin, "The Use of the Red Amsler Grid and Red-Green Lenses in Detecting Spurious Paracentral Visual Field Defects", American Journal of Opthalmology, vol. 103, No. 3, Part 1, Mar. 1987, pp. 338-339.

Michael Wall and Donald R. May, "Threshold Amsler Grid Testing in Maculopathies", Presented at the American Academy of Opthalmolgy Annual Meeting, New Orleans, Nov. 1986, pp. 1126-1133.

* cited by examiner

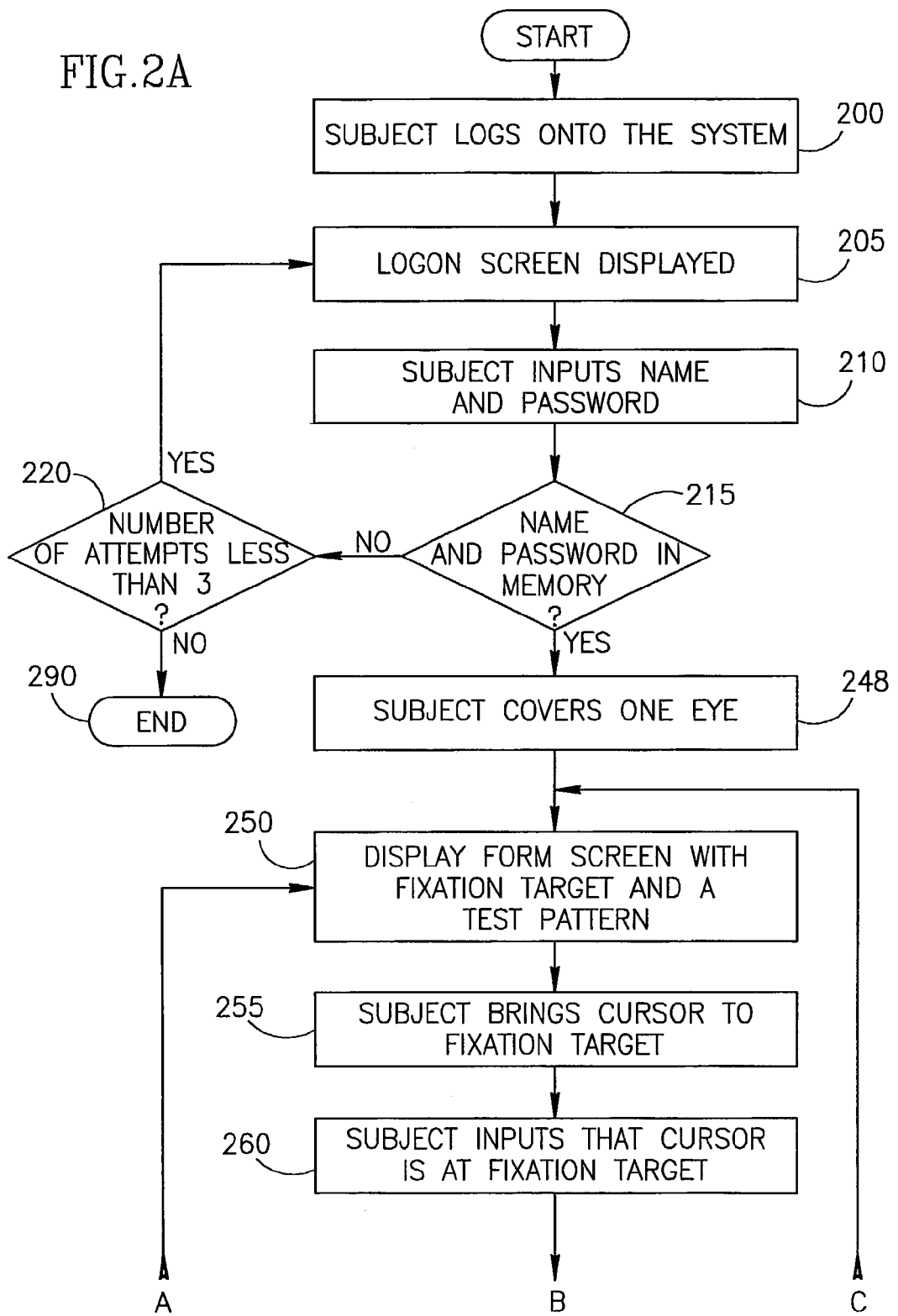

METHODS, DEVICES AND SYSTEMS FOR ASSESSING EYE DISEASE

RELATIONSHIP TO OTHER US APPLICATIONS

The present application claims priority from and the benefit of U.S. Provisional Patent Application Ser. No. 60/357,115 to Alster Yair et al., filed on Feb. 19, 2002 and entitled "METHODS, DEVICES AND SYSTEM FOR ASSESSING RETINAL LESIONS".

FIELD OF THE INVENTION

This invention generally relates to systems, devices, and methods for administering eye tests and for detecting, assessing, and classifying eye disease in patients.

BACKGROUND OF THE INVENTION

Age-related macular degeneration (AMD) is the leading cause of blindness among people over the age of 50 in the western world. It is a bilateral, although asymmetric disease, and comes in two forms. Dry or non-neovascular AMD is the more common and milder form of AMD, accounting for 85–90% of all AMD. The key identifier for dry AMD is small, round, white-yellow lesions (also known as Drusen) in the macula. Vision loss associated with dry AMD is far less dramatic than in the case of wet AMD. Recent publications indicate that dietary supplements including antioxidants and minerals reduce the progression of advanced AMD by 25% in patients with intermediate (non-vascular) AMD. It is estimated that as many as 14 million people suffer from dry AMD in the United States alone.

Wet AMD is less prevalent than the dry form, accounting for about 10–15% of AMD cases. The term "wet" denotes choroidal neovascularization (CNV), in which abnormal blood vessels develop beneath the retinal pigment epithelium (RPE) layer of the retina. Wet AMD is characterized by the development of choroidal angiogenesis which causes severe, and potentially rapid, visual deterioration. The visual distortion typically consists of perceiving straight lines as curved due to deformation of the retina in a region overlying the choroidal angiogenesis. The wet form of AMD accounts for about 60% of all cases of adult blindness in the United States. In the U.S. alone there are 200,000 new cases of wet AMD every year and a total of 1.7 million blind people from AMD.

Treatment modalities for wet AMD may include laser photocoagulation and Photodynamic therapy (PDT). Experimental treatments that are under current investigation include feeder vessel coagulation and trans-pupillary thermotherapy (TTT). All these proven or experimental therapies may halt or slow progression of the disease and will usually not improve visual function. Therefore, early detection is crucial to prevent severe visual loss.

Since approximately 12% of dry AMD cases develop wet AMD and subsequent blindness within 10 years, a patient diagnosed with dry AMD must be routinely examined by an ophthalmologist once or twice a year, depending on the severity of his condition. The patient is usually also given a so-called "Amsler grid" for weekly self-examination at home for symptoms of wet AMD. The patient is advised to consult an ophthalmologist immediately in the event that symptoms are noticed. The Amsler grid and its modifications (such as the "threshold Amsler" or the "red Amsler") have been shown to be poor detectors of early changes associated with wet AMD for several reasons. One reason is the phenomenon of "filling-in" whereby the brain fills in missing parts in the pattern or corrects defects or distortions in the pattern. The subject thus fails to perceive a distorted pattern as being distorted. Another problem with the Amsler grid is the inability of patients to adequately fixate their vision on a fixed point while taking the test. The Amsler test also suffers from low compliance stemming from the non-interactive nature of the test.

The degree of visual deterioration is a function of the size of the lesion and its proximity to the fovea at the time of diagnosis. Although most lesions probably start outside the foveal area, 70% of the lesions are already foveal and large (>1500 microns) at the time of diagnosis. It is therefore crucial to identify the lesions at the earliest possible stage, while they are still small and have not reached the fovea. It is known that 70% of lesions diagnosed as treatable become untreatable within less than three months, which indicates that the progression of the disease is relatively rapid. As many as 50% of patients with wet AMD are already ineligible for treatment when they first consult their ophthalmologist because the disease has progressed considerably. This is due to the poor validity of existing self-assessment methods for detecting an AMD-related lesion at an early stage, and the time lapsed between noticing the symptoms and seeing an ophthalmologist.

A reliable method for diagnosing wet AMD at the earliest possible stage, in conjunction with a referral system aimed at lowering the incidence of visual deterioration in this devastating disease, are imperative. If detected early, laser therapy to destroy the abnormal blood vessels may prevent additional vision loss. It is therefore crucial to detect the transition from dry to wet AMD as early as possible.

Furthermore, there is a long felt need for simple and inexpensive methods for classifying or assessing the stages of a visual disorder such as in patients with AMD.

SUMMARY OF THE INVENTION

There is therefore provided in accordance with an embodiment of the present invention a method for detecting eye disease in an individual the method includes the steps of:
  (a) projecting a first pattern on a first location on the retina of an eye of the individual;
  (b) fixating the individual's vision on a fixation target projected on the retina at or about the first location;
  (c) hiding at least a portion of the first pattern;
  (d) projecting a second pattern on a second location of the retina to allow the individual to form a perceived image of the second pattern;
  (e) receiving from the individual input indicative of a difference in at least one localized part of the perceived image as compared to a predefined reference pattern, if the individual detected a difference;
  (f) repeating steps (a) to (e) a number of times to obtain a plurality of data, wherein in at least some of the repetitions of steps (a) to (e), the individual is subjected to a competing sensory stimulus; and
  (g) processing the plurality of data to determine if the individual belongs to a group having a defined clinical stage of an eye disease.

Furthermore, in accordance with another embodiment of the present invention, the competing sensory stimulus is a sensory stimulus effective in modifying the ability of the individual to report a difference in at least one localized part of the perceived image as compared to a predefined reference pattern when the difference is perceived due to the eye disease.

Furthermore, in accordance with another embodiment of the present invention, steps (a) to (g) are performed in the order recited above.

Furthermore, in accordance with another embodiment of the present invention, the hiding is performed in response to the fixating.

Furthermore, in accordance with another embodiment of the present invention, the eye disease is selected from the group consisting of age-related macular degeneration, choroidal neovascularization, ocular hystoplasmosis, myopia, central serous retinopathy, central serous choroidopathy, glaucoma, diabetic retinopathy, media opacities, cataract, retinitis pigmentosa, optic neuritis, epiretinal membrane, vascular abnormalities, vascular occlusions, choroidal dystrophies, retinal dystrophies, macular hole, choroidal degeneration, retinal degeneration, lens abnormalities, and combinations thereof.

Furthermore, in accordance with another embodiment of the present invention, steps (a) to (e) are repeated while changing the position of at least one of the first pattern and the second pattern to map a selected region of the retina at a desired resolution.

Furthermore, in accordance with another embodiment of the present invention, steps (a) to (e) are repeated while changing the orientation of the first pattern and of the second pattern.

Furthermore, in accordance with another embodiment of the present invention, competing stimulus is selected from a competing stimulus presented before the projecting of the second pattern, a competing stimulus presented during at least part of the duration of projecting of the second pattern, a competing stimulus presented after the projecting of the second pattern and a competing stimulus which temporally overlaps at least a part of the duration of the projecting of the second pattern.

Furthermore, in accordance with another embodiment of the present invention, the competing stimulus is selected from a fixed stimulus, a varying stimulus and a transient stimulus.

Furthermore, in accordance with another embodiment of the present invention, the competing stimulus is selected from a stimulus which does not vary for the duration of presentation of the second pattern and a stimulus which varies within the duration of presentation of the second pattern.

Furthermore, in accordance with another embodiment of the present invention, the competing sensory stimulus is selected from a visual stimulus, an auditory stimulus, a somatosensory stimulus, a tactile stimulus, and a nociceptive stimulus.

Furthermore, in accordance with another embodiment of the present invention, the competing stimulus is a distracting sensory stimulus.

Furthermore, in accordance with another embodiment of the present invention, the competing sensory stimulus is a visual stimulus which is not a part of the first pattern or of the second pattern.

Furthermore, in accordance with another embodiment of the present invention, the competing sensory stimulus is an auditory stimulus selected from a single frequency sound and a multi-frequency sound.

Furthermore, in accordance with another embodiment of the present invention, at least one parameter of the competing sensory stimulus is modified in one or more of the repetitions of steps (a) to (e).

Furthermore, in accordance with another embodiment of the present invention, the at least one parameter is selected from the duration of the competing stimulus, the time of initiating the presenting of the competing sensory stimulus relative to the time of projecting of the second pattern, one or more characteristics of the competing sensory stimulus, and combinations thereof.

Furthermore, in accordance with another embodiment of the present invention, the competing sensory stimulus is an auditory stimulus, and the at least one parameter of said auditory stimulus which is modified is selected from the intensity of the auditory stimulus, the waveform of the auditory stimulus, the frequency of the auditory stimulus, the frequency distribution of the auditory stimulus, the frequency content of the auditory stimulus, the duration of the auditory stimulus, the envelope of the auditory stimulus and combinations thereof.

Furthermore, in accordance with another embodiment of the present invention, the competing sensory stimulus is a visual stimulus and the at least one parameter of said competing stimulus which is modified is selected from the size of the stimulus, the shape of the stimulus, the pattern of the stimulus, the duration of presentation of the stimulus, the color of the stimulus, the intensity of the stimulus, the luminance of the stimulus, the chrominance of the stimulus, the temporal variation of the stimulus, the timing of presentation of the stimulus to the individual, the position of projecting the stimulus on the retina, the position of the stimulus on said retina, the rate of movement of said stimulus on said retina, and combinations thereof.

Furthermore, in accordance with another embodiment of the present invention, the competing stimulus is a visual stimulus selected from a visual stimulus which is a part of the second pattern and a visual stimulus which is not a part of the second pattern.

Furthermore, in accordance with another embodiment of the present invention, the competing stimulus is a noisy visual background projected on the retina.

Furthermore, in accordance with another embodiment of the present invention, the competing stimulus is selected from a stimulus which does not vary for the duration of presentation of the second pattern and a stimulus which varies within the duration of presentation of the second pattern.

Furthermore, in accordance with another embodiment of the present invention, the competing sensory stimulus comprises an artificial distortion introduced into the second pattern.

Furthermore, in accordance with another embodiment of the present invention, the artificial distortion introduced into the second pattern mimics the appearance of the distortion perceived by an individual when a test pattern identical to the reference pattern is projected at a location of the retina of the individual which comprises a retinal or choroidal abnormality or a retinal and a choroidal abnormality.

Furthermore, in accordance with another embodiment of the present invention, the artificial distortion comprises at least a portion of the second pattern which is perceivably different than the corresponding part of the reference pattern.

Furthermore, in accordance with another embodiment of the present invention, the artificial distortion is selected from at least one portion of the second pattern which is distorted or shifted in comparison with the reference pattern, at least one optical property of at least one part of the second pattern which is different than the corresponding optical property of the remaining part of the second pattern, at least one portion of the second pattern which is visibly different in comparison with the corresponding portion of the reference pattern, at least one portion of the second pattern is missing in comparison with said reference pattern, and at least one portion of the second pattern which is blurred in comparison with the remaining part of the second pattern.

Furthermore, in accordance with another embodiment of the present invention, the competing sensory stimulus is selected from a fixed visual stimulus, a time varying visual stimulus, and a transient visual stimulus.

Furthermore, in accordance with another embodiment of the present invention, the first pattern, the reference pattern, and the second pattern are selected from a straight line and a segmented straight line.

Furthermore, in accordance with another embodiment of the present invention, the plurality of data of step (f) includes for each repetition of steps (a) to (e) one or more data items selected from the group consisting of data representing the position on the retina of the second pattern, data representing the orientation of the second pattern, data representing the position within the second pattern of the at least one localized part of the difference, and data representing one or more characteristics of the competing sensory stimulus.

Furthermore, in accordance with another embodiment of the present invention, the competing stimulus is a visual competing stimulus included in the second pattern and the plurality of data further includes data representing the position of the visual competing stimulus within the second pattern.

Furthermore, in accordance with another embodiment of the present invention, the step of processing includes determining for at least one group of competing sensory stimuli having common stimulus parameters the value of a competition grade and determining if the individual belongs to a group having a specific clinical stage of the eye disease based on the determined value of the competition grade.

Furthermore, in accordance with another embodiment of the present invention, the competition grade represents the efficiency of a group of competing sensory stimuli having common stimulus parameters in preventing the tested individual from reporting the presence of the difference of the perceived image, when said difference is caused by the eye disease.

Furthermore, in accordance with another embodiment of the present invention, the value of the competition grade is computed as the percentage of projected second patterns for which the individual reported at least one localized difference, caused by the eye disease, between the perceived image of the second pattern and the reference pattern, out of the total number of projected second patterns for which the individual was subjected to competing sensory stimuli belonging to a group of competing sensory stimuli having common stimulus parameters.

Furthermore, in accordance with another embodiment of the present invention, the second pattern is a segmented straight line, the competing sensory stimulus includes one or more segments of the segmented line which are shifted relative to the remaining segments of the straight line to form an artificial distortion having a defined amplitude. The position of the artificial distortion along the segmented straight line varies in at least some repetitions of the projecting of the second pattern, and within each group of competing sensory stimuli having common stimulus parameters, the amplitude of the artificial distortion is the same.

Furthermore, in accordance with another embodiment of the present invention, the second pattern is a segmented straight line, said competing sensory stimulus comprises one or more segments of said segmented line which are shifted relative to the remaining segments of said straight line to form an artificial distortion having a defined amplitude, and wherein said at least one localized difference is determined to be caused by said eye disease if the computed distance between the center of said artificial distortion and the position along the length of said segmented line at which said individual reported said at least one localized difference exceeds a preset value.

There is further provided, in accordance with a embodiment of the present invention, a method for obtaining data useful for detecting eye disease in an individual, the method includes the steps of:
(a) projecting a first pattern on a first location on the retina of an eye of the individual;
(b) fixating the individual's vision on a fixation target projected on the retina at or about the first location;
(c) hiding at least a portion of the first pattern;
(d) projecting a second pattern on a second location of the retina to allow the individual to form a perceived image of the second pattern;
(e) receiving from the individual input indicative of a difference in at least one localized part of the perceived image as compared to a predefined reference pattern, if the individual detected such a difference; and
(f) repeating steps (a) to (e) a number of times, wherein for at least some of the repetitions of steps (a) to (e), the individual is subjected to a competing sensory stimulus to obtain a plurality of data useful for detecting eye disease in the individual.

There is further provided, in accordance with a embodiment of the present invention, a method for detecting eye disease in an individual. The method includes the steps of:
fixating the individual's vision at or about a fixation target projected at a first retinal location of the retina of an eye of the individual;
projecting for a first duration a test pattern at a second retinal location of the eye, to allow the individual to form a perceived image of the test pattern;
receiving from the individual input indicative of a difference in at least one localized part of the perceived image as compared to a predefined reference pattern, if the individual detected such a difference;
repeating the steps of fixating, projecting and receiving a number of times to obtain a plurality of data, wherein in at least some of the repetitions of the steps of fixating, projecting, and receiving, the individual is subjected for a second duration to a competing sensory stimulus; and
processing the plurality of data to determine if the individual belongs to a group having a defined clinical stage of the eye disease.

Furthermore, in accordance with another embodiment of the present invention, the competing sensory stimulus is a sensory stimulus effective in modifying the ability of the individual to report a difference in at least one localized part of the perceived image as compared to a predefined reference pattern when the difference is perceived due to the eye disease.

Furthermore, in accordance with another embodiment of the present invention, the first duration is in the range of 10 milliseconds to 20 seconds.

Furthermore, in accordance with another embodiment of the present invention, the first duration is in the range of 100–160 milliseconds.

Furthermore, in accordance with another embodiment of the present invention, the step of fixating, the step of projecting, the step of receiving, the step of repeating and the step of analyzing are performed in the order recited above.

Furthermore, in accordance with another embodiment of the present invention, the projecting is performed in response to the fixating.

Furthermore, in accordance with another embodiment of the present invention, the eye disease is selected from the group consisting of age-related macular degeneration, choroidal neovascularization, ocular hystoplasmosis, myopia, central serous retinopathy, central serous choroidopathy, glaucoma, diabetic retinopathy, media opacities, cataract, retinitis pigmentosa, optic neuritis, epiretinal membrane, vascular abnormalities, vascular occlusions, choroidal dystrophies, retinal dystrophies, macular hole, choroidal degeneration, retinal degeneration, lens abnormalities, and combinations thereof.

Furthermore, in accordance with another embodiment of the present invention, in at least some of the repetitions of the steps of fixating, projecting, and receiving, the position of projecting of the test pattern on the retina is changed to map a selected region of the retina at a desired resolution.

Furthermore, in accordance with another embodiment of the present invention, in at least some of the repetitions of the steps of fixating, projecting, and receiving, the orientation of projecting of the test pattern on the retina is changed.

Furthermore, in accordance with another embodiment of the present invention, the competing sensory stimulus is selected from a competing stimulus presented before the projecting of the test pattern, a competing stimulus presented during at least part of the duration of projecting of the test pattern, a competing stimulus presented after the projecting of the test pattern, and a competing stimulus which temporally overlaps at least a part of the duration the projecting of the test pattern.

Furthermore, in accordance with another embodiment of the present invention, the competing stimulus is selected from a fixed stimulus, a varying stimulus and a transient stimulus.

Furthermore, in accordance with another embodiment of the present invention, the competing stimulus is selected from a stimulus which does not vary for the duration of presentation of the test pattern and a stimulus which varies within the duration of presentation of the test pattern.

Furthermore, in accordance with another embodiment of the present invention, the competing sensory stimulus is selected from a visual stimulus, an auditory stimulus, a somatosensory stimulus, a tactile stimulus, and a nociceptive stimulus.

Furthermore, in accordance with another embodiment of the present invention, the competing sensory stimulus is a distracting sensory stimulus.

Furthermore, in accordance with another embodiment of the present invention, the competing sensory stimulus is a visual stimulus which is not a part of the test pattern.

Furthermore, in accordance with another embodiment of the present invention, the competing sensory stimulus is an auditory stimulus selected from a single frequency sound and a multi-frequency sound.

Furthermore, in accordance with another embodiment of the present invention, at least one parameter of the competing sensory stimulus is modified in one or more of the repetitions of the steps of fixating, projecting, and receiving.

Furthermore, in accordance with another embodiment of the present invention, the at least one parameter which is modified is selected from the duration of the competing stimulus, the time of initiating the presenting of the competing sensory stimulus relative to the time of projecting of the test pattern, one or more characteristics of the competing sensory stimulus, and combinations thereof.

Furthermore, in accordance with another embodiment of the present invention, the competing sensory stimulus is an auditory stimulus. The at least one parameter of the auditory stimulus which is modified is selected from the intensity of the auditory stimulus, the waveform of the auditory stimulus, the frequency of the auditory stimulus, the frequency distribution of the auditory stimulus, the frequency content of the auditory stimulus, the duration of the auditory stimulus, the envelope of the auditory stimulus and combinations thereof.

Furthermore, in accordance with another embodiment of the present invention, the competing sensory stimulus is a visual stimulus and the at least one parameter of the competing stimulus which is modified is selected from the size of the stimulus, the shape of the stimulus, the pattern of the stimulus, the duration of presentation of the stimulus, the color of the stimulus, the intensity of the stimulus, the luminance of the stimulus, the chrominance of the stimulus, the temporal variation of the stimulus, the timing of presentation of the stimulus to the individual, the position of projecting the stimulus on the retina, the rate of movement of the stimulus on the retina, and combinations thereof.

Furthermore, in accordance with another embodiment of the present invention, the competing stimulus is a visual stimulus selected from a visual stimulus which is a part of the test pattern and a visual stimulus which is not a part of the test pattern.

Furthermore, in accordance with another embodiment of the present invention, the competing stimulus is a noisy visual background projected on the retina.

Furthermore, in accordance with another embodiment of the present invention, the sensory stimulus is selected from a stimulus which does not vary for the duration of presentation of the test pattern and a stimulus which varies within the duration of presentation of the test pattern.

Furthermore, in accordance with another embodiment of the present invention, the competing sensory stimulus includes an artificial distortion introduced into the test pattern.

Furthermore, in accordance with another embodiment of the present invention, the artificial distortion introduced into the test pattern mimics the appearance of the distortion perceived by an individual when a test pattern identical to the reference pattern is projected at a location of the retina of the individual which includes a retinal abnormality, or a choroidal abnormality, or a retinal and a choroidal abnormality.

Furthermore, in accordance with another embodiment of the present invention, the artificial distortion comprises at least a portion of the test pattern which is perceivably different than the corresponding part of the reference pattern.

Furthermore, in accordance with another embodiment of the present invention, the artificial distortion is selected from at least one portion of the test pattern being distorted or shifted in comparison with the reference pattern, at least one optical property of at least one part of the test pattern being different than the corresponding optical property of the remaining part of the test pattern, at least one portion of the test pattern is visibly different in comparison with the corresponding portion of the reference pattern, at least one portion of the test pattern is missing in comparison with the reference pattern, and at least one portion of the test pattern being blurred in comparison with the remaining part of the test pattern.

Furthermore, in accordance with another embodiment of the present invention, the competing sensory stimulus is selected from a fixed visual stimulus, a time varying visual stimulus, and a transient visual stimulus.

Furthermore, in accordance with another embodiment of the present invention, the test pattern, and the reference pattern is selected from a straight line and a segmented straight line.

Furthermore, in accordance with another embodiment of the present invention, the plurality of data of the step of repeating includes, for each repetition of the steps of fixating, projecting and receiving, one or more data items selected from the group consisting of, data representing the position on the retina of the test pattern, data representing the orientation of the test pattern, data representing the position within the test pattern of the at least one localized part of the difference, and data representing one or more characteristics of the competing sensory stimulus.

Furthermore, in accordance with another embodiment of the present invention, the competing stimulus is a visual competing stimulus included in the test pattern and the plurality of data further includes data representing the position of the visual competing stimulus within the test pattern.

Furthermore, in accordance with another embodiment of the present invention, the step of processing includes determining for at least one group of competing sensory stimuli having common stimulus parameters the value of a competition grade, and determining if the individual belongs to a group having a specific clinical stage of the disease based on the determined value of the competition grade.

Furthermore, in accordance with another embodiment of the present invention, the wherein said competition grade represents the efficiency of a group of competing sensory stimuli having common stimulus parameters in preventing the tested individual from reporting the presence of said difference of said perceived image, when said difference is caused by said eye disease.

Furthermore, in accordance with another embodiment of the present invention, the value of the competition grade is computed as the percentage of projected test patterns for which the individual reported at least one localized difference determined to be caused by said eye disease between the perceived image of the test pattern and the reference pattern, out of the total number of projected test patterns for which the individual was subjected to competing sensory stimuli belonging to a group of competing sensory stimuli having common stimulus parameters.

Furthermore, in accordance with another embodiment of the present invention, the test pattern is a segmented straight line, the competing sensory stimulus includes one or more segments of the segmented line which are shifted relative to the remaining segments of the straight line to form an artificial distortion having a defined amplitude. The position of the artificial distortion along the segmented straight line varies in at least some repetitions of the projecting of the test pattern, and within each group of competing sensory stimuli having common stimulus parameters, the amplitude of the artificial distortion is the same.

Furthermore, in accordance with another embodiment of the present invention, the test pattern is a segmented straight line, the competing sensory stimulus comprises one or more segments of the segmented line which are shifted relative to the remaining segments of the straight line to form an artificial distortion having a defined amplitude. The at least one localized difference is determined to be caused by the eye disease if the computed distance between the center of the artificial distortion and the position along the length of the segmented line at which the individual reported the at least one localized difference exceeds a preset value.

Furthermore, in accordance with another embodiment of the present invention, the relationship of the first duration and the second duration is selected from, the first duration is identical to the second duration, the second duration precedes the first duration, and the first duration at least partially overlaps with the second duration.

There is also provided, in accordance with an embodiment of the present invention, a method for obtaining data useful for detecting eye disease in an individual. The method includes the steps of:

fixating the individual's vision at or about a fixation target projected at a first retinal location of the retina of an eye of the individual;

projecting for a first duration a test pattern at a second retinal location of the eye, to allow the individual to form a perceived image of the test pattern;

receiving from the individual input indicative of a difference in at least one localized part of the perceived image as compared to a predefined reference pattern, if the individual detected such a difference; and repeating the steps of fixating, projecting and receiving a number of times, such that for at least some of the repetitions of the steps of fixating, projecting, and receiving, the individual is subjected for a second duration to a competing sensory stimulus, to obtain a plurality of data useful for detecting eye disease in the individual.

There is also provided, in accordance with an embodiment of the present invention, a system for detecting eye disease in an individual, the system includes:

means for projecting patterns on the retina of an eye of the individual;

means for fixating the individual's vision on a fixation target projected on the retina;

means for providing input representative of the position of a selected region of the retina at which a difference is observed by the individual between a perceived image of one of the patterns and a predetermined reference pattern;

means for controllably delivering to the individual competing sensory stimuli; and processing means operatively coupled to the means for projecting, the means for fixating, the means for providing input and the means for controllably delivering competing sensory stimuli. The processing means is configured to perform the steps of, (a) projecting a first pattern at a first location on the retina, (b) determining when the individual's vision is fixated on the fixation target, (c) hiding at least a portion of the first pattern after the individual's vision is fixated on the fixation target, (d) projecting a second pattern at a second location on the retina to allow the individual to form a perceived image of the second pattern, and (e) receiving from the individual input indicative of a difference in at least one localized part of the perceived image as compared to a predefined reference pattern, if the individual detected such a difference;

(f) repeating steps (a) to (e) a number of times to obtain a plurality of data, wherein in at least some of the repetitions of steps (a) to (e), the individual is subjected to a competing sensory stimulus.

Furthermore, in accordance with another embodiment of the present invention, the system further includes means for storing the plurality of data.

Furthermore, in accordance with another embodiment of the present invention, the means for controllably delivering to the individual competing sensory stimuli are selected from means for delivering visual stimuli, means for delivering auditory stimuli, means for delivering somatosensory stimuli, means for delivering tactile stimuli, and means for delivering nociceptive stimuli.

Furthermore, in accordance with another embodiment of the present invention, the processing means includes at least one processing unit selected from a processor, a microprocessor, a computer, a personal computer, a laptop computer, a controller, a remote processor or computer, a server, a remote server, a networked computer, and combinations thereof.

Furthermore, in accordance with another embodiment of the present invention, the means for projecting is selected from a display device, a beam scanning device, and a laser scanning ophtalmoscope-like device.

Furthermore, in accordance with another embodiment of the present invention, at least one of the means for fixating and means for providing input comprises a device selected from the group consisting of a pointing device, a computer input device, a keyboard, a mouse, a light pen, a touch sensitive display device, and combinations thereof.

Furthermore, in accordance with another embodiment of the present invention, the means for projecting patterns is configured for projecting test patterns and fixation targets on the retina.

Furthermore, in accordance with another embodiment of the present invention, at least one of the means for projecting, the means for providing input and the means for fixating includes one or more devices selected from a touch sensitive display device, a pointing device, a light pen, joystick, a mouse, a keyboard, a computer input device, and combinations thereof.

Furthermore, in accordance with another embodiment of the present invention, the means for projecting, the means for fixating and the means for providing input comprise a touch sensitive display device.

Furthermore, in accordance with another embodiment of the present invention, the means for fixating comprises a device for moving a cursor or a pattern projected by the means for projecting.

Furthermore, in accordance with another embodiment of the present invention, the means for fixating is selected from a pointing device, a computer input device, a computer mouse, a keyboard, a joystick, a light pen and a touch sensitive screen.

Furthermore, in accordance with another embodiment of the present invention, the means for providing input comprises a pointing device for operatively moving a cursor or a pattern projected by the means for projecting.

Furthermore, in accordance with another embodiment of the present invention, the processing means are configured to perform the step of processing the plurality of data to determine if the individual belongs to a group having a defined clinical stage of the eye disease.

Furthermore, in accordance with another embodiment of the present invention, the system also includes communication means for communicating the plurality of data for processing outside of the system.

Furthermore, in accordance with another embodiment of the present invention, the system also includes communication means for communicating with one or more devices outside of the system.

Furthermore, in accordance with another embodiment of the present invention, the competing sensory stimuli include visual competing stimuli and the means for controllably delivering to the individual competing sensory stimuli includes means for controllably modifying the patterns projected on the retina.

Furthermore, in accordance with another embodiment of the present invention, the system also includes means for providing output to a user. The means for providing output is operatively coupled to the processing means.

There is also provided, in accordance with an embodiment of the present invention, a system for detecting eye disease in an individual. The system includes:

a projecting unit for projecting test patterns and fixation targets on the retina of an eye of the individual;

at least one input device for providing input representing a difference observed by the individual between a perceived image of one of the test patterns and a predetermined reference pattern;

a competing sensory stimuli generating unit for controllably subjecting the individual to competing sensory stimuli; and at least one processing unit operatively coupled to the projecting unit, the at least one input device, and the competing sensory stimuli generating unit. The at least one processing unit is configured to perform the steps of, (a) projecting a first pattern at a first location on the retina, (b) determining when the individual's vision is fixated on the fixation target, (c) hiding at least a portion of the first pattern after the individual's vision is fixated on the fixation target, (d) projecting a second pattern at a second location on the retina to allow the individual to form a perceived image of the second pattern, (e) receiving from the individual input indicative of a difference in at least one localized part of the perceived image as compared to a predefined reference pattern, if the individual detected such a difference, and (f) repeating steps (a) to (e) a number of times to obtain a plurality of data, wherein in at least some of the repetitions of steps (a) to (e), the competing sensory stimuli generating unit subjects the individual to a competing sensory stimulus.

Furthermore, in accordance with another embodiment of the present invention, the system also includes a storage device for storing the plurality of data.

Furthermore, in accordance with another embodiment of the present invention, the projecting unit comprises the competing sensory stimuli generating unit.

Furthermore, in accordance with another embodiment of the present invention, the competing sensory stimuli generating unit is selected from a unit for delivering visual stimuli, a unit for delivering auditory stimuli, a unit for delivering somatosensory stimuli, a unit for delivering tactile stimuli, and a unit for delivering nociceptive stimuli.

Furthermore, in accordance with another embodiment of the present invention, the data is selected from, the presence of the difference within the perceived image of the second pattern, the approximate position within the perceived image of the difference, the position of a second pattern relative to the fixation target, the orientation of the second pattern on the retina, the presence of a distortion in the second patterns, the position of the distortion within the second pattern, the presence of a visually perceivable difference between one or more parts of the perceived image of the second pattern and the predefined reference pattern, the position of the one or more parts within the perceived image, one or more characteristics of the competing sensory stimuli, and combinations thereof.

Furthermore, in accordance with another embodiment of the present invention, the at least one processing unit is selected from a processor, a microprocessor, a computer, a personal computer, a laptop computer, a controller, a remote processor or computer, a server, a remote server, a networked computer, and combinations thereof.

Furthermore, in accordance with another embodiment of the present invention, the projecting unit is selected from a display device, a beam scanning device, and a laser scanning ophtalmoscope-like device.

Furthermore, in accordance with another embodiment of the present invention, the display device comprises a touch sensitive display device.

Furthermore, in accordance with another embodiment of the present invention, the at least one input device includes a device selected from the group consisting of a pointing device, a computer input device, a keyboard, a mouse, a light pen, a touch sensitive display device, and combinations thereof.

Furthermore, in accordance with another embodiment of the present invention, at least one of the projecting unit and the input device includes one or more devices selected from a touch sensitive display device, a pointing device, a light pen, joystick, a mouse, a keyboard, a computer input device, and combinations thereof.

Furthermore, in accordance with another embodiment of the present invention, the system also includes communication means for communicating with one or more devices outside of the system.

Furthermore, in accordance with another embodiment of the present invention, the system also includes at least one output device operatively coupled to the at least one processing unit for providing output to a user.

There is also provided, in accordance with another embodiment of the present invention, a system for detecting eye disease in an individual. The system includes:

means for projecting test patterns and fixation targets on the retina of an eye of the individual;

means for fixating the individual's vision on a fixation target projected on the retina;

means for providing input representative of the position on the retina at which a difference is observed by the individual between a perceived image of one of the patterns and a predetermined reference pattern;

means for controllably delivering to the individual competing sensory stimuli; and processing means operatively coupled to the means for projecting, the means for fixating, the means for providing input, and the means for controllably delivering to said individual competing sensory stimuli. The processing means is configured to perform the steps of fixating the individual's vision at or about a fixation target projected at a first location of the retina, projecting for a selected duration a test pattern at a second location of the retina to allow the individual to form a perceived image of the test pattern, receiving from the individual input indicative of a difference in at least one localized part of the perceived image of the step of projecting as compared to a predefined reference pattern, if the individual detected such a difference, and repeating the steps of fixating, projecting and receiving a number of times to obtain a plurality of data, wherein in at least some of the repetitions of the steps of fixating, projecting and receiving, the individual is subjected to a competing sensory stimulus.

Furthermore, in accordance with another embodiment of the present invention, the processing means is configured for performing the step of analyzing the plurality of data to determine whether the individual has an eye disease.

Furthermore, in accordance with another embodiment of the present invention, the system also includes means for storing the plurality of data.

Furthermore, in accordance with another embodiment of the present invention, the means for controllably delivering to the individual competing sensory stimuli are selected from means for delivering visual stimuli, means for delivering auditory stimulus, means for delivering somatosensory stimuli, means for delivering tactile stimuli, and means for delivering nociceptive stimuli.

Furthermore, in accordance with another embodiment of the present invention, the processing means includes at least one processing unit selected from a processor, a microprocessor, a computer, a personal computer, a minicomputer, a laptop computer, a controller, a remote processor or computer, a server, a remote server, a networked computer, and combinations thereof.

Furthermore, in accordance with another embodiment of the present invention, the means for projecting is selected from a display device, a beam scanning device, and a laser scanning ophtalmoscope-like device.

Furthermore, in accordance with another embodiment of the present invention, at least one of the means for fixating and means for providing input includes a device selected from the group consisting of a pointing device, a computer input device, a keyboard, a mouse, a graphic tablet, a light pen, a touch sensitive screen, and combinations thereof.

Furthermore, in accordance with another embodiment of the present invention, the means for fixating includes a device for moving a cursor or a pattern projected by the means for projecting.

Furthermore, in accordance with another embodiment of the present invention, the system also includes communication means for communicating with one or more devices outside of the system.

Furthermore, in accordance with another embodiment of the present invention, the means for providing input includes a pointing device for operatively moving a cursor or a pattern projected by the means for projecting.

Furthermore, in accordance with another embodiment of the present invention, the processing means are configured to perform the step of processing the plurality of data to determine if the individual belongs to a group having a defined clinical stage of the eye disease.

Furthermore, in accordance with another embodiment of the present invention, the competing sensory stimuli comprise visual competing stimuli and the means for controllably delivering to said individual competing sensory stimuli comprise means for controllably modifying test patterns projected on the retina.

Furthermore, in accordance with another embodiment of the present invention, the system also comprises means for providing output to a user. The means for providing output is operatively coupled to the processing means.

There is also provided, in accordance with another embodiment of the present invention, a system for detecting eye disease in an individual. The system includes:

a projecting unit for projecting test patterns and fixation targets on the retina of an eye of the individual;

at least one input device for providing input representing a difference observed by the individual between a perceived image of one of the test patterns and a predetermined reference pattern;

a competing sensory stimuli generating unit for controllably subjecting the individual to competing sensory stimuli; and at least one processing unit operatively coupled to the projecting unit, the at least one input device, and the competing sensory stimuli generating unit. The at least one processing unit is configured to perform the steps of, fixating the individual's vision at or about a fixation target projected at a first location of the retina, projecting for a selected duration a test pattern at a second location of the retina, to allow the individual to form a perceived image of the test pattern, receiving from the individual input indicative of a difference in at least one localized part of the perceived image of the step of projecting as compared to a predefined reference pattern, if the individual detected such a difference, and repeating the steps of fixating, projecting and receiving a number of times to obtain a plurality of data, wherein in at least some of the repetitions of the steps of fixating, projecting and receiving, the individual is subjected to a competing sensory stimulus.

Furthermore, in accordance with another embodiment of the present invention, the system further includes a storage device for storing the plurality of data.

Furthermore, in accordance with another embodiment of the present invention, the projecting unit comprises said competing sensory stimuli generating unit.

Furthermore, in accordance with another embodiment of the present invention, the data is selected from, the presence of the difference within the perceived image, the approximate position within the perceived image of the difference, the position of the test patterns relative to the fixation target, the orientation of the test patterns on the retina, the presence of a distortion in the test patterns, the position of the distortion within a test pattern, the presence of a visually perceivable difference between one or more parts of the perceived image and the predefined reference pattern, the position of the one or more parts within the perceived image, one or more characteristics of the competing sensory stimuli, and combinations thereof.

Furthermore, in accordance with another embodiment of the present invention, the processing unit is selected from a processor, a microprocessor, a computer, a personal computer, a laptop computer, a controller, a remote processor or computer, a server, a remote server, a networked computer, and combinations thereof.

Furthermore, in accordance with another embodiment of the present invention, the projecting unit is selected from a display device, a beam scanning device, and a laser scanning ophtalmoscope-like device.

Furthermore, in accordance with another embodiment of the present invention, the display device comprises a touch sensitive display device.

Furthermore, in accordance with another embodiment of the present invention, the at least one input device comprises a device selected from the group consisting of a pointing device, a computer input device, a keyboard, a mouse, a light pen, a touch sensitive display device, and combinations thereof.

Furthermore, in accordance with another embodiment of the present invention, at least one of the projecting unit and the input device comprises one or more devices selected from a touch sensitive display device, a pointing device, a light pen, joystick, a mouse, a keyboard, a computer input device, and combinations thereof.

Furthermore, in accordance with another embodiment of the present invention, the system also includes communication means for communicating with one or more devices outside of the system.

Furthermore, in accordance with another embodiment of the present invention, the system also includes at least one output device operatively coupled to the at least one processing unit for providing output to a user.

There is also provided, in accordance with another embodiment of the present invention, a program storage device readable by machine, tangibly embodying a program of instructions executable by the machine to perform method steps for detecting eye disease in an individual. The program includes the steps of:

(a) projecting a first pattern on a first location on the retina of an eye of the individual;

(b) fixating the individual's vision on a fixation target projected on the retina at or about the first location;

(c) hiding at least a portion of the first pattern;

(d) projecting a second pattern on a second location of the retina to allow the individual to form a perceived image of the second pattern;

(e) receiving from the individual input indicative of a difference in at least one localized part of the perceived image as compared to a predefined reference pattern, if the individual detected such a difference; and (f) repeating steps (a) to (e) a number of times to obtain a plurality of data, wherein in at least some of the repetitions of steps (a) to (e), the individual is subjected to a competing sensory stimulus.

Furthermore, in accordance with another embodiment of the present invention, the repeating of step (f) is performed such that in at least some of the repetitions of steps (a) to (e) the location of projecting of at least the second pattern on the retina is changed.

Furthermore, in accordance with another embodiment of the present invention, the method steps of the program also include the step of processing the plurality of data to determine if the individual belongs to a group having a defined clinical stage of the eye disease.

Furthermore, in accordance with another embodiment of the present invention, the method steps of the program also include the step of communicating the plurality of data to a device external to the computer for processing the plurality of data to determine if the individual belongs to a group having a defined clinical stage of the eye disease.

There is also provided, in accordance with another embodiment of the present invention, a computer program product comprising a computer useable medium having computer readable program code embodied therein for detecting eye disease in an individual. The computer program product includes:

computer readable program code for causing a computer or a projecting device operatively coupled to the computer to project a first pattern on a first location on the retina of an eye of the individual;

computer readable program code for causing the computer to determine when the individual's vision is fixated on a fixation target projected on the retina at or about the first location and for hiding at least a portion of the first pattern when the individual's vision is fixated on the fixation target;

computer readable program code for causing the computer to project a second pattern at a second location of the retina to allow the individual to form a perceived image of the second pattern;

computer readable program code for causing the computer to receive from said individual input indicative of a difference in at least one localized part of the perceived image as compared to a predefined reference pattern, if the individual detected such a difference; and computer readable program code for causing the computer to perform a selected number of repetitions of the projecting of a first pattern, the determining when the individual's vision is fixated on the fixation target projected on the retina, the hiding of at least a portion of the first pattern when the individual's vision is fixated on the fixation target, the projecting of a second pattern at a second location of the retina to allow the individual to form a perceived image of the second pattern, and the receiving from the individual of input indicative of a difference in at least one localized part of the perceived image as compared to the predefined reference pattern if the individual detected such a difference, for obtaining a plurality of data, wherein in at least some of the repetitions the individual is subjected to a competing sensory stimulus.

Furthermore, in accordance with another embodiment of the present invention, the computer readable program code further includes computer readable program code for causing the computer to process the plurality of data to determine whether the individual has an eye disease.

Furthermore, in accordance with another embodiment of the present invention, the computer readable program code further includes computer readable program code for causing the computer to communicate the plurality of data to a device external to the computer for processing the plurality of data to detect the eye disease.

Furthermore, in accordance with another embodiment of the present invention, the computer readable program code further includes computer readable program code for causing the computer to change the location of projecting of at least the second pattern on the retina in at least some of the repetitions.

There is also provided, in accordance with another embodiment of the present invention, a program storage device readable by machine, tangibly embodying a program of instructions executable by the machine to perform method steps for detecting eye disease in an individual. The method includes the steps of:

fixating the individual's vision at or about a fixation target projected at a first retinal location of the retina of an eye of the individual;

projecting for a first duration a test pattern at a second retinal location of the eye, to allow the individual to form a perceived image of the test pattern;

receiving from the individual input indicative of a difference in at least one localized part of the perceived image as compared to a predefined reference pattern, if the individual detected such a difference; and repeating the steps of fixating, projecting and receiving a number of times to obtain a plurality of data, wherein for at least some of the repetitions of the steps of fixating, projecting, and receiving, the individual is subjected for a second duration to a competing sensory stimulus.

Furthermore, in accordance with another embodiment of the present invention, in at least some of the repetitions of the step of repeating, the location of projecting of the test pattern on the retina is changed.

Furthermore, in accordance with another embodiment of the present invention, the method steps of the program also include the step of processing the plurality of data to determine if the individual belongs to a group having a defined clinical stage of the eye disease.

Furthermore, in accordance with another embodiment of the present invention, the method steps of the program also include the step of communicating the plurality of data to a device external to the computer for processing the plurality of data to determine if the individual belongs to a group having a defined clinical stage of the eye disease.

There is also provided, in accordance with another embodiment of the present invention, a computer program product comprising a computer useable medium having computer readable program code embodied therein for detecting eye disease in an individual. The computer program product includes:

computer readable program code for causing a computer or a projecting device operatively coupled to the computer to project a fixation target at a first retinal position of an eye of the individual;

computer readable program code for causing the computer to determine when the individual's vision is fixated at or about the fixation target, and for projecting for a selected duration, when the individual's vision is fixated on the fixation target, a test pattern at a second retinal position of the eye, to allow the individual to form a perceived image of the test pattern;

computer readable program code for causing the computer to receive from the individual input indicative of a difference in at least one localized part of the perceived image as compared to a predefined reference pattern, if the individual detected such a difference; and computer readable program code for causing the computer to perform a selected number of repetitions of the projecting of the test pattern, the determining when the individual's vision is fixated at or about the fixation target, the projecting of a test pattern at the second location, and the receiving of the input from the individual if the individual detected such a difference, for obtaining a plurality of data, wherein in at least some of the repetitions the individual is subjected to a competing sensory stimulus.

Furthermore, in accordance with another embodiment of the present invention, the computer readable program code further includes computer readable program code for causing the computer to change the location of projecting of the test pattern on the retina in at least some of the repetitions.

Furthermore, in accordance with another embodiment of the present invention, the computer readable program code further includes computer readable program code for causing the computer to process the plurality of data to determine whether the individual has an eye disease.

Finally, in accordance with another embodiment of the present invention, the computer readable program code also includes computer readable program code for causing the computer to communicate the plurality of data to a device external to the computer for processing the plurality of data to detect the eye disease.

BRIEF DESCRIPTION OF THE DRAWINGS

The invention is herein described, by way of example only, with reference to the accompanying drawings, in which like components are designated by like reference numerals, wherein:

FIGS. 2A and 2B are a schematic flow chart diagram illustrating a method of executing an eye test for detecting an eye disease using a system such as the system illustrated in FIG. 1, in accordance with an embodiment of the present invention;

DETAILED DESCRIPTION OF THE INVENTION

The following terms are used throughout the application:

| Term | Definition |
| --- | --- |
| AD | Artificial distortion |
| AIOD | Artificially induced observed distortion |
| AMD | Age-related macular degeneration |
| CNV | Choroidal Neovascularization |
| CS | Competing stimulus |
| DVS | Distracting visual stimulus |
| GA | Geographic atrophy |
| HRC | High risk characteristics |
| LAN | Local area network |
| MCPT | Macular computerized psychophysical test |
| PAN | Private area network |
| PDT | Photodynamic Therapy |
| PROD | Pathology related observed distortion |
| PSTN | Public service telephone network |
| RPE | Retinal pigment epithelium |
| SLO | Scanning Laser Ophtalmoscope |
| TTT | Trans-pupilary Thermotherapy |
| VPN | Virtual private network |
| WAN | Wide area network |

It is noted that the test or tests for eye disease of the present invention disclosed hereinbelow may also be generally referred to as the Macular computerized psychophysical test (MCPT) hereinafter.

Figure 1:
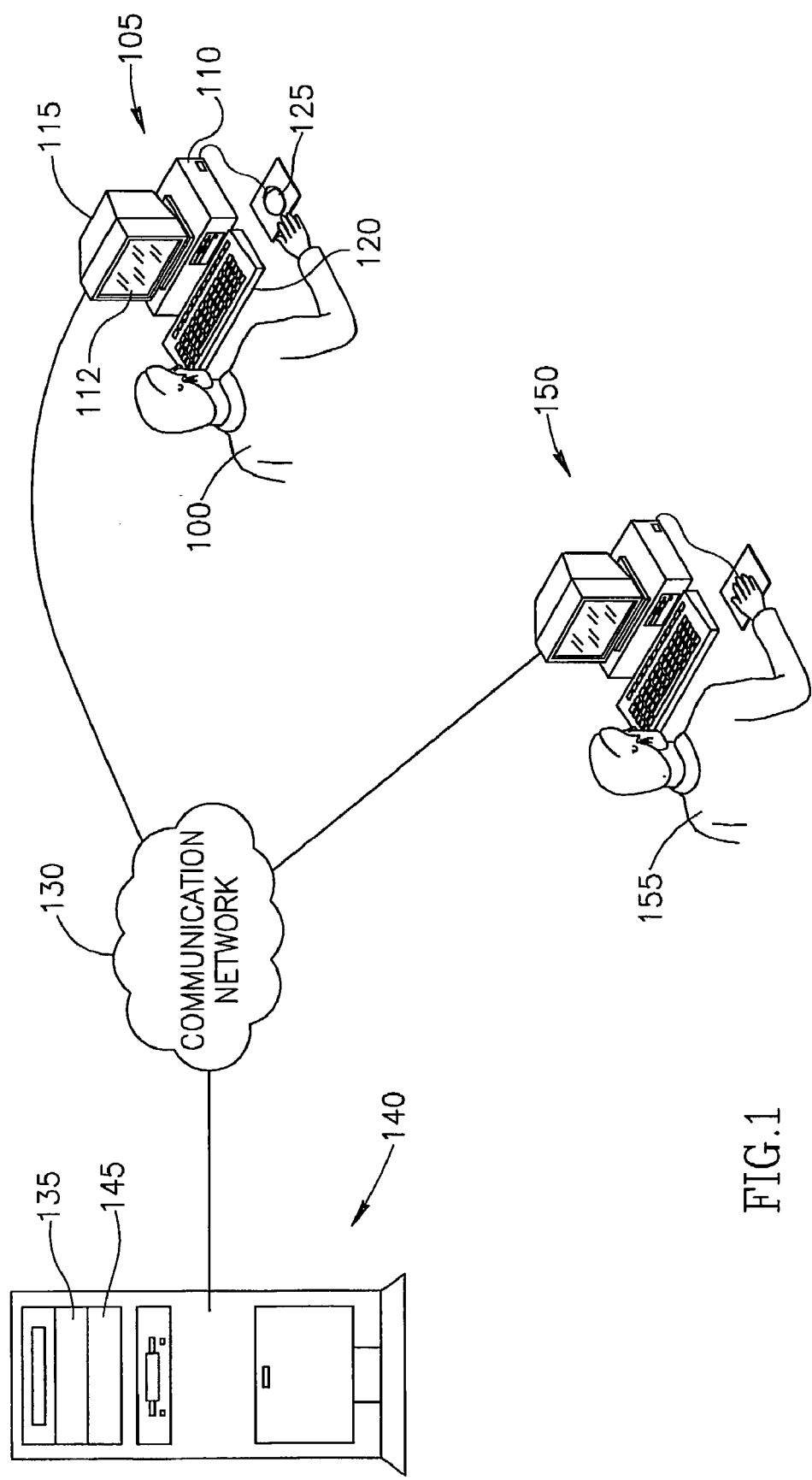
FIG. 1 is a schematic diagram illustrating a system for carrying out an eye test to detect an eye disease according to one embodiment of the invention.

FIG. 1 is a schematic diagram illustrating a system for carrying out an eye test to detect an eye disease according to one embodiment of the invention. A subject 100 performs an eye test using a computer system 105. The computer system 105 may comprise a computer 110, a display device 115 having a screen 112 and one or more computer input devices such as a keyboard 120 or a computer mouse 125. The computer system 105 may communicate over a communication network schematically indicated by the cloud labeled 130. The network 130 may be, for example, the Internet, a local area network (LAN), a wide area network (WAN), an Intranet, a private area network (PAN), the public service telephone network (PSTN), virtual networks implemented over the Internet, other private and/or commercial communication networks, or any other suitable type of communication network known in the art.

A processor 135 in a network server 140 stores data relating to execution of an eye test to be performed by the subject 100 to be described in detail below. The eye test is communicated from the server 140 to the subject's computer 110 over the network 130. The subject 100 inputs responses to the eye test using one or more of the computer input devices such as the keyboard 120 or the mouse 125. The subject's responses are communicated over the network 130 to the processor 135, and stored in the memory 145. The processor 135 is configured to analyze the subject's response, to make a diagnosis of the subject's conditions and to recommend future follow-up or recommend prompt examination, all in real time, for the subject.

The diagnosis and recommendation may be communicated over the network 130 to the subject's computer system 105 and/or to a terminal 150 of a health care provider 155. The processor 135 is also configured to store in the memory 145 dates on which the subject is to perform an eye test executed by the processor 135. If, for example, the subject 100 has been instructed by the health care provider 155 to perform the test once per week, the processor 135 may send a message over the communication network 130 when 10 days have elapsed since the last time he took the test, informing the subject of his failure to take the test as instructed. A similar message may be sent to the health care provider 155. A responsible individual may be designated, in such a case, to contact the subject 100, for example, by telephone to clarify why the subject 100 has not performed the test as instructed and to impress upon the subject the importance of performing the test as indicated.

"Moving pattern" Test Method

The method disclosed hereinbelow is based on the presentation of a first pattern at a first location on the surface of a display device (such as, but not limited to the screen 112 of the display device 115) to the patient or the test subject. After the patient fixated on a fixation target presented on or adjacent to the first pattern, the first pattern disappears from the first location of the display device and a second pattern is presented at a second location on the display device. The second pattern may be identical to the first pattern (except for the fact that it appears at a different location on the display device) or it may be different from the first pattern by having one or more portions thereof changed or altered, or, preferably, transiently changed or transiently altered.

Such changes or transient changes or alterations may include distortion of the shape or elimination of one or more portions of the first pattern, or changes in the color or appearance of one or more portions of the first pattern. Because the first pattern is made to disappear from the first location on the display device and the second pattern appears at a second location of the display device different than the first location, the patient or test subject may visually perceive this as a movement or jump of the pattern from the first location to the second location on the display device. In other words, the patient may perceive a pattern "jumping" on the screen of the display device from a first to a second location even though the pattern does not actually move on the display device (the pattern actually disappears from a first location on the display device and appears at a second location on the display device). This is why this particular embodiment of the testing method is referred to as the "moving pattern" or "jumping pattern" test hereinafter.

Figure 2B:
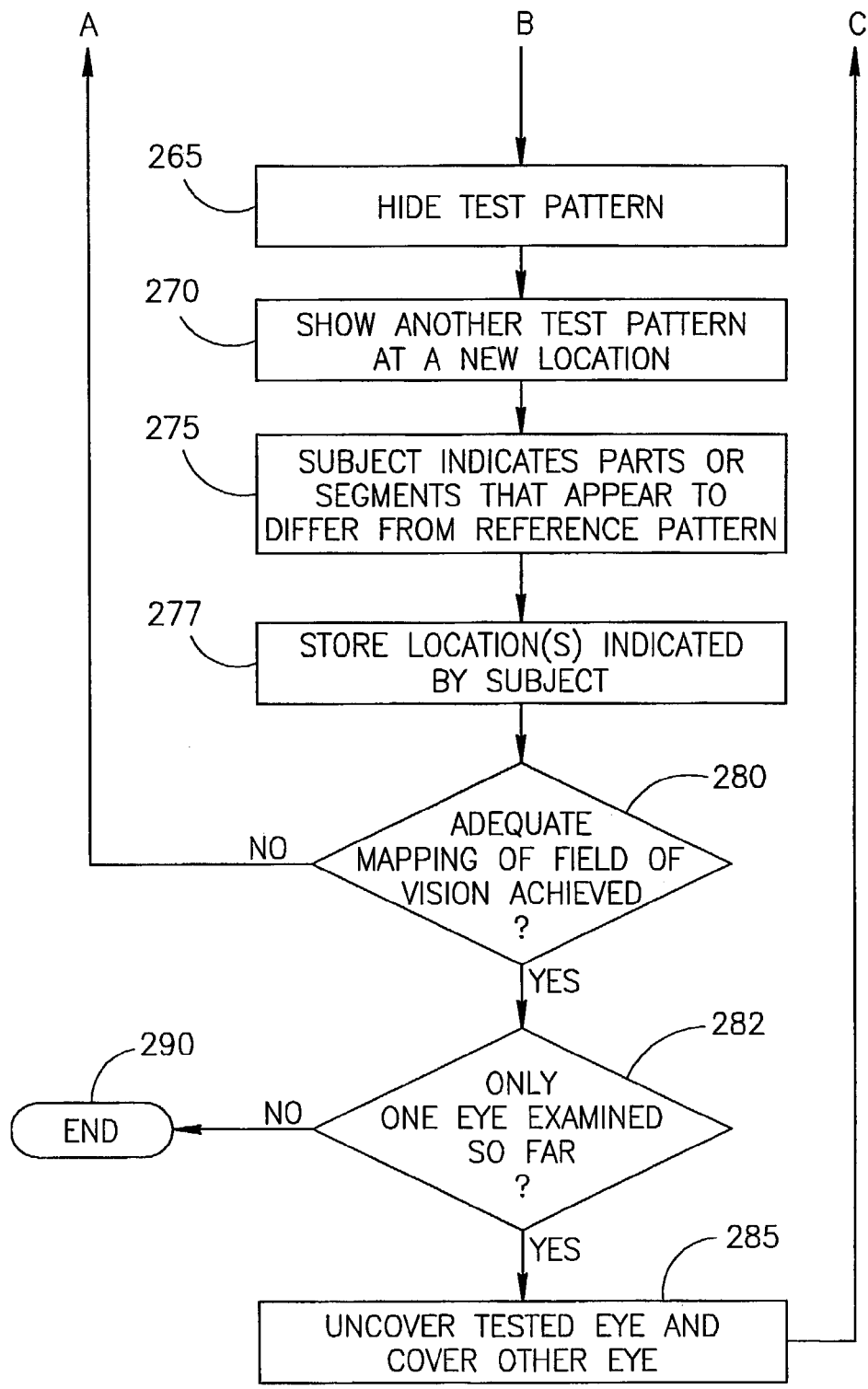

FIGS. 2A and 2B are a schematic flow chart diagram illustrating a method of executing an eye test for detecting an eye disease using a system such as the system illustrated in FIG. 1, in accordance with an embodiment of the present invention.

Figure 3:
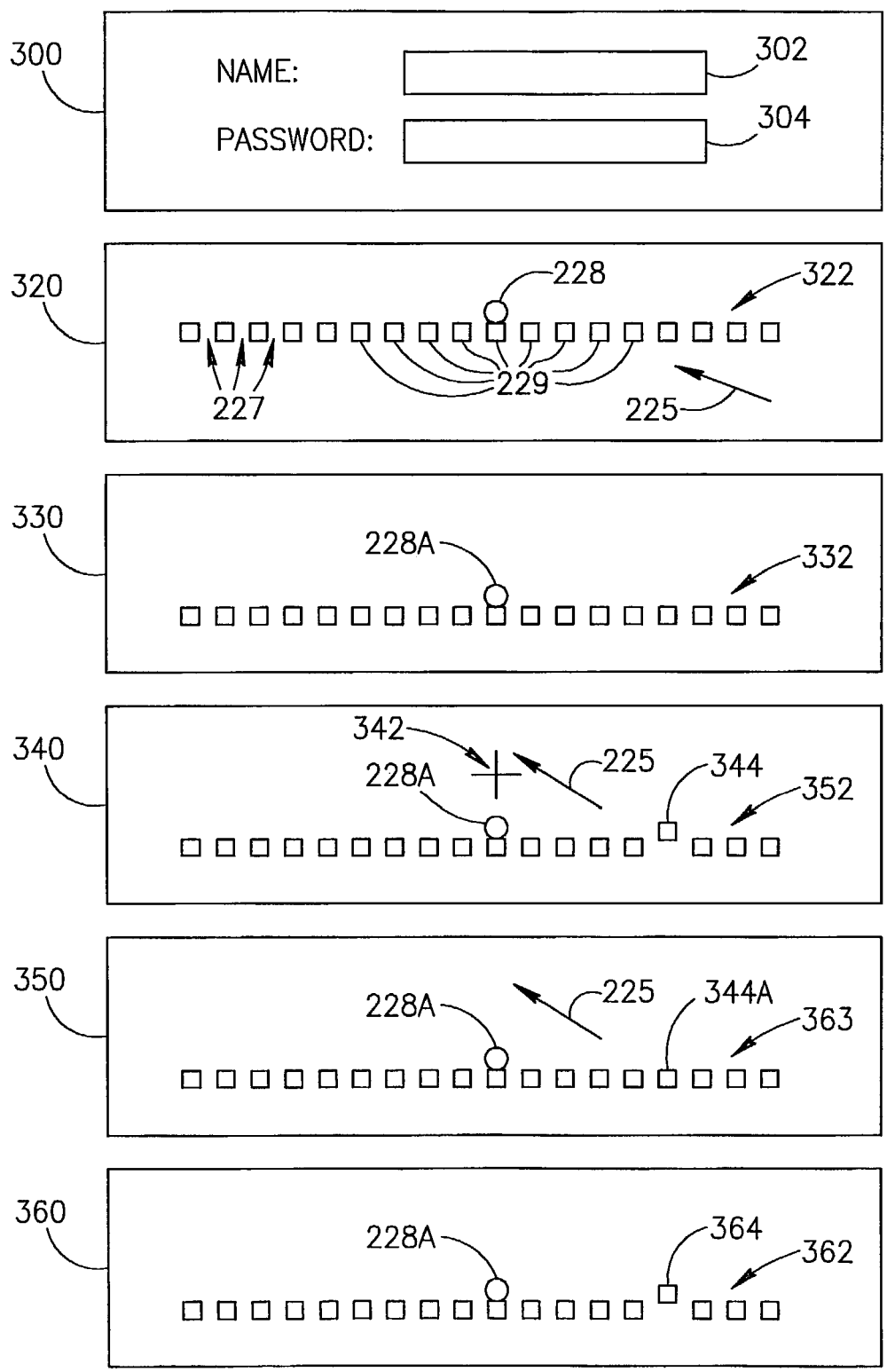
FIG. 3 schematically illustrates selected exemplary screen representations including exemplary test patterns which may be presented to a tested subject, in an exemplary embodiment of the testing method of the present invention, and selected schematic representations of how the test patterns may be perceived by a tested subject in selected stages of the testing.

FIG. 3 schematically illustrates selected exemplary screen representations including exemplary test patterns which may be presented to a tested subject, in an exemplary embodiment of the testing method of the present invention, and selected schematic representations of how the test patterns may be perceived by a tested subject in selected stages of the testing.

FIG. 3 includes schematic screen diagrams 300, 320, 330 and 360 (also referred to as screens 300, 320, 330 and 360 hereinafter) which schematically illustrate the patterns displayed on the screen 112 of the subject's display device 115 at various different exemplary steps of the eye test performed by the system illustrated in FIG. 2, and schematic screen diagrams 340 and 350 (also referred to as screens 340 and 350 hereinafter) which schematically illustrate the possible appearance of the screen 112 as may be perceived by the tested subject at some exemplary steps of the eye test. It is noted that screen 300 of FIG. 3 which does not include test patterns, schematically represents a possible log-on screen which may be presented to the test subject.

It is noted that the exemplary schematic screens 300, 320, 330, 340, 350, and 360 of FIG. 3 are schematically drawn for illustrative purposes only and are not drawn to scale. Additionally, the sizes of the various patterns, pattern segments and fixation targets are not drawn to scale, and their sizes and their relation to the screen size are arbitrarily shown for illustrative purposes only.

Turning to FIG. 2, in step 200, the subject 100 may log onto the computer system 105. The processor 135 may cause log-on screen 300 to be displayed on the subject's display device 115 (step 205). The log-on screen 300 prompts the subject to input his name into a field 302 and to input a previously assigned password into a field 304 for accessing the processor 135. In step 210 the subject inputs his name and password using computer input devices such as the keyboard 120 or the mouse 125. The processor 135 then checks whether the inputted name and password are stored in the memory 145 (step 215). If the inputted name and password do not match a corresponding name and password which are stored in the memory 145, the processor 135 determines whether the number of attempts the subject has made to input a name and password is less than a predetermined number of attempts such as, for example, three attempts (step 220). If yes, the process returns to step 205. If no, the process terminates.

If at step 215 the processor determines that the name and password are in the memory 145, the process continues in step 248 by the subject being instructed to cover an eye, so that the test is performed using one eye only. The subject may be instructed to cover an eye by displaying appropriate text (not shown) or a drawing (not shown) or an icon (not shown), or a graphic element (not shown) or any combination thereof on the screen of the display device 115.

It is noted that the tested subject 100 may be asked to cover a specific-eye (for example, the subject may be asked to cover the right eye and to view the screen 112 with the uncovered left eye for testing the left eye). In this way the computer system 110 may automatically record that the left eye is being tested. However, the test may also be performed with both eyes open as a selected eye is being tested. Alternatively, the tested subject 100 may be asked to mark or input or otherwise indicate which eye is to be tested, such as, for example, by clicking a cursor on one of two boxes (not shown) which may be presented on the log-on screen 300 or on any other suitable screen presented to the subject before the test begins. In such a case the test results may be labeled as taken from the eye selected by the subject 100.

In step 250 a form screen 320 is displayed in which a pattern, such as the segmented line 322, is displayed. This is by way of example only, and other suitable patterns may be used within the scope of the invention. The pattern may comprise a single component, or may comprise several components, which may or may not be all identical. Thus, the pattern may comprise several lines, one or more circles, lines and circles together, or any other suitable combination of pattern elements, including but not limited to one or more straight lines, dotted lines, curved lines, linear or non linear segments, dots, and other various geometrical patterns such as but not limited to circles, arcs, rectangles, squares, triangles and the like. The screen 112 of the display device 115 may display a visually noisy background to the displayed pattern. The line 322 may be composed of several short segments 229 separated by gaps 227. Alternatively, the displayed line may be continuous (not shown).

Preferably, the length of the line 322 is such that when the tested subject's eye is at a distance of approximately 50 centimeter from the screen 112 of the display device 115, the length of the line 322 corresponds to a cone angle of 1–20°. It is, however, noted that other different cone angles and other different viewing distances (smaller or larger than 50 centimeters from the screen 112) may be used. Additionally, it may be possible, in accordance with other embodiments of the invention, to use "virtual reality" goggles worn by the patient which may have different screen sizes and may be disposed at a different distance from the patient eye.

It is noted that while in most tests the length of the lines used corresponded to a cone angle of 14°, other different line lengths may be used. At these viewing conditions, each of the gaps 227 between the segments 229 (the distances separating two adjacent segments 229) may correspond to a cone angle of between 1 minutes arc to about 2° (two degrees). Other different line lengths and gap sizes may however also be used. For example, if the test pattern is a continuous line there are no gaps.

It is also noted that if test patterns which comprise a continuous line are used, no segments are used and there are therefore no gaps.

If the pattern includes two or more parallel lines, the spacing between the lines corresponds, preferably, to a cone angle from about 10 to about 600 minutes arc. The test patterns may be horizontal patterns such as, but not limited to, the horizontal line 322 illustrated in screen 300, but may also be vertical patterns such as but not limited to a vertical segmented line (not shown) or slanted patterns such as, but not limited to, a slanted segmented line (not shown). A fixation target 228 may be displayed on the screen adjacent to one of the segments 229. The fixation target may be a circular pattern such as the circular fixation target 228 of screen 320 of FIG. 3, or may have any other shape or pattern suitable for serving as a fixation target to focus the tested eye thereon, such as, but not limited to, a square pattern, a triangular pattern, or any other suitable pattern which is suitable for functioning as a fixation target.

It is noted that while the fixation target 228 illustrated in FIG. 3 is a circular pattern which appears close to the middle segment of the line 322, other different forms of the fixation target may be used. For example, the fixation target may be implemented as a hollow (unfilled) circle (not shown) surrounding the middle segment of the line 322 or superimposed thereon, or as any other suitable pattern which is positioned close to or is superimposed upon the line 322.

Generally, the shape of the fixation target may depend, inter alia, on the shape and dimensions of the test pattern which is being used in the test. The fixation target may have the same color of the test pattern (such as, for example, the segmented line 322) or may have a different color than the color of the test pattern. In accordance with another variation, the fixation target may be the central (middle) segment of the line 322, in which case the middle segment may or may not have a color which is different than the color of the remaining segments 229 of the line 322, in order to make it easily identifiable by the test subject.

In the example in which a single segmented line serves as the test pattern, the subject may be instructed to bring a cursor 225 appearing on the screen to the fixation target 228. In order to aid the subject, the movement of the cursor 225 may be restricted to a line (not shown) which is parallel to the line 322 so that the cursor 225 always points to one of the segments 229.

The subject 100 may be asked (for example, by an instructor, a physician an ophtalmologist or any other person training the subject in performing the test) or otherwise instructed (such as for example by displaying appropriate messages or text an the screen 112 of the display device 115) to point the cursor 225 at the fixation target 228. The subject 100 may perform this pointing in step 255 by using a computer device such as the keyboard 120, or more preferably the mouse 125. Other pointing devices may also be used for pointing, such as but not limited to, a keypad, a digitizing tablet in conjunction with a stylus, or a finger, a light pen in conjunction with a touch sensitive screen or a touch sensitive display device, a joystick or any other suitable pointing device or suitable input device or computer input device known in the art.

The fixation target 228 may be sized so that it is large enough to be seen by the patient or test subject, but small enough so that bringing the cursor 225 to the fixation target 228 is a demanding task for the test subject. This causes the subject to fixate his vision on the fixation target 228. Upon bringing the cursor to the segment 229, the subject may provide a suitable indication that he has positioned the cursor 225 to point at the fixation target 228. For example, the patient or test subject 100 may provide the indication by clicking on the mouse 125 or by depressing a predetermined key on the keyboard 120 (step 260). This input may serve as an indication or a verification that visual fixation has been achieved. It is noted that the size of the fixation target 228 may depend, inter alia, on the distance of the tested eye from the screen 112.

It is noted that if the subject is using a pointing device and/or an input device which is different than the mouse 125 or the keyboard 120, the subject may indicate fixation on the fixation target 228 by performing any other suitable action. For example, if a touch screen (not shown) is used as an input device, the subject may touch the touch screen (not shown) with a light pen (not shown), or with a stylus (not shown) or with a finger (not shown) at the position at which the fixation target is displayed. Other suitable forms of indicating or confirming fixation may be used, depending, inter alia, on the input device or pointing device which is being used.

When the subject signals (for example, by clicking a button on the mouse 125, or by any other suitable way) that the cursor 225 is positioned to point at the fixation target 228, indicating that his vision is fixated on the fixation target 228, the line 322 is made to disappear from the screen 320 (step 265). After a predetermined delay time interval (for example a delay interval in the range of 0 to 200 milliseconds), a second pattern such as the segmented line 332 is made to appear (displayed) on the screen 112 at a location different than the location of the line 322 as shown in screen 330 (step 270), so as to allow the subject to form a perceived image of the segmented line 332. In this example, the segmented line 332 is similar to the line 322 but appears on the screen 112 at a location which is different than the location of the line 322.

It is noted that if the duration of the delay time interval is zero, the line 332 is presented on the screen 112 immediately after (or within the short time required by the computer 100 to process the subject's input and display the line 332 on the screen 112) the subject 100 indicated fixation. In most of the experimental eye tests conducted in patients no delay was used (the delay time interval was zero).

The line 332 may, for example, be parallel to the line 322. Since the subject's vision had been fixated on the fixation target 228, the line 332 will appear in the periphery of the subject's field of vision. Any disturbance in his vision due to a retinal or choroidal lesion (such as but not limited to a lesion caused by AMD or diabetes or by other different pathological eye conditions) may be apparent to the test subject as a difference between the perceived image of the second pattern and a pre-defined reference pattern, which in this example is provided by the first pattern (the segmented straight line 322).

Additionally, or alternatively, the tested patient or subject 100 may have been told by a trainer (such as, for example, by an ophtalmologist or other medical or paramedical personnel) before the beginning of the test that he or she is going to be presented with test patterns which will look like a segmented straight line. In such a case, the subject 100 may conceive a "virtual" predetermined reference pattern which in this particular example of the test is a conceived image of a straight segmented line. The word "virtual" is used herein to indicate that the predetermined reference pattern is mentally conceived by the patient or test subject without having to actually present the patient with the test pattern. In other words, the understanding of the patient of how the reference pattern (such as, for example, the straight segmented line of the example illustrated in FIG. 3) is supposed to look like may be based on the previous visual experience of the patient or test subject.

The explanation to the patient of what the reference pattern is going to look like may be advantageous, since in a small percentage of patients it may happen that in the first presentation of the first test pattern (such as for example in the initial presentation of the line 322) the image of the test pattern may fall on a lesioned retinal or choroidal region. In such a case, the perceived image of the test pattern may be distorted. Therefore, in such a case, the perceived image of the initially presented line 322 is not usable as a reference pattern and the patient may see or detect a difference between the perceived image of the line 322 and the (virtual) reference image which the patient has been told to expect.

The difference between the perceived image of any of the test, patterns (including, but not limited to, the lines 322 and 332) which may be presented to the patient and the reference pattern may be perceived by the test subject 100 in various different ways. Thus, as the line 322 is perceived by the subject to jump or move to the new location on the screen 112 one or more of the segments 229 of the line may seem to the subject not to arrive at their new position on the line 332 (of the screen 330) at exactly the same pace or contour as the other segments. In other words, one or more portions or segments of the line may temporarily seem to lag or to move differently relative to the other parts or segments of the perceived line. This may also be perceived by the subject as if one or more portions of the perceived line were wavy or moved or bulged for a short while or as if one or more of the segments or line portions deviated from the reference pattern (which is a straight segmented line, in the exemplary and non-limiting example of FIG. 3) before assuming again the perceived appearance of the reference pattern. Additionally or alternatively, depending, inter alia, on the nature of the retinal (or choroidal) lesion present, one or more portions or segments of the perceived image of the test pattern (such as, for example, one or more of the segments 229 of the perceived line 322) may appear to temporarily change their apparent brightness (such as becoming brighter or becoming darker), or change their color temporarily as the line moves or jumps, and then return to their originally perceived brightness or originally perceived color, respectively. Additionally or alternatively, one or more of the segments 229 or portions of the test pattern may appear to momentarily or temporarily become blurred or smeared.

Additionally, various different combinations of these differences may also be perceived by the subject. For example one or more of the segments or portions of the test pattern may appear to lag or move differently than the other segments or portions of the pattern and also to change their perceived brightness. Other different combinations of differences may also be perceived by some patients.

For example, when the subject's vision is fixated at the location where the fixation target 228 had previously appeared (represented by the crossed lines 342 in screen 340), a segment 344 of the line 332 may appear to be out of line with other segments in the line 332 or may be otherwise distorted, blurred, shifted or discolored. It is noted that the screen labeled 340 of FIG. 3 represents the screen 112 and the pattern 332 as perceived by the tested subject. In other words, the illustrated line 332 with the shifted segment 344 is shown as perceived by a subject or patient having a retinal or choroidal lesion and not as actually displayed on the screen 112. Thus, while the screen 330 of FIG. 3 schematically represents the image as actually presented to the subject 105 on the screen 112, the screen 340 of FIG. 3 represents the image perceived by a subject having a retinal or choroidal lesion (in the tested eye) after the line 332 of screen 320 is made to disappear (hidden) and the line 332 of screen 330 is presented (or displayed) to the subject at a different location on the screen 112.

Screen 340 (of FIG. 3) illustrates a possible appearance of the line 332 (of screen 330) to an individual having a retinal or choroidal lesion. The perceived line 352 of the perceived screen 340 represents the image of the line 332 presented in screen 330 as it may be perceived by an individual having a retinal or choroidal lesion. The segment 342 of the perceived line 352 may typically be temporarily or transiently perceived as being out of line with other segments in the line 352. This is by way of example only, and other differences between the perceived image and the pre-defined reference pattern may be perceived, such as, but not limited to, one or more segments in the second pattern appearing to the subject as being shifted or wavy or lagging behind, or blurred, or dimming, or smeared, or bent, or otherwise distorted, or discolored. Additionally, one or more of the segments in the second pattern may be perceived by the subject to disappear or to be missing from the second pattern. As the subject subsequently shifts his vision from the fixation target 228 to the presented line 332, the segment 344 in the image of the perceived line 352 may appear to move into alignment with other segments in the line 332 as shown in screen 350. Thus, the line 363 of screen 350 (FIG. 3) schematically represents the perceived image of the line 322 as possibly perceived by the subject having a retinal or choroidal lesion after the subject re-fixates his vision on the line 332. Thus, the segment 344A schematically represents the new perceived position of the previously perceived segment 344 after the patient shifted his eye to refixate on the new position of the line 332. The perceived segment 344A may now be perceived as realigned again with the rest of the perceived segments of the perceived line 363.

Typically, the reason for the presented line 332 being perceived as straight again (as illustrated in the perceived line 363 of screen 350) after the patient refixated his vision at the new position at which the line 332 appeared after the line 322 disappeared from the screen, is that in most cases when the subject shifts his vision from the fixation point 228 to the new location on the screen at which the line 332 appeared, after a certain time (typically a few hundred milliseconds or longer) the "filling-in" phenomenon disclosed hereinabove may occur.

The subject, in step 275, may indicate which, if any, of the segments in the line 332 appeared different or were perceived to behave differently than corresponding segments in the predefined reference pattern. This may be done by the subject bringing the cursor 225 to the segment or segments that appeared to move or to blur or to distort or to disappear, or to otherwise change (the segment 344 in this example) and clicking a button on the mouse 125 or a key on the keyboard 120, or by otherwise performing an action with a pointing device (not shown) or any other suitable input device (such as, but not limited to, any of the input devices disclosed hereinabove and hereinafter). The data representing the location(s) on the screen 112 of the segment or segments in the region pointed to by the subject may thus be stored by the system (step 277) in the memory of the computer system 105, and/or in the memory 145 of the server 140 or by any other suitable storage means, such as but not limited to, a fixed or removable magnetic media storage device (Hard disc drive or floppy disc drive), optical storage device, magneto-optical storage device, holographic storage device or any other suitable storage device known in the art. This stored data may be used to locate and/or report and/or display and/or symbolically represent (in hard copy or otherwise), the region in the subject's retina in which the retinal lesion (or an underlying choroidal lesion) is located, as disclosed in detail hereinafter.

It is noted that the storage device or memory used for storing the test results data may be included in or suitably linked or coupled to the computer system 105 or the computer 110, or the server 140. Alternatively, the storage device may be a shared device which is shared by or accessible to one or more of the computer system 105 or the computer 110, or the server 140, over a communication network. Thus, while the test results data may be stored locally on the system 105, this is not obligatory and the test results may be stored elsewhere as disclosed hereinabove.

In step 280 it is determined whether adequate mapping of the field of vision was achieved. For example, it may be checked whether the number of lines 322 presented to the subject is less than a predetermined number, such as, for example, 40 (or any other suitable predetermined number). If the number of lines 322 presented to the subject is less than the predetermined number, the process may return to step 250 and a new line 322 is presented to the subject. Steps 250 to 280 may be repeated several times, for example 40 times (or any other suitable predetermined number of times suitable for such a test). In each repetition the line 332 may be presented at a different location of the screen 112 until the region of the subject's macular visual field has been appropriately mapped.

It is noted that such mapping may be achieved in more than one way. For example, in accordance with one preferred embodiment of the invention, after the line 332 is presented or displayed to the subject 100, and the subject has finished marking the segments which appeared different than the corresponding segments of the line 322, or alternatively to mark the segments which appeared different than the "virtual" predetermined reference pattern (a straight segmented line mentally conceived by the subject), the subject may visually fixate the tested eye on a fixation target 228A (see screens 330, 340, 350 and 360) in the vicinity of the line 332, by bringing the cursor 225 to point at the fixation target 228A and clicking a button on the mouse 125 to indicate fixation as disclosed in detail hereinabove. This may trigger the repeating of steps 265 and 270 which will result in the disappearing of the line 322 and the showing of a new line (not shown) at a new position on the screen 112 which is different than the position at which the line 332 was previously presented. The subject may then proceed to mark any segments at which a difference was perceived as disclosed hereinabove. The presentation may be similarly continued until adequate mapping of the field of vision has been performed.

Alternatively, in accordance with another embodiment of the present invention, after the line 332 is presented or displayed to the subject 100, and the subject has finished marking the segments which appeared different than the corresponding segments of the line 322, or alternatively to mark the segments which appeared different than the "virtual" predetermined reference pattern (a straight segmented line mentally conceived by the subject), the line 332 may be caused to disappear from the screen 112, and the line 322 and the fixation target 228 may be again presented to the subject 110 in the same positions illustrated in screen 320. The subject may then again fixate on the fixation target 228 by bringing the cursor 225 to point at the fixation target 228 and click the mouse 125 to indicate fixation. The computer 100 may then present a new test pattern (not shown) at another new position relative to the position of the line 322 and the process may repeat after the subject marked any segments for which a difference was observed. By randomly or pseudo-randomly selecting a new line position for each new repetition the process may thus achieve adequate mapping of the desired macular area.

It is noted that if the first test pattern (such as for example the straight segmented line 322) which is presented to the subject happens to be projected on a region of the retina which is lesioned (at the retinal or the choroidal level), the subject 100 may initially perceive the pattern to be distorted or modified but after a certain time the test pattern may be perceived to be identical with the predetermined reference pattern (such as for example a straight non-distorted segmented line due to the "filling in" phenomenon disclosed hereinabove. In such a case, the subject 100 may indicate or mark the location of the initially perceived distorted or modified region or component of the first test pattern, by using the mouse 125 and the cursor 225 as disclosed hereinabove.

Alternatively, the subject 100 may be instructed (before or during the test) to ignore the initially perceived distortion or modification and to proceed to perform the fixation on the fixation target 228 as disclosed hereinabove by bringing the cursor 225 to point at the fixation target 228 and clicking a button on the mouse 125. When the second test pattern, such as the line 332 is then presented at another location on the screen 112 (see screen 330 of FIG. 3), the subject 100 may temporarily perceive a modification or distortion as the subject 100 shifts his vision from the fixation target towards the location of newly presented test pattern (which in this example is the location of the line 332 of screen 330 of FIG. 3). Therefore, in such cases in which the image of the first test pattern falls on a lesioned retinal area, the subject may perceive a distortion or modification in each of the repetitions or iterations of the test, irrespective of the location at which the second test pattern is presented on the screen 112. The distortion will be perceived after the patient shifted his vision from the fixation target towards the test pattern presented at the new location due to the fact that the shifting causes the image of the newly presented test pattern to be projected on the lesioned retinal area. Because of this phenomenon, the subject may mark a distortion or modification on all the second test pattern repetitions, and all of the marked distortions will tend to be marked at positions along the test pattern which approximately correspond to the position of the distortion or modification which was initially perceived at the first time of presentation of the first test pattern due to the presence of the retinal lesion (or of a choroidal lesion).

It is noted that if the test results do exhibit such an approximate "alignment" of multiple markings of perceived distortions or modifications at approximately similar positions on the test pattern, irrespective of the location of the presented second test patterns, this may be taken as an indication that there is at least one suspected retinal (or choroidal) lesion at a position in the retina on which the image of first test pattern was projected.

It is further noted that while the presence of a retinal lesion may be detected in the above case, it may be advisable to test the same eye of subjects exhibiting such a spurious marking "alignment" using the "flash test" embodiment of the invention as disclosed in detail hereinafter, since this test does not show this spurious marking "alignment" phenomenon.

It is noted that while it is possible to perform the testing by mapping the field of view of the patient using only horizontal line patterns (such as the line 322) and moving the horizontal line patterns vertically to different positions on the screen 112, the mapping may also be performed using vertical lines (not shown in FIG. 3) which may be moved horizontally to different positions on the screen 112. It may also be possible to use a plurality of orthogonal horizontal and vertical lines in the same mapping test, in which case the mapping coverage of the field of vision may resemble a grid of intersecting lines (not shown).

Furthermore, the mapping of the field of view may also be done using a series of lines that are inclined at an angle to the horizontal or vertical orientation (slanted lines), or combination of series of slanted lines which may intersect each other either orthogonally or non-orthogonally, such that if these lines were all displayed at the same time on the screen 112 they may form a grid of intersecting lines (not shown).

It is noted that in step 280 it is checked whether adequate mapping of the field of vision of the tested eye has been achieved. For example, if the location of presentation of the test pattern is different at each repetition or iteration of the test, adequate mapping may be ensured by checking that the number of lines presented to the subject has reached a predetermined number of iterations ensuring that data has been collected which suitably covers or maps the entire field of vision at a desired resolution.

Other different methods may however also be used to check adequate mapping. For example, if the testing of each location needs to be repeated more than one time and the location of presentation of test patterns is randomly or pseudo-randomly selected, the locations of performed tests may be compared with a look-up table to verify that the desired number of test repetitions for each test pattern location has been performed. If adequate mapping has not been achieved the process may return control to step 250 to present the next test pattern.

If adequate mapping of the field of vision of an eye has been achieved, the process may proceed by determining whether only one eye has been examined so far (step 282). If only one eye has been examined, the subject may be instructed to uncover the non-examined eye and to cover the examined eye (285). The process may then return to step 250 with the subject testing his other eye as disclosed in detail hereinabove. If both eyes have been examined, the process may terminate (step 290).

The position of the line 322 presented or displayed to the subject on the screen 112 may thus be varied in order to appropriately cover the macular area at a desired resolution so as to detect lesioned retinal regions. It is noted that in accordance with one preferred embodiment of the invention, the mapping may be performed more than once, and that the central part or foveal region of the macular area of the retina may also be mapped at a higher resolution than the rest of the macular area. This may be accomplished by presenting to the subject test patterns such as the line 322 at locations which are relatively close to one another on the screen 112. This may result in higher lesion mapping resolution in the foveal region. In addition, more test patterns may be presented in areas in the mapped visual field, where there are defects, than in other areas in the mapped visual field.

Figure 4A:
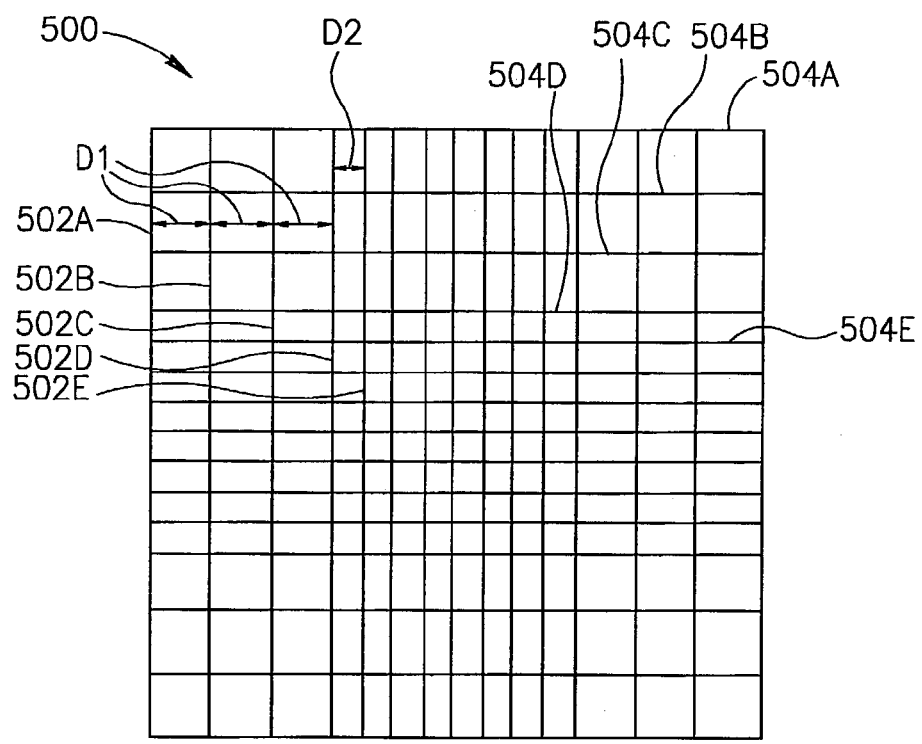
FIGS. 4A–4B are schematic diagrams illustrating some exemplary types of line series which may be useful for mapping retinal and/or choroidal lesions in accordance with some exemplary embodiments of the present invention.
Figure 4B:
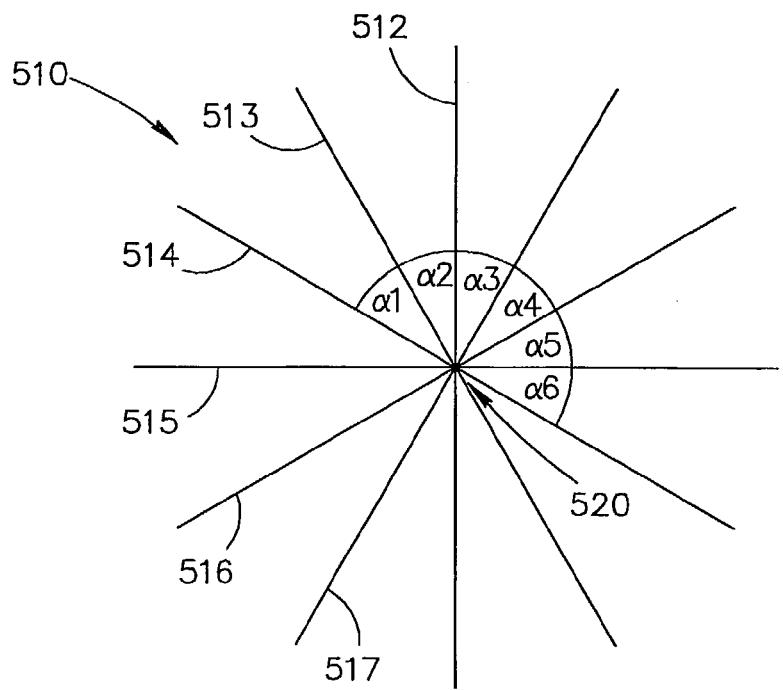

Reference is now made to FIGS. 4A–4B which are schematic diagrams illustrating some exemplary types of line series which may be useful for mapping retinal lesions in accordance with some exemplary embodiments of the present invention.

FIG. 4A schematically represents a mapping grid which may be formed if all the linear test patterns used in the test were to be simultaneously presented on the screen 112. The grid 500 thus formed may include parallel vertical lines, such as for example the vertical lines 502A, 502B, 502C, 502D, and 502E and parallel horizontal lines, such as for example the vertical lines 504A, 504B, 504C, 504D, and 504E. It is noted that the horizontal lines need not be equally spaced from each other. For example while the line pairs 502A and 502B, 502B and 502C, and 502C and 502D may be separated from each other by a cone angle D1, the line pairs 502D and 502E may separated from each other by a cone angle D2. Preferably D1 is larger than D2, such that the density of grid lines at the central region of the grid 500 is higher than the density of the lines at more peripheral regions of the grid 500. This may enable mapping of the central foveal region at a higher mapping resolution than the mapping of more peripheral foveal regions.

It is noted however, that the horizontal and vertical lines of the grid 500 may also be equally spaced from each other or may be arranged differently than the arrangement of the lines illustrated in FIG. 4A. Furthermore, it is noted that while the lines of the grid 500 may be contiguous lines as shown in FIG. 4A (for the sake of clarity of illustration), the lines of the grid 500 may also be segmented lines (not shown) or dotted lines (not shown) or the like. Orthogonal or non-orthogonal slanted lines may also be used (not shown) to map the retinal visual field.

The grid used for mapping may also include only the horizontal lines shown in grid 500 or only the vertical lines of grid 500. Furthermore, it is noted that the number and the density of the lines shown in FIG. 4A is only shown by way of example and the number of the lines as well as the separation between the lines may be modified or changed depending, inter alia, on the required retinal mapping resolution.

FIG. 4B schematically represents a mapping grid 510 which may be formed if all the linear test patterns used in the test were to be simultaneously presented on the screen 112. The grid 510 thus formed may include a plurality of lines 512–517 which intersect at a point. While the lines 512–517 are illustrated as having identical lengths, their lengths may also vary. The angles α1, α2, α3, α4, α5, and α6 may be identical to each other and may be all equal to 60°. It is noted, however, that the number of lines in the grid and the angle at which each line is inclined relative to the horizontal line 515 may vary and may be different than the values illustrated in FIG. 4B. Additionally, the number of the lines may vary such that the grid may include more or less than the six lines 512–517. While the lines 512–517 are illustrated as contiguous (for the sake of clarity of illustration), the lines may also be segmented or dotted lines, or the like.

It is furthermore noted that many variations and permutations of the test patterns of the invention are possible and are all considered to be within the scope and spirit of the present invention. Similarly, the number of the test patterns forming the mapping grid may vary as may their separation from each other, their angular inclination within the mapping grid.

It will be apparent to those skilled in the art that the exemplary mapping grids 500 and 510 do not represent the form or shape of a single test pattern, but are rather virtual representations of the images that would result if all the test patterns of exemplary possible tests were to be projected simultaneously on a surface.

In accordance with another embodiment of the invention, it is also possible to present to the subject test patterns which include a distortion or other modification of the predefined reference pattern. For example, while the line 332 of screen 330 of FIG. 3 comprises segments which are all arranged or aligned in a straight line, a line 362 actually having a displaced segment 364 may also be presented to the subject on the screen 112 as illustrated in screen 360 of FIG. 3.

The displaced segment 364 may be transiently presented at it's displaced position, for example, for a duration of up to about 300 milliseconds, after which the displaced segment 364 may be realigned with the other segments of the line 362, but other different suitable presentation duration time values may also be used.

It is noted that while in accordance with one embodiment of the present invention, the displaced segment 364 may remain displaced for the entire duration of presentation of the line 362, preferably, the segment 364 is only transiently displaced as shown and is then realigned with the remaining segments of the line 362 for the remaining part of the presentation of the line 362. This method of presentation may better mimic the characteristics of the image perceived by patients which have a retinal or choroidal lesion when a segmented line similar to the segmented line 322 is projected on a region having a retinal or choroidal choroidal lesion as disclosed in detail hereinabove.

Generally, test patterns, such as for example the line 362 of screen 360 (FIG. 3) may be regarded as test patterns which include an intentionally introduced distortion which may be similar to distortions which may be seen or perceived by a patient having a retinal or choroidal lesion when a non-distorted test pattern (such as, but not limited to the line 332 of screen 330) is presented to the patient. Such test patterns including a distortion may also be referred to hereinafter as "artificially distorted" test patterns. The presentation of such artificially distorted test patterns may be used, inter alia, to ascertain that the subject is aware of the visual distortion associated with a retinal or choroidal lesion, and that his responses reliably reflect the perceived appearance of lines presented to him.

It is noted that while in the exemplary artificially distorted line 362 illustrated in screen 360 of FIG. 3 only one segment 364 is shifted or displaced relative to the other segments of the line 362, various other different types of distortions may be used. In accordance with other exemplary embodiments of the invention such distortions may include, but are not limited to, displacing or misaligning more than one segment relative to the rest of the segments (not shown) of the line 362, transiently or briefly displacing or misaligning one or more segments relative to the rest of the segments within part of the duration of presentation of the line 362, tilting or changing the orientation of one or more segments relative to the orientation of the remaining segments (not shown), bending or otherwise changing the shape of one or more segments, removing one or more of the segments (not shown), blurring one or more of the segments (not shown), changing the hue or color or brightness of one or more segments of the test pattern (not shown), or introducing other types of alterations to the test pattern which may resemble distortions or alterations which may be perceived by a person having a retinal lesion when such a person is presented with a non-distorted test pattern or reference pattern, such and other changes or distortions or modifications of the test pattern may, preferably, be transient changes but similar non-transient changes may also be used.

It is noted that if the test patterns used in the test are non-segmented, such as for example if the test pattern comprises a contiguous (non-segmented) straight line (not shown), the artificially distorted test patterns may include, but are not limited to, bending one or more portions of the contiguous line such that these portions are not straight (for example, such distorted portions of the test pattern may be curved or wavy), blurring or smearing one or more portions of the test pattern (not shown), hiding (not presenting) one or more portions or parts of the test pattern (not shown) or changing the hue or color or brightness of one or more portions of the test pattern, or the like. Other suitable visually perceivable types of distortions or alterations of test patterns may also be used.

The presentation of such artificially distorted or otherwise intentionally altered or modified test patterns to the patient or test subject may also be advantageously used to detect cases in which the patient is not paying attention to the test patterns due to fatigue or due to any other reason. This may enable the assessment of the degree of reliability of the test result. For example, if the patient does not reliably and/or accurately report the presence of the distortion or alteration in such artificially distorted or otherwise altered test patterns presented to him during the testing, this may be taken as an indication of a problem and may indicate a possible need to repeat the test or alternatively to label the test results as unreliable. Additionally, the degree of correlation between the location of the distortion or alteration on the presented test pattern and the location of the distortion or alteration perceived and marked (or reported) by the patient may be used to assess the accuracy of perceiving and/or of the reporting of the location of the distortion or alteration by the patient or tested subject.

It is noted that in the exemplary screen 320 of FIG. 3, the segmented line 322 may be regarded as a pre-determined "reference pattern" of the test. The patient may be asked and/or trained to relate to the perceived image of the presented straight segmented line 322 as the reference pattern against which to compare the perceived images of the later presented test patterns. When the test is first presented to a patient, the patient may be told by the trainer or the individual administering the test that he is about to be shown a straight segmented line (or any other reference test pattern which is being used for the test). In this way, the patient becomes aware of the reference pattern against which he is expected to compare the perceived images of the test patterns which are going to be presented to him as the testing proceeds. It is noted that the patient may also be told before the testing begins that he is to be presented with straight segmented lines (without initially presenting to him such a line) and asked to compare the perceived image of each of the lines presented to him with a reference pattern which is a straight segmented line.

It is noted that the testing method of the present invention is not limited to the "moving pattern" testing method disclosed hereinabove, and may be modified in different ways, which are considered to be within the scope of the present invention.

"Flash Test" Method

In this embodiment of the invention, a fixation target is presented to the tested individual on a display device, such as but not limited to the screen 112 of the display device 115 (FIG. 1). After the tested patient has fixated on the fixation target, a test pattern is briefly presented (flashed) at a first location on the display device for a time duration which is sufficient to allow the patient to perceive an image of the presented test pattern. The image perceived by the patient in also referred to as a "perceived image" of the test pattern. The patient may then be requested to indicate whether he or she detected a difference between the perceived image of the presented test pattern and a reference pattern.

The tested patient may be informed by the trainer, or ophtalmologist or the person delivering the test, before the test is performed, that he is going to be presented with patterns similar to or different than a reference pattern. The patient may or may not be actually presented with the reference pattern before the test begins. For example, if the reference pattern is a straight segmented line, the patient may be verbally told that he is going to be presented with a variety of test patterns that may be similar to or may be different from a straight segmented line, without showing the patient a straight segmented line (which is the reference pattern in this non-limiting exemplary test) prior to the presentation of the actual test patterns to the patient. In such a case, the reference pattern is based on the prior acquaintance of the patient with the reference pattern which is used. In other words, previous knowledge of the patient of how a straight segmented line looks is relied upon.

It is also possible (though not obligatory), however, to present the reference pattern to the patient before the actual test patterns are presented, in order to give the patient an idea of how the reference pattern is supposed to look. While this may help the patient to understand and familiarize himself or herself with the form of the reference pattern, it is not a necessary part of the test, since most patients may adequately perform the test just by being told verbally what the reference pattern is, without being presented with the actual reference pattern prior to the presentation of the test patterns.

After the patient is presented with a test pattern, if a difference was detected by the patient between the pattern perceived by the patient as a result of the presentation of the test pattern and the reference pattern, the patient may indicate the region or regions or segments or components of the perceived pattern at which a difference or differences were noticed. The presence and the location of the difference(s) which are detected and indicated by the patient may be stored for further processing and analysis as disclosed hereinabove. This procedure may be repeated several times while changing the location of the test pattern relative to the fixation target on the screen 112. The number of repetitions and the location of the presented test patterns are such that a suitable area of the visual field of the tested eye of the patient is mapped for detection of possible retinal lesions or pathologies.

Reference is now made to FIGS. 5A–5J which are schematic diagrams illustrating the patterns displayed on the screen 112 of the subject's display device 115 at various different exemplary steps of another embodiment of an eye test performed by the system illustrated in FIG. 1, and the possible appearance of the test patterns as they may be perceived by the test subject at some exemplary steps of the eye test.

In performing the flash test, the patient or test subject may be positioned before the screen 112, with the distance of the tested eye being preferably approximately 50 centimeters from the screen 112. Other different distances may however also be used depending, inter alia, on the dimensions of the screen 112, and on the size of the displayed test patterns.

The "flash test" method may begin by presenting to the patient or test subject one or more log-on screens, such as, but not limited to, the screen 300 schematically illustrated in FIG. 3. Other additional screens (not shown) may also be presented for entering other patient demographic data or the like. Once the patient identity has been established, screen 370 (FIG. 5A) may be presented to the patient.

A fixation target 372 is displayed on the screen 112. The fixation target 372 may be a circular pattern or may be any other suitably shaped pattern as disclosed in detail hereinabove for the fixation target 228 of FIG. 3. A cursor 373 may also be displayed on the screen 370. If the patient is trained to take the test, the trainer or test supervisor may explain to the patient that he or she should cover one eye (by hand or by using a suitable eye occluding device or patch), look at the screen 370 with the non-covered eye, and bring the cursor 373 to point at the fixation target 372.

Preferably, but not obligatorily, the movement of the cursor 373 may be restricted to the horizontal direction. For example, in accordance with one possible implementation of the method, the tip of the arrowhead-like pointing part 373A of the cursor 373 may be pointed upwards and it's movement may be restricted along an imaginary non-visible horizontal line (not shown) intersecting the fixation target 372. The patient may bring the cursor 373 to point at the fixation target 372 by using a mouse or any other suitable pointing device, as disclosed in detail hereinabove for the moving line method.

Similar to the fixation target 228 of FIG. 3, the fixation target 372 may be sized so that it is large enough to be seen by the patient or test subject but small enough so that bringing the cursor 373 to the fixation target 372 is a demanding task for the test subject. This causes the subject to fixate his vision on the fixation target 372. Upon bringing the cursor 373 to the fixation target 372, the subject may provide a suitable indication that he has positioned the cursor 373 to point at the fixation target 372. For example, the patient or test subject may provide the indication by clicking on a button of the mouse 125 or by depressing a predetermined key on the keyboard 120 (or by suitably using any other suitable pointing device known in the art or disclosed hereinabove). This patient input may serve as an indication or verification that visual fixation on the fixation target 372 has been achieved.

Figure 5A:
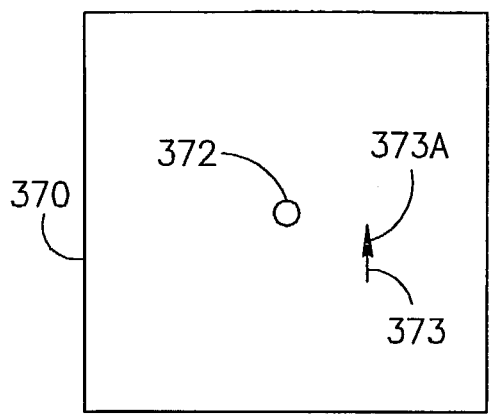
FIGS. 5A–5J are schematic diagrams illustrating patterns displayed at various different exemplary steps of another embodiment of an eye test performed by the system illustrated in FIG. 1, and the possible appearance of the test patterns as they may be perceived by the test subject at some exemplary steps of the eye test.
Figure 5B:
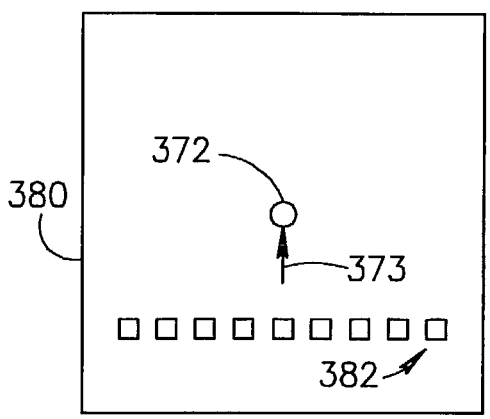

After the patient indicates fixation as disclosed hereinabove, a test pattern in the form of a segmented straight line 382 is presented to the patient (see screen 380 of FIG. 5B). It is noted that while the exemplary test pattern illustrated in FIG. 5B is a segmented straight line 382 as disclosed hereinabove for the moving line test method, other types of different test patterns (not shown) may however also be used. The segmented straight line 382 may be presented on the screen 112 immediately after the patient clicks the mouse 125 or may be presented after a delay. If a delay is used, the duration of the delay may preferably be in the range of approximately 0–200 milliseconds, but other higher values of the duration of the delay may also be used. The segmented straight line 382 may be displayed on the screen 112 for a short duration. Preferably, the duration of presentation of the test pattern (the line 382) on the screen 112 may be in the range of approximately 100–160 milliseconds. It was practically found that most patients perform the test well with the test pattern presentation duration in this range which enables to keep the duration of a test in the approximate range of 2–3 minutes (for a typical test including the presentation of 23 vertical segmented lines and 23 horizontal segmented lines).

It is noted that duration of presentation may also be shorter or longer. Typically, a duration of approximately 10–20 milliseconds may be on the threshold of observation for most patients. Thus, presentation duration values which are longer than 10–20 milliseconds may have to be used for most patients. The threshold of observation may, however, vary, inter alia, with the patient's age, visual acuity, or the like.

It is also noted that the test pattern presentation duration may also be longer than 160 milliseconds, but this may increase the overall test duration.

One advantage of the relatively short duration of the presentation of the test pattern (also referred to herein as "flashing" of the test pattern) may be that the eye/brain system of the patient may not have enough time to "fill-in" the distorted or missing or different parts of the perceived image of the test pattern, as it may do when the test pattern is static or is presented for a relatively long period of time. This may advantageously reduce or prevent such "filing-in" phenomena disclosed in detail hereinabove, which may decrease the probability of the patient not observing or not detecting (and therefore not reporting) a difference in the appearance of the perceived test pattern (as may often occur in the use of the Amsler test).

It may be further explained to the patient (either before performing the test or while the test is being taken) that he is going to be presented with test patterns on the screen 112. The patient may, for example, be told that the presented test patterns are going to be segmented straight lines, and that the reference pattern against which he is to compare what he actually perceives on the screen 112 is a segmented straight line.

The patient may further be instructed that if he or she detects any difference between the perceived form of the presented test pattern or of one or more parts or portions thereof and the reference pattern (which is a straight segmented line in the non-limiting example illustrated in FIGS. 5A–5J), he or she is requested to indicate the approximate location of the part or parts which were perceived to differ from the reference pattern, as is disclosed in detail hereinafter.

For example, it may be explained to the patient that one or more of the segments of the straight line may deviate from linearity or may appear to move, or may appear wavy, or may appear to bulge or to deviate or to be distorted such that they are not perceived to be arranged as a straight line, and that other differences may also be observed such as, for example, a movement of one or more segments or parts of the perceived image of the test pattern relative to other parts or segments or portions of the perceived test pattern, or a dimming or brightening of some segments relative to the rest of the segments, or a change in the hue or color of some segments relative to the hue or color of other segments, or a fuzziness or blurring of one or more segments relative to the other segments, or that one or more segments or portions of the segmented straight line may appear to be missing, and that other differences may also be perceived.

Figure 5C:
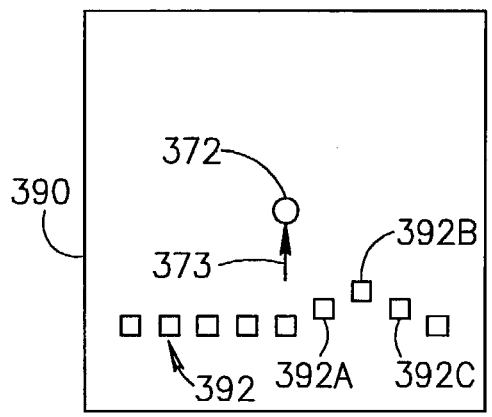

FIG. 5C schematically illustrates a screen 390 which is a representation of how the presented screen 380 (FIG. 5B) may be perceived by a patient having a retinal lesion while the patient's tested eye is fixated on the fixation target 372. The perceived image perceived by the patient may be a distorted segmented line 392 (FIG. 5C). In the perceived distorted line 392, the segments 392A, 392B, and 392C are perceived as shifted or distorted, or moving, or forming a bulge such that they are not arranged in a straight line. This may be due to the presence of a retinal lesion.

Figure 5D:
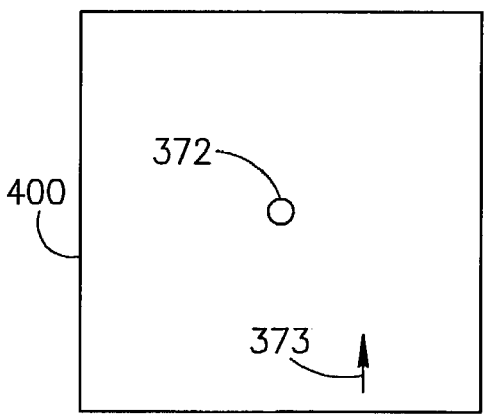
Figure 5E:
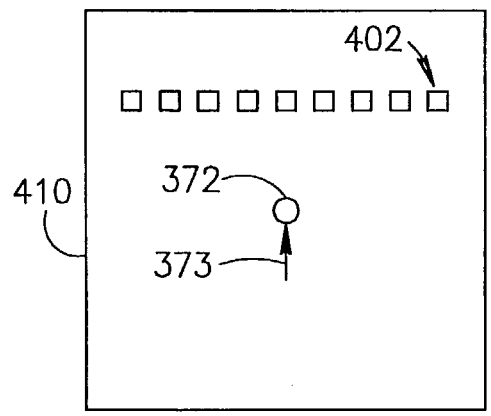

After the presentation of the test pattern is terminated, the test pattern 382 disappears from the screen 112 by terminating the displaying thereof on the screen 112. The patient may then indicate or mark the approximate location of the perceived region of difference or distortion on the perceived image. This marking or indicating may be performed, for example by the patient using the mouse 125 to move the cursor 373 to the region of the screen 112 where the difference was observed or detected. FIG. 5D illustrates the appearance of a screen 400 after the patient moved the cursor 373 to the approximate position on the screen at which the patient observed the distortion in the perceived image illustrated in FIG. 5C. This position roughly matches the region where the segments 392A, 392B, and 392C (of FIG. 5C) were perceived by the patient as shifted or distorted. After the positioning of the cursor 373 at the approximate position at which the difference or distortion was observed the patient may click a button on the mouse 125. The computer system 105 may thus determine from the position of the cursor 373 in screen 400 (FIG. 5D) the location on the test pattern at which a difference or distortion was observed or detected by the patient in the perceived image 392 of the test pattern 382 which was presented in screen 380 (of FIG. 5B). This location may be stored as data in the computer system 105.

It is noted that while in screens 370 and 380 (of FIGS. 5A and 5B, respectively) the movement of the tip 373A of the arrowhead-like cursor 373 was restricted along an imaginary, non-visible, horizontal line (not shown) intersecting the fixation target 372, after the termination of the presentation of the test pattern 382, the cursor is preferably not restricted and may be moved to any point on the screen 400. Alternatively, the moving of the cursor 373 may remain vertically restricted as disclosed hereinabove, in which case the patient may mark the location of the observed distortion or difference by moving the cursor 373 horizontally (not shown) until it reaches a location which is above or below the region at which the difference or distortion was observed on the perceived test pattern, (depending on whether the location of the appearance of the test pattern was below or above the fixation target 372, respectively).

The computer system 105 may thus store data representative of the location (or locations) marked by the patient. In accordance with one exemplary embodiment of the invention, the data may include the position of the test pattern 382 on the screen 380 and the position on the test pattern 382 which is equivalent to the horizontal position marked by the cursor 373 on the screen 400 (which is indicative of the location which was marked by the patient as the approximate region of the distortion perceived by the patient). Other different methods of storing the data may also be used as may be apparent to those skilled in the art.

It is noted that the computer 105 may also store other information or data associated with the presented test pattern. For example, the stored data may include, but is not limited to, the number of the test pattern (which may be indicative of the order of presentation of the particular test pattern within the test), the orientation of the test pattern (for example, vertical or horizontal, or the like), or any other data related to other parameters of the test pattern.

After the marked position of the distortion is stored, the patient may initiate the presentation of a new test pattern by repositioning the cursor 373 to point at the fixation target 372 and clicking a button on the mouse 125 as disclosed for screen 380 (of FIG. 5B) to indicate the achieving of fixation. This may cause the presentation of a new test pattern 402 as illustrated in the screen 410 of FIG. 5E. In this exemplary screen, the test pattern 402 is briefly presented at a new location on screen 410, different than the location of the test pattern 382 on screen 380 (FIG. 5B). The patient may perceive the presented test pattern 402 as a segmented straight line with no distortion (or no difference from the reference pattern) if there is no retinal lesion in the retinal region on which the image of the test pattern 402 is projected when the patient maintains visual fixates on the fixation target 372. The patient does not mark any position on the screen 410 since no distortion or difference from the reference pattern were observed by the patient. The patient may then proceed by visually fixating on the fixation target 372 and clicking on the mouse 125 to initiate the presenting of a new test pattern (not shown).

It is noted that in accordance with one embodiment of the invention, the cursor 373 may be automatically shifted to a new position away from the fixation target 372 following the termination of the presentation of the test pattern. This may be advantageous since it may force the patient to bring the cursor 373 again to point at the fixation target 372 which may ensure proper visual fixation before the presentation of each new test pattern. This however is not mandatory, because it may be possible to train the patient to perform visual fixation on the fixation target 372 prior to clicking the mouse to initiate the presentation of an additional test pattern, and because it may also be possible to independently monitor patient fixation by the presentation of artificially distorted test pattern as disclosed hereinabove and hereinafter.

In accordance with one embodiment of the invention, after a sufficient number of test patterns at appropriate locations have been presented to the patient to adequately map the desired field of vision with a desired resolution, the test may be terminated. In accordance with another embodiment of the invention, the test may further continue by changing the orientation of the presented test patterns such that a new sequence of test patterns is presented to the patient which test patterns are vertically oriented segmented straight line.

Figure 5F:
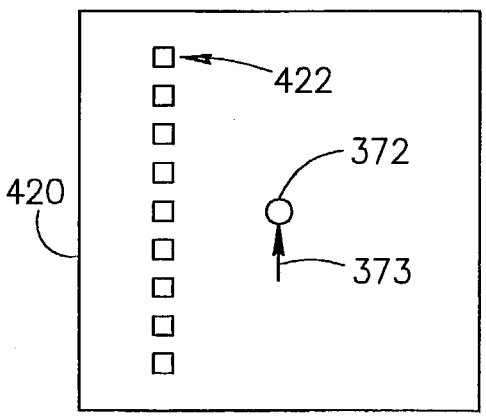

In screen 420 of FIG. 5F a vertically oriented test pattern 422 is illustrated. Preferably, but not necessarily, the shape, length and number of segments of the vertically oriented test pattern 422 may be similar to the shape, length and number of segments of the horizontally oriented test patterns previously presented to the patient (such as, for example, the horizontally oriented test pattern 382 of FIG. 5B). This, however is not mandatory, and the shape, or the length or the number of segments of the vertically oriented test patterns may be different than those of the horizontally oriented test patterns.

If the patient noticed no difference or distortion in the perceived pattern (not shown) of the test pattern 422 presented to the patient, the patient may re-fixate on the fixation target 372, and indicate visual fixation by clicking the mouse 125 to cause the presentation of a new (vertically oriented) test pattern.

Figure 5G:
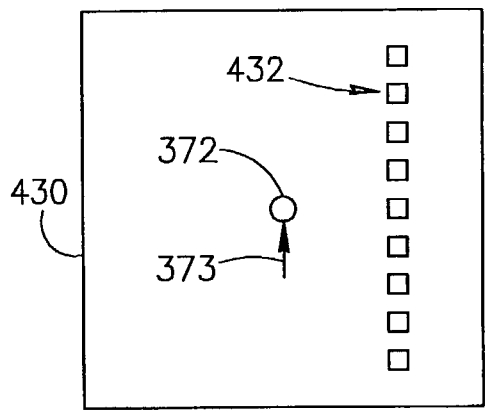

FIG. 5G illustrates an exemplary (vertically oriented) test pattern presented to the patient during a part of the test. The test pattern 432 is presented in a location of screen 430 as illustrated in FIG. 5G.

Figure 5H:
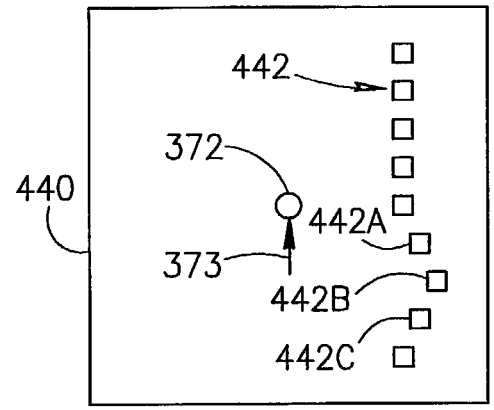

FIG. 5H schematically illustrates a screen 440 which is a representation of how the presented screen 430 (of FIG. 5G) may be perceived by the patient having a retinal lesion while the patient's tested eye is fixated on the fixation target 372. The perceived image perceived by the patient may be a distorted segmented line 442 (FIG. 5H). In the perceived distorted line 442, the segments 442A, 442B, and 442C are perceived as shifted or distorted, or forming a bulge such that they are not arranged in a straight line. This perceived distortion may possibly be due to the presence of the same retinal lesion which caused the distortion in the perceived image 392 (FIG. 5C) of the presented test pattern 382 of FIG. 5B. The distortion in the perceived image 442 may however also be due to the presence of another different retinal lesion.

Figure 5I:
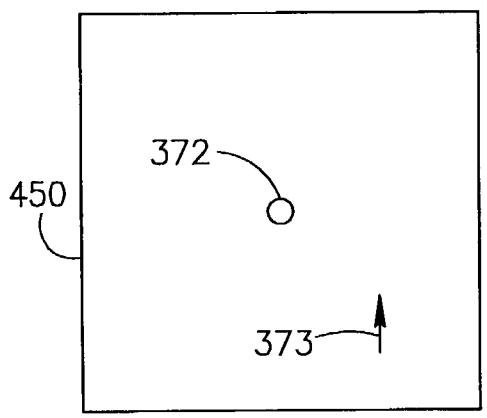

After the termination of the presentation of the test pattern 432 (FIG. 5G), the patient may mark the location of the perceived distortion as illustrated in screen 450 of FIG. 5I by moving the cursor 373 to point at the approximate location of the distortion and clicking the mouse 125 which stores data representing the location of the observed distortion in the computer system 105, as disclosed hereinabove. Additional vertical test patterns at different locations may then be presented to the patient until the mapping of the retina using vertically oriented test patterns is completed at a desired resolution. Testing of the second eye of the patient may then be also performed by covering or occluding the already tested eye of the patient and repeating the same testing procedure for the uncovered non-tested eye.

The Use of "Artificial Distortions" in the Flash Test Method

Preferably, in accordance with an embodiment of the invention, it may be possible to include intentional distortions in the test patterns presented in the flash test method disclosed hereinabove by presenting the patient with artificially distorted test patterns. The artificially distorted patterns may include, inter alia, any of the types of distortions included in the artificially distorted test patterns disclosed hereinabove for the "moving line" test method (for one, non-limiting example of such an artificial distortion see screen 360 of FIG. 3). Thus, some of the test patterns presented to the patient may be artificially distorted, as disclosed hereinabove. For example, one out of three (approximately 30%) test patterns presented to the patient may be an artificially distorted pattern. Other different ratios of artificially distorted to non-distorted test patterns may also be used, as well as tests in which all test patterns include artificial distortions.

Among the advantages of presenting artificially distorted test patterns is, that this may train the patient in what may be the appearance of a perceived distortion if a retinal lesion is present. This training may improve the patient's ability to detect and report such distortions if such a distortion or similar distortions appear in the perceived image following the presentation of a non-distorted test pattern to the patient.

Another advantage, as explained hereinabove, may be the possibility to assess the degree of attention of the patient, and the reliability of the test results. Thus, if the patient fails to reliably report the presence and the location of the distortions displayed in the artificially distorted test patterns, this may be used as an indication of possible lack of attention of the patient, due to fatigue or other reasons, or this may also be used as an indication that something is wrong with the test presentation or with the test results, or with the patient's ability to visually perceive the test patterns, in which case the test results may be ignored (such as, for example, when the test is performed by the patient alone without the supervision of a trainer or supervisor). If a trainer or supervisor is present near the patient and such a testing non-reliability is reported, for example by an appropriate error message (not shown) appearing on the screen 112 or otherwise, the supervisor or trainer may stop the test (and may cancel the record of the test results if appropriate) and may try to find and rectify the reasons for the patient's failing to reliably report the presence and location of the distortions.

For example, the trainer or supervisor may check if the patient's tested eye is positioned at the appropriate distance from the screen 112, or if the patient is fatigued or not paying attention to the test patterns or not properly fixating his vision at the fixation target 373, or the like. Such problems may be thus rectified and another test may be initiated if desired.

Figure 5J:
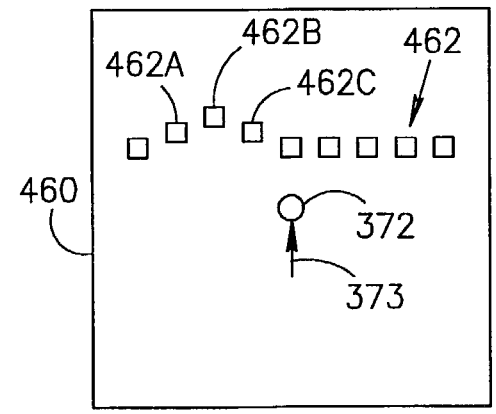

FIG. 5J illustrates one possible form of an artificially distorted test pattern which may be possibly used in the example of the flash testing method illustrated in FIGS. 5A–5I. In screen 460 of FIG. 5J an artificially distorted line 462 is illustrated as presented to the patient on the screen 112. The segments 462A, 462B and 462C of the presented line 462 are positioned and oriented such that they are not aligned (or mis-aligned) with the remaining segments of the test pattern 462. In other words, while the remaining segments of the test pattern 462 are aligned to form a straight line, the segments 462A, 462B and 462C form a bulge or curved part or wavy part of the test pattern 462. The test pattern 462 (which may be presented on the screen 112 of the display device 115) is thus an artificially intentionally distorted test pattern. Thus, when the artificially distorted test pattern 462 is presented to the patient who is visually fixated on the fixation target 373, the patient may perceive the distortion as a deviation of the segments 462A, 462B and 462C from the expected reference pattern of a straight segmented line.

The patient may then proceed to indicate or mark the approximate location of the perceived distortion by bringing the cursor 373 to the approximate location of the perceived distortion and clicking the mouse 125 as disclosed in detail hereinabove. For example, the patient may position the cursor 373 at the approximate position on the screen 112 at which the patient perceived the image of the segment 462B while the test pattern 462 was presented (flashed) on the display device 115, and may click on the mouse 125 to input and store the approximate location of the perceived distortion in the test pattern 462. The location reported by the patient may be compared to the known location of the distortion in the presented artificially distorted test pattern 462.

It is noted that when the patient marks the location of the perceived distortion, an error or inaccuracy in localization may occur along a single dimension only (the horizontal dimension for horizontal test pattern, or the vertical dimension for vertical test pattern), since the location of the presented test pattern is known to the system.

It is also noted that if the patient detects or observes two or more spatially distinct distortions or abnormalities along the presented test pattern, the patient may mark the approximate location of all such detected distortions or visual abnormalities by suitably bringing the cursor 373 to the location at which the additional distortion or visual abnormality was observed and clicking the mouse 125. Thus, the data stored for a test pattern may include the location on the test pattern of more than one detected distortion or visual abnormality.

Typically (but not necessarily), about a third (approximately 30%) of the test patterns presented to the patient may be artificially distorted test patterns. The percentage of the artificially distorted test pattern out of all the test patterns presented to the patient may however vary, depending, inter alia, on previous knowledge of the test performance of the same patient in past tests, or on other considerations. Thus, in some tests, all the test patterns may be artificially distorted.

It is noted that the tests of the present invention may be performed such that only a certain percentage of the test pattern include an AD, or, alternatively, the tests may be performed such that all the test patterns in the test include an AD.

Additionally, the artificially distorted test patterns may be randomly or pseudo-randomly distributed among the rest of the test patterns during a test so that the patient cannot predict the time of presentation of the artificially distorted test patterns by learning the sequence of presentation of these signals.

It is noted that generally vertically oriented artificially distorted test patterns (not shown) may also be presented to the patient (the word "generally" refers to the vertical orientation of the majority of the non-distorted segments which are aligned along an imaginary straight line, even if some of the segments may be horizontally displaced in the region of the artificial distortion).

Typically, the location of the distorted portion or segments on the artificially distorted test pattern may be randomly or pseudo-randomly changed or altered in different presentations of artificially distorted test patterns performed within a test. Such random alteration of the location of the artificial distortion along the test pattern is advantageous because it makes it more difficult for a patient to cheat (either intentionally or non-intentionally) in comparison with a situation in which the distortion is always presented at a fixed location on the test pattern.

If the patient fails to reliably identify and report the presence and the location of the distortion presented in a predetermined percentage of the artificially distorted test patterns which were presented to the patient in a test, the test results may be ignored or discarded as unreliable. For example, in accordance with one non-limiting exemplary embodiment of the method of the present invention, if the patient did not report reliably the presence and the location of the artificial distortion (or another test pattern modification used in the test) in 20% of the total number of artificially distorted test patterns presented within a test, the test results may be ignored or discarded as unreliable.

Thus, in accordance with such an exemplary (non-limiting) test reliability criterion, if in a test the patient was presented with 60 test patterns, and 20 test patterns out of the 60 test patterns were artificially distorted (or otherwise modified) test patterns, the patient has to reliably report the presence and location of the artificial distortion (or of any other test pattern modification which was used in the modified test pattern) in at least four out of the twenty presented artificially distorted test patterns in order for the test results to satisfy the reliability criterion.

It is noted that in accordance with the exemplary embodiment of the reliability criterion disclosed hereinabove, it is not enough for the patient to just identify the presence of the distortion or modification which was artificially introduced in the presented test pattern, but the patient has to correctly mark the position of the artificial distortion (or other test pattern modification) in the test pattern within a specified predefined positioning accuracy criterion.

Typically, in accordance with one possible exemplary embodiment of the present invention, the position marked by the patient as the position of the distortion (or other modification, if used) has to fall within a 1.5° cone angle on each side of the center point of the artificial distortion in to satisfy the position accuracy criterion, but other different cone angles may also be used.

Figure 6:
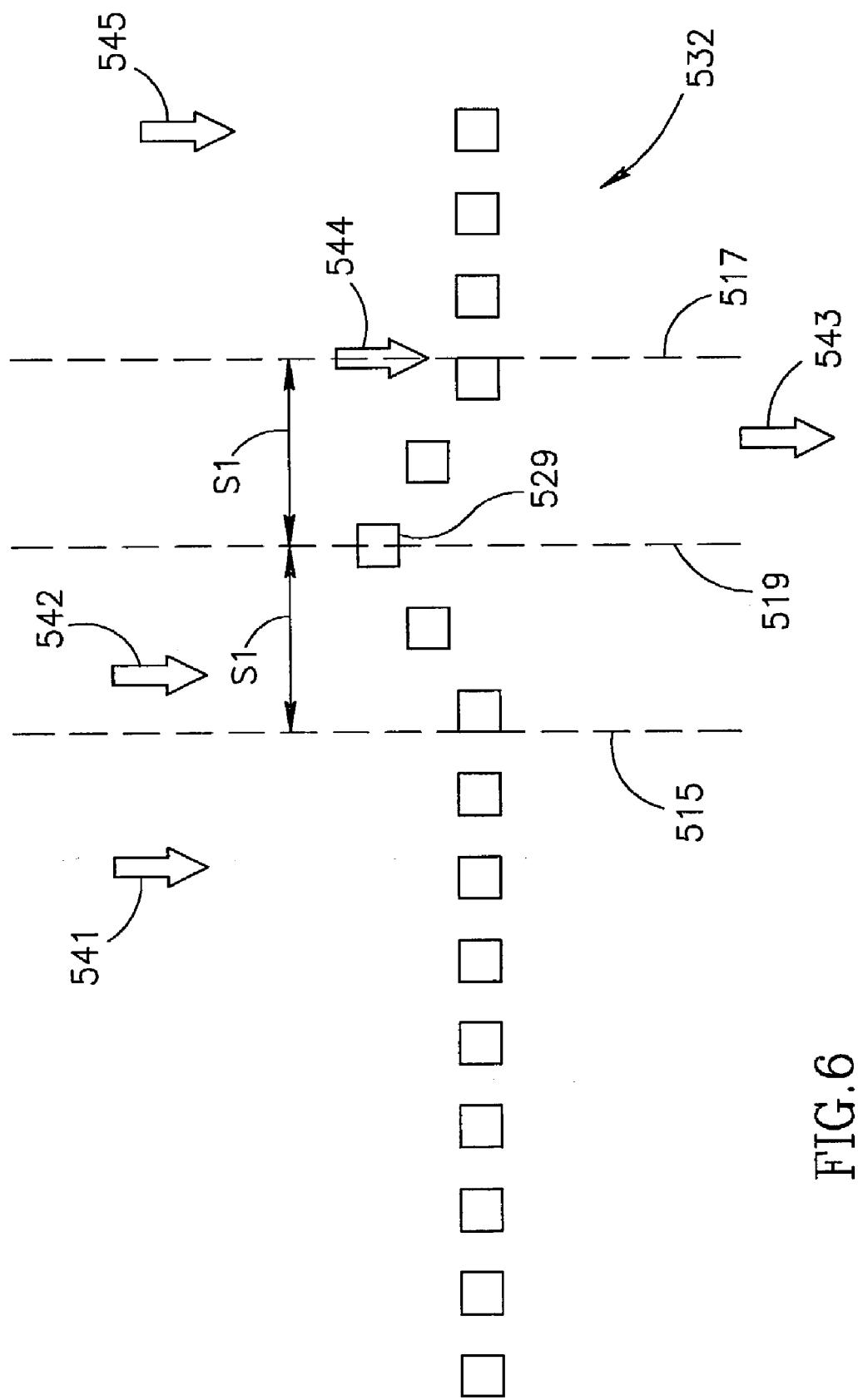
FIG. 6 is a schematic diagram useful in understanding an exemplary positioning accuracy criterion which may be used in the eye testing method, in accordance with one exemplary embodiment of the present invention.

Reference is now made to FIG. 6 which is a schematic diagram useful in understanding an exemplary positioning accuracy criterion which may be used in the eye testing method, in accordance with one exemplary embodiment of the present invention.

The segmented line 532 schematically represents an artificially distorted horizontal line 532 as presented (flashed) on the screen 112 to the subject 100. The segment 529 represents the approximated center of the artificial distortion of the line 532 as presented on the screen 112. The tips of the arrows 541, 542, 543, 544 and 545, schematically represent some possible locations where a subject may potentially mark the position of the approximate the center of the perceived distortion. It is noted that the points clicked on by the subject (which are schematically indicated by the points at the tip of the arrows 541, 542, 543, 544 and 545) need not be on the exact line 532 as perceived by the patient and may be either on or below or above the position on the screen 112 at which the line 532 was briefly presented. The dashed line 519 schematically represents an imaginary vertical line passing through the center of the segment 529 and the dashed lines 515 and 517 schematically represent two imaginary lines parallel to the vertical line 519 and extending to the end (not shown) of the screen 112. The distance S1 between each of the imaginary lines 515 and 517 and the imaginary line 519 is equivalent to a cone angle of 1.5° of the visual field of the subject (when the subject's eye is positioned 50 centimeters from the screen 112).

If the position marked by the subject 100 falls on one of the imaginary lines 515 and 517 or falls anywhere between the two lines 515 and 517, the marked position passes (satisfies) the positioning accuracy criterion and the marked position is deemed to be accurate. If the position marked by the subject 100 falls on the region on the left side of the imaginary line 515 or on the screen region on the right of the imaginary line 517, the marked position does not satisfy the positioning accuracy criterion and the marked position is deemed to be inaccurate. Thus, for example, the marked positions represented by the tip of the arrows 541 and 545 do not satisfy the positioning accuracy criterion while the marked positions represented by the tip of the arrows 542, 543 and 544 satisfy the positioning accuracy criterion.

It is noted that other different types of positioning accuracy criteria may also be used. For example the cone angle represented by the distance S1 may have other values which are smaller or larger than 1.5°. Furthermore, if the test patterns used are slanted lines, other positioning accuracy criteria may need to be established and used.

It is further noted that the satisfying of the positioning accuracy criterion may be computed or evaluated by the computer 105 or by any other suitable computing device, using any suitable computational algorithm as is known in the art.

Analysis of Test Results

The results of the tests performed as disclosed hereinabove may need to be suitably analyzed in order to provide the patient with proper instructions, and possibly his health care provider with a report of the test results. In the case where the patient has been trained to perform the test at home using a desk-top computer or a portable computer (a laptop computer) or the like, if a possible retinal lesion is detected in the test, the patient may be preferably provided with an output which may instruct the patient to promptly visit his ophtalmologist or an eye clinic for a thorough eye examination in order to check the existence of the suspected lesion. If upon this eye examination a lesion is verified, proper therapeutic treatment may be timely administered to the patient, which may substantially improve patient's prognosis due to early detection of the lesion. If no lesion is detected or suspected, the patient may be informed after the test is finished that the results are negative (no lesion is suspected).

Theoretically, if a single occurrence of a perceived distortion of a test pattern is reported or marked by the subject after a non-distorted test pattern is presented to the patient, the patient may be diagnosed as positive and the system may recommend or instruct the patient to visit an ophtalmologist for further eye examination. Such a simple diagnostic criterion may, however, result in a relatively large percentage of false positive diagnoses. This is because many patients may report a distortion in a certain percentage of the presented non-distorted test patterns. Thus, such a simple diagnostic criterion may not be widely applicable to all patients and may possibly be used only for a certain sub-population of patients (such as for example in very high risk patients in which it may be decided that a high percentage of false positive diagnoses is tolerable). It is, however noted, that it is possible to use such a single reporting of a perceived distortion for diagnosing attested individual as positive provided the empirically determined percentage of false positive results is acceptable in view of the application used.

In accordance with another embodiment of the invention, in test embodiments in which there are multiple presentations of the test pattern the test may result in a positive result if the tested individual indicates a perceived distortion in a non-distorted position of a presented test pattern a preselected number of times. For example, the diagnostic algorithm may output a positive result if the tested individual indicates a perceived distortion in a non-distorted position of a presented test pattern three or more times within the same test. The number three in this non-limiting example, is the threshold for outputting a positive test result.

This may have the advantage of reducing the number or the percentage of false positive results in the test. In accordance with such an embodiment of the test of the present invention, the threshold for outputting a positive test result may thus vary between a single occurrence of a perceived distortion and any desired number higher than one of such perceived distortions. The choice of the threshold number may depend, inter alia, on the number of presentations of the test pattern within a single test, the number of repetitions of presenting a test pattern at the same retinal location, the acceptable percentage of false positive results, and other practical considerations.

In accordance with one possible embodiment of the test, a positive result may be output if the number of presentations of a non-distorted test pattern in which the patient indicated the presence of a perceived distortion is equal to or exceeds the threshold number irrespective of the location of projecting of test patterns on the retina.

In accordance with another possible embodiment of the test, a positive result may be output if the number of presentations of a non-distorted test pattern in which the patient indicated the presence of a perceived distortion is equal to or exceeds the threshold number and all the test patterns for which a distortion was indicated were projection the same retinal location.

For most patients, however, other diagnostic criteria may have to be used for reducing the probability of false positive diagnosis.

In accordance with one possible embodiment of the invention, in order to establish if one or more visual disturbance was reliably detected, the data collected and stored in the test is processed as follows.

The data stored for all the non distorted test patterns are checked to see if any segment or component or portion was marked by the patient on any of the test patterns presented in the test. If such a marked segment or component or portion is found, the data for other test patterns is checked for the presence and location of marked segments in other different test patterns. While the finding of a single marked location in a single test pattern may be regarded as an indication of a suspected retinal lesion or retinal abnormality, such a single marked location may have been erroneously marked. It is therefore preferred to corroborate such a result by checking the data obtained for other different test patterns to find out if another location was marked on another test pattern. If two locations were indeed marked by the subject in two different test patterns it may be checked or computed if these two locations satisfy a proximity criterion.

Figure 7A:
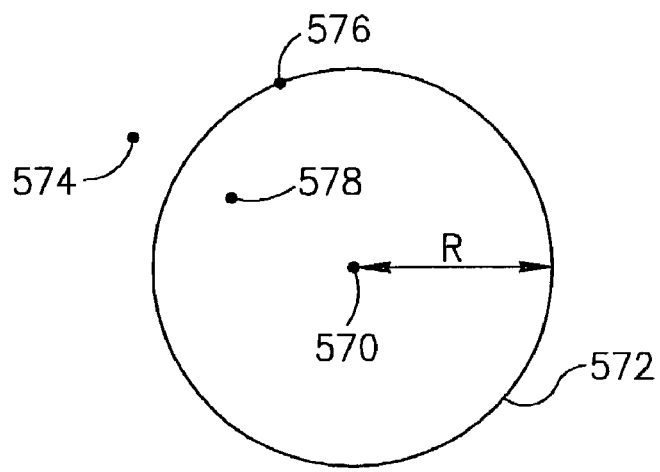
FIGS. 7A and 7B are schematic diagrams useful in understanding exemplary proximity criteria which may be used in exemplary embodiments of the present invention.
Figure 7B:
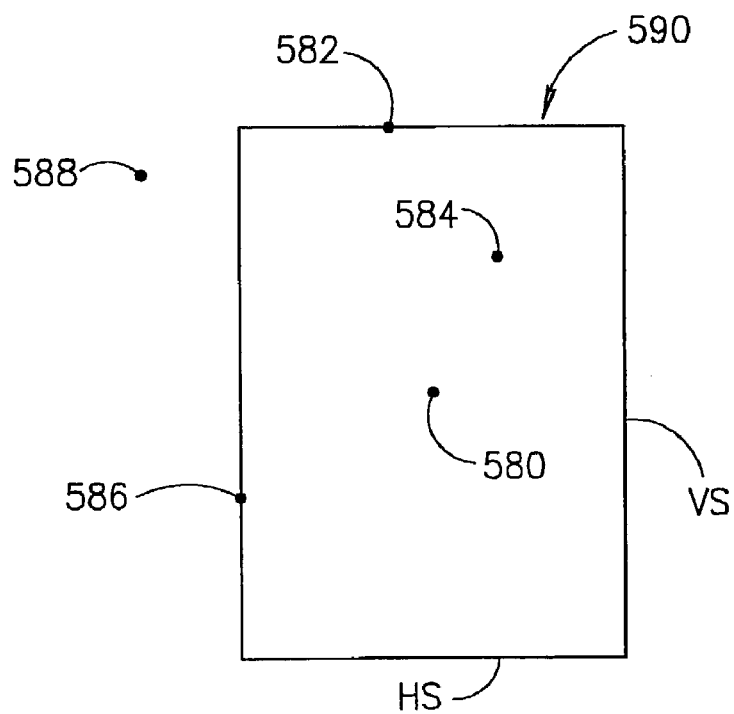

Reference is now made to FIGS. 7A and 7B which are schematic diagrams useful in understanding exemplary diagnostic criteria which may be used in some embodiments of the present invention.

It is noted that the locations of the distortions marked and stored in the computer 105 as disclosed hereinabove may be normalized since they are all known relative to the fixation target. In other words, a correction may be computed to compensate for the movement of the fixation target on the screen 112. Therefore, the coordinates of the marked locations may be normalized relative to the fixation target (if the fixation target moves on the screen 112 as is the case in the moving line test). In this way all the marked points may be related to each other for performing the computations of the diagnostic criteria. In the disclosed exemplary embodiment of flash test, there is no need for normalization since the fixation point does not change its position on the screen 112, and therefore the locations (coordinates) of the marked locations of the distortions or modifications may be used directly without normalization. It is however noted, that if an embodiment of the flash test is used in which the position of the fixation target changes during the test, the coordinates of the positions marked by the tested individual may be similarly normalized.

Different proximity criteria may be used for different combinations of test patterns. The computation is performed on pairs of marked locations in two test patterns. If the pair of marked locations came from test patterns which are orthogonal to each other (such as for example a horizontal straight segmented line and a vertical straight segmented line), the proximity criterion is satisfied if the distance between the two marked locations is equal to or smaller than a cone angle of 3° (three degrees) assuming that the subject's eye was at a distance of 50 centimeters from the screen 112 during the test.

The point 570 of FIG. 7A schematically represents the position of a first location marked by the subject in response to the presentation of a first test pattern. The circle 572 has a radius R which is equivalent to a cone angle of 3° (three degrees) assuming that the subject's eye was at a distance of 50 centimeters from the screen 112 during the test. If a another point which represents the location marked by the subject on another test pattern orthogonal to the first test pattern falls on or within the circumference of the circle 572, the proximity criterion (for pairs of orthogonal test patterns) is met, indicating the presence of a retinal lesion. If the other point falls outside of the circumference of the circle 572, the proximity criterion is not met. For example, each point of the points 576 and 578 meets the proximity criterion with respect to the point 570, while the point 574 does not meet the proximity criterion with respect to the point 570.

It is noted that if the distance between the tested eye and the screen 112 is different than 50 centimeter, the proximity criterion may need to be changed by changing the value of the radius R.

If the two points being checked come from locations marked on test patterns that are parallel (for example, two differently located straight segmented lines which are parallel), another proximity criterion is used.

The point 580 of FIG. 7B schematically represents the position of a first location marked by the subject in response to the presentation of a first test pattern. A rectangle 590 surrounding the point 580 has a horizontal side HS which is equivalent to a cone angle of 4° (four degrees) and a vertical side VS which is equivalent to a cone angle of 6° (six degrees) assuming that the subject's eye was at a distance of 50 centimeters from the screen 112 during the test. The point 580 is disposed at the geometrical center of the rectangle 590. If another point which represents the location marked by the subject on another test pattern parallel to the first test pattern falls on or within the circumference of the rectangle 590, the proximity criterion (for parallel test patterns) is met indicating the presence of a retinal lesion. If the other point falls outside of the circumference of the rectangle 590, the proximity criterion is not met. For example, each point of the points 582, 584, and 576 meets the proximity criterion with respect to the point 580, while the point 588 does not meet the proximity criterion with respect to the point 580.

It is noted that the proximity criteria disclosed hereinabove were empirically determined and that many other different types of criteria may be used, depending, inter alia, on the purpose of the test, the needed accuracy, the desired level of false positive diagnosis, and the particular group of patients for which the test needs to be applied. Thus, the proximity criteria indicated above are given by way of example only and other proximity criteria may be applied which are all within the scope of the invention.

It is further noted that when the test includes test patterns with artificial distortions, any locations which are marked by the subject which are within approximately 2.83° (2.83 degrees) on each side of the center of the artificial distortion are removed from the data prior to performing the calculations for checking any of the proximity criteria to prevent spurious positive results.

It is, however, noted that if the size and/or shape of the artificial distortion is changed, a different distance from the center of the distortion may be used for ignoring data which is assumed to result from the presence of the artificial distortion. It is also noted that when ignoring such data as described hereinabove, the same distance may be applied for all the artificial distortions presented provided that the longitudinal dimension of all the artificial distortions along the test pattern is identical. The application of this distance criterion may, however, be modified if the longitudinal dimension of the artificial distortions presented varies for different artificial distortions presented within the same test, as disclosed in detail hereinafter.

Figure 8:
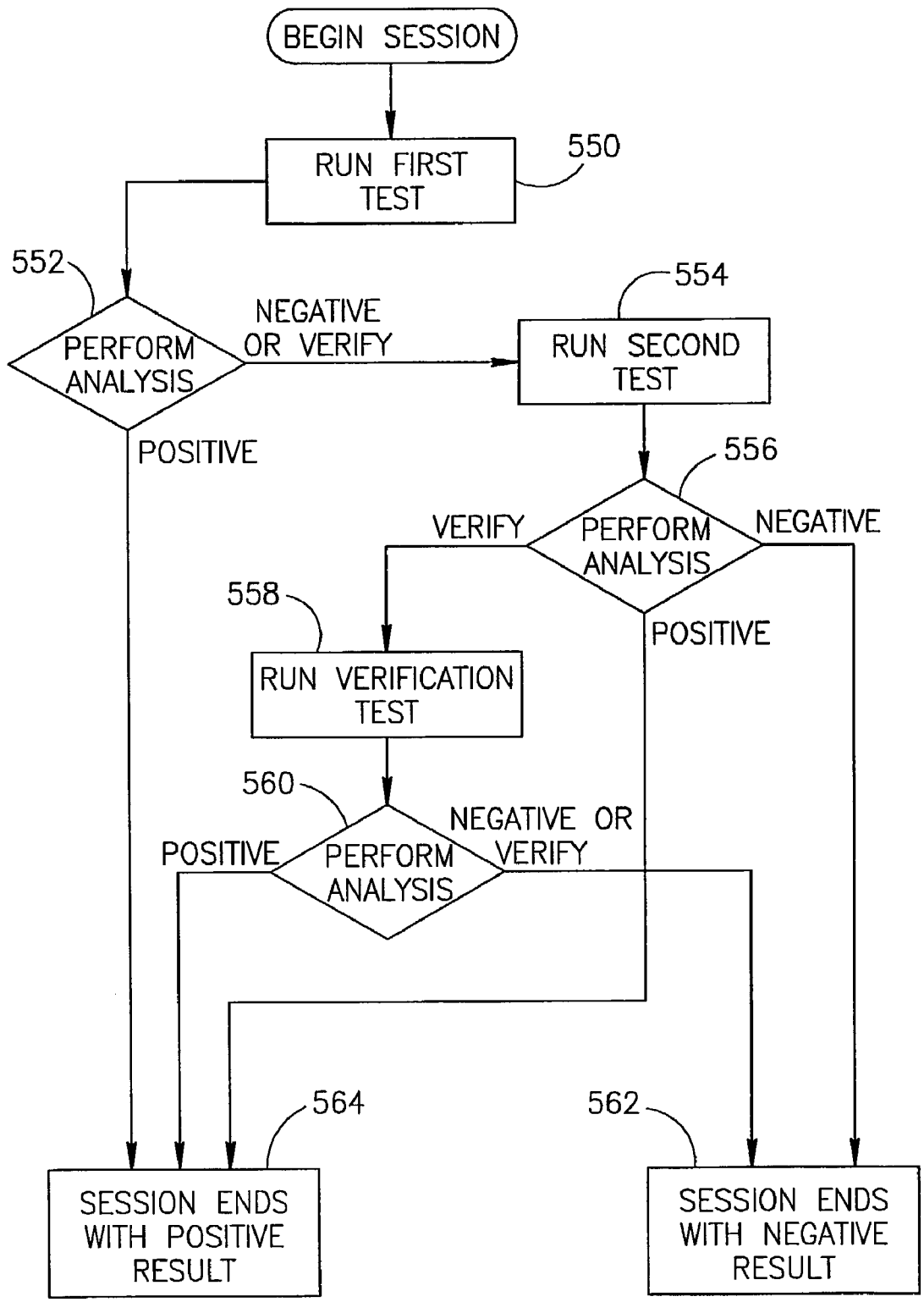
FIG. 8 is a schematic flow diagram useful in understanding a method for performing a test session and analyzing the results of the test session, in accordance with one possible embodiment of the present invention.

FIG. 8 is a schematic flow diagram useful in understanding a method for performing a test session and analyzing the results of the test session, in accordance with one possible embodiment of the present invention.

A test session may include one or more tests and begins by the patient performing a first test (step 550). The tests may be a moving line test or a flash test but in one session all tests are of the same type. After the first test is completed, the data is analyzed (step 552). The analysis may be performed using the proximity criteria as disclosed hereinabove and may result in any of three types of analysis results as follows:

1) a positive result is generated if a retinal lesion is found from the results of the first test by having at least two marked locations in two separate test patterns which meet the proximity criteria disclosed hereinabove.

2) a negative result is generated if the patient did not mark any location in any of the test patterns presented in the test.

3) a verify result is generated if the patient selected and marked locations on one or more test patterns presented during the test, but the marked locations did not meet the proximity criteria.

If the results of the analysis of step 552 generate a positive result, the session ends with a positive result (step 564) indicating that a lesion has been detected, and the session is terminated.

If the results of the analysis of step 552 generate a negative or a verify result, a second test is run (step 554). The second test is a repetition of the first test. The results of the second test are analyzed (step 556) according to the same method as in the analysis of step 552 except that the analysis is run on the pooled results of the first and the second test.

If the results of the analysis of step 556 generate a positive result, the session ends with a positive result (step 564) indicating that a lesion has been detected, and the session is terminated.

If the results of the analysis of step 556 generate a negative result, the session ends in a negative result and is terminated (step 562). If the results of the analysis of step 556 generate a verify result a verification test is run (step 558). The verification test may be different than the first test and the second test in that it does not present to the patient the full complement of the test patterns which are normally included in the first and the second test, but presents to the patient only test patterns which were previously marked by the patient in the pooled results of the first and the second tests. Additionally, while the first and second tests may include artificially distorted test patterns, preferably, the verification test does not include artificially distorted test patterns.

After the verification test is performed, an analysis is performed on the pooled results of the first test, the second test and the verification test (step 560).

If the results of the analysis of step 560 generate a positive result, the session ends with a positive result (step 564) indicating that a lesion has been detected, and the session is terminated.

If the results of the analysis of step 560 generate a negative or a verify result, the session ends with a negative result (step 562) and the session terminates.

Experimental Results

Figure 9:
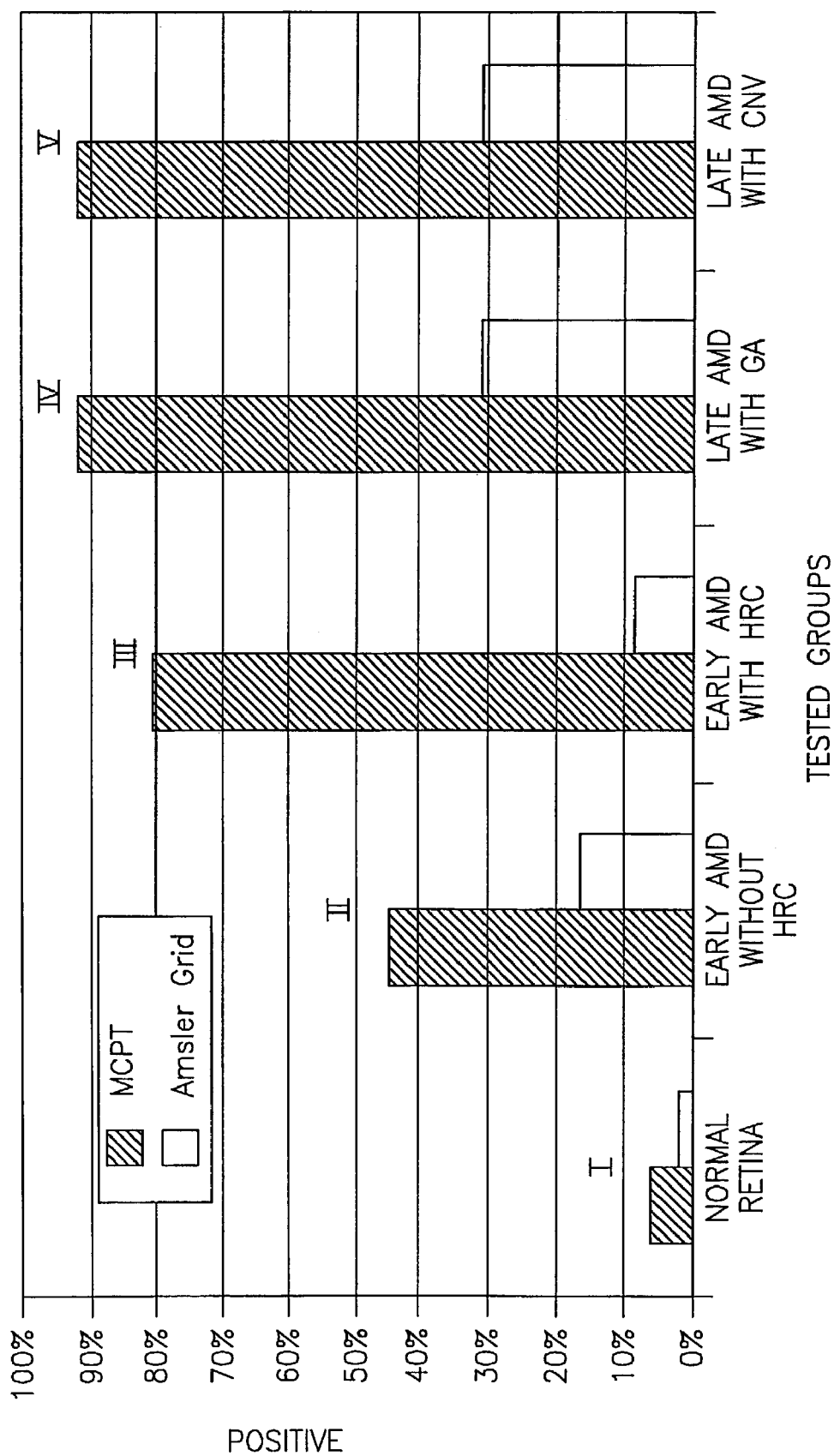
FIG. 9 is a bar graph representing experimental results comparing the performance of t he standard Amsler grid test with the performance of the eye test of the present invention.

Reference is now made to FIG. 9 which is a bar graph representing experimental results comparing the performance of the standard Amsler grid test with the performance of the eye test of the present invention.

The bar graph of FIG. 9 represents the results of testing performed on 108 eyes of patients with clinically diagnosed forms of AMD and on a group of control patients which had a normal retina (the control group).

The test was performed using the flash method as disclosed hereinabove.

The test patterns used were 23 vertical segmented straight lines and 23 horizontal straight segmented lines, each line spanning a 14° cone angle at a distance of 50 centimeters of the eye from the screen 112. The segments were rectangular white segments on a black background, each segment spanning 0.22°×0.22° cone angle. The segments of each line were separated from each other by a cone angle of 0.6°.

The results of the control group which included 51 patients clinically diagnosed as having normal retinas, are represented in the bar pair labeled I (normal retina).

A group with 108 patient included four subgroups. The first subgroup (labeled II) included 18 patients clinically diagnosed as having early AMD without high-risk characteristics (HRC) as in known in the art.

The second subgroup (labeled II) included 35 patients clinically diagnosed as having early AMD with high-risk characteristics (HRC) as in known in the art.

The third subgroup (labeled IV) included 23 patients clinically diagnosed as having late AMD with geographic atrophy (GA) as in known in the art.

The fourth subgroup (labeled V) included 32 patients clinically diagnosed as having choroidal neovascularization (CNV) as in known in the art.

The results of the MCPT for the subgroups are represented by the hatched bar of each bar pair and the results of the standard Amsler grid test are represented by the unfilled bar of each bar pair. The height of the bars represents the percent of the patients in each relevant group which was diagnosed as positive in the test (Amsler test or MCPT test)

It can be seen that for subgroups II, III, IV, and V the MCPT test resulted in a significantly higher percentage of patients being positively diagnosed, as compared to the percentage of the patient diagnosed positive when the Amsler grid test was applied to the same group.

In the normal retina group (the control group I), the difference observed between the percentages of individuals showing positive diagnosis in the MCPT and Amsler grid test was not statistically significant.

Testing System Configurations

It is noted that the testing systems and data analysis methods disclosed hereinabove may be implemented in different device and system configuration.

In accordance with one possible configuration of the system, the system may be implemented on a computer used at the patient's home. Such a computer may or may not be connectable to a network as disclosed in detail hereinabove. A software program may be installed on a commercially available desktop computer, or portable computer or any other suitable type of computer. The computer may be preferably connectable to a network for communicating the test results to a suitable server. Such a system may have the advantages of being inexpensive, simple to operate, and being operable at the patient's home.

In accordance with another configuration of the test system, the system may be meant for use at an eye clinic or at an ophtalmologist's office. Such a system may be implemented on a powerful computer station or workstation and may also provide the ophtalmologist or other eye expert with more advanced data analysis and possibly graphical reports of the test results. Such reports may advantageously provide data about the possible location of the retinal lesion(s), an indication of the lesion size or magnitude, and may possibly include a more detailed report showing the history of test results of the tested patient.

It will also be understood that the system according to the invention may be any suitably programmed computer. Likewise, the invention contemplates a computer program being readable by a computer for executing the method of the invention. The invention further contemplates a machine-readable memory tangibly embodying a program of instructions executable by the machine for executing the method of the invention.

It is noted that while the non-limiting examples of the testing system disclosed hereinabove and illustrated in FIG. 1 include a display device on the surface of which the various test patterns and the fixation target are presented to the subject, other types of systems for administering the test to the subject may be used which do not include a screen or surface. For example, in accordance with another embodiment of the present invention the test patterns and fixation target(s) may be presented to the subject by using an optical system (not shown) similar to a scanning laser ophtalmoscope (SLO).

Figure 10:
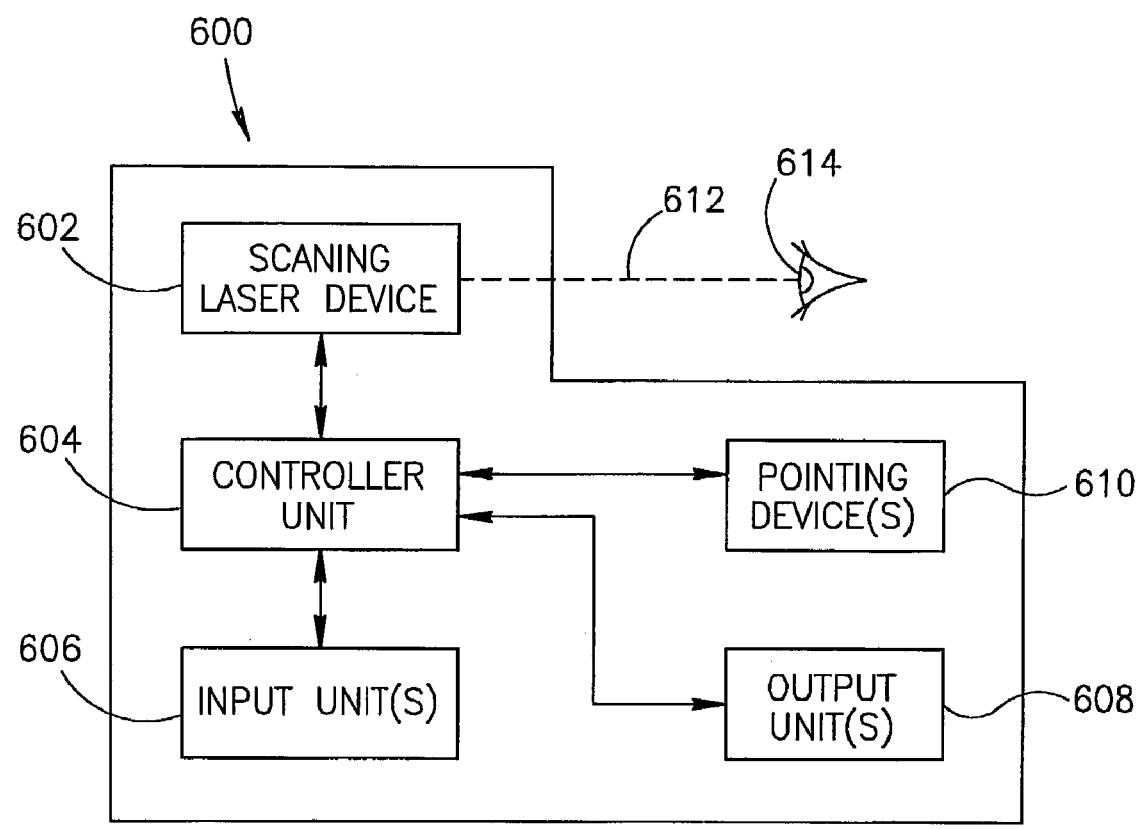
FIG. 10 is a schematic diagram illustrating a system including a scanning laser device or another eye scanning device usable for carrying out an eye test according to another preferred embodiment of the invention.

Reference is now made to FIG. 10 which is a schematic diagram illustrating a system including a scanning laser device usable for carrying out an eye test according to another preferred embodiment of the invention.

In the system 600, the images of the test patterns and fixation target(s), and possibly the log-on screen(s) may be directly projected on the retina of an eye 614 of the test subject (not shown) by suitably directing a laser beam 612 (schematically represented by the dashed line labeled 612) through the pupil of the tested eye 614 and by suitably scanning the laser beam 614 across the retinal surface to form projected images of the test patterns and/or fixation target(s) at specified locations on the retinal surface. The system 600 may include a scanning laser device 602. The scanning laser device 602 may be a scanning laser ophtalmoscope (SLO) device as is known in the art, or any other device capable of controllably scanning a beam of coherent or non-coherent light across the retina of an eye. The scanning laser device 602 may be suitably coupled to a controller unit 604 or to a computer (not shown) for controlling the operation of the scanning laser device 602. The controller unit 604 may also be a computer such as a workstation, or mainframe, or laptop computer or a hand held or other portable computing device, or a personal computer or any other type of computing device known in the art. The controller unit 604 may be coupled to suitable pointing device(s) 610. The pointing device(s) 610 may be a mouse (not shown), and/or keyboard connected to a computer or may be any other suitable pointing device or devices as disclosed hereinabove or as known in the art. The system 600 may also include one or more output unit(s) 608, such as, but not limited to, a display, a printer unit, or any other suitable output device for enabling interaction of a user with the system 600 and/or for producing hard copy output of test results or the like. The output unit(s) 608 may be suitably coupled or connected to the controller unit 604.

In operation the system 600 may be used for applying any of the tests disclosed hereinabove but instead of showing the test pattern, and the fixation targets on a screen 112 of a display device 115, the images of the test patterns and the fixation target(s) may be directly projected onto the retina of the tested eye 614 by the scanning laser device 602 by suitably scanning the laser beam 612 on the retina of the eye 614. The laser beam 612 may also be used to project an image of a cursor (similar to the cursor 225 of FIG. 3) directly on the retina of the eye. The movement of such a projected cursor may be controlled by the one or more of the pointing devices 610, such as but not limited to a mouse (not shown).

Thus, the system 600 may be used to administer to a patient any of the tests disclosed hereinabove (including but not limited to the moving line test and the flash test) and to record and store the responses of the patient including but not limited to the marking of parts or portions or segments at which distortions or modifications as disclosed hereinabove were perceived and marked by the patient. The system 600 may also process the test results using any of the methods and test criteria disclosed hereinabove to produce a positive or negative diagnosis. The system 600 may also be suitably connected to a communication network (such as, but not limited to the communication network 130 of FIG. 1) and may communicate with other devices or computers, or the like, over the communication network.

It is noted that the laser scanning device 602 may be replaced or substituted with other scanning devices (not shown) known in the art which are capable of directing a narrow light beam having a suitably narrow beam cross-sectional area onto an eye and scanning the beam controllably across the retina. The light beam need not be a laser beam but may be any beam of non-coherent light which may be suitably scanned across a retina with sufficient speed and resolution.

It is noted that the construction and operation of laser scanning ophtalmoscopy devices are well known in the art, are not the subject matter of the present invention and are therefore not described in detail herein.

Assessment of Disease Progression in AMD

While the testing procedure disclosed hereinabove and graphically illustrated in FIGS. 4A–4J may produce data which may be analyzed to determine the presence of retinal abnormalities (such as, but not limited to, AMD related retinal lesions or diabetes related retinal lesions, or the like), and to determine whether a patient tests positive or negative for the presence of retinal lesions, it may also be desirable to determine the degree of severity of the detected retinal lesion or lesions and to determine the stage or progression of disease in the tested patient or subject.

AMD patients may generally be clinically divided into groups such as patients having early AMD without high-risk characteristics (HRC), patients having early AMD with HRC, patients having late AMD with geographic atrophy (GA), and patients having advanced AMD with choroidal neovascularization (CNV). It may be desirable to classify a patient as belonging to a patient group, such as one of the above indicated groups without having to resort to a lengthy and expensive retinal examination by an ophtalmologist.

As disclosed hereinabove, in a patient having a retinal lesion, when the patient is presented with a non-distorted test pattern at a first location on the screen 112 of the display device 115, which causes the image of the test pattern to be projected on the retina such that part of the projected image of the test pattern falls on the lesioned region of the retina, the patient may observe a distortion or abnormal appearance of part of the perceived image of the test pattern. This type of observed distortion or other abnormal or modified appearance or change in the perceived image of the test pattern is referred to as a pathology related observed distortion (PROD) hereinafter.

While performing the visual tests disclosed hereinabove, which included the use of artificially distorted test patterns for testing the patients reliability in perceiving and/or reporting these artificially introduced distortions, the inventors of the present invention have noticed that if an artificially distorted test pattern is presented at a location on the screen 112 such that part of the projected image of the test pattern falls on a lesioned region of the retina, the patient may respond to the presentation of the test pattern in one of four different types of responses.

In the first type of possible response, the patient may perceive and mark two distortions at two locations of the perceived image of the artificially distorted test pattern. One perceived distortion may be associated with the presence of the retinal lesion and is therefore defined as a PROD and the other perceived distortion may be associated with the distortion which was artificially introduced into the displayed artificially distorted test pattern. The latter type of observed distortion is referred to as an artificially introduced observed distortion (AIOD) hereinafter. This first response type is referred to as a "B type" response hereinafter, to indicate that the patient reported both the PROD and the AIOD.

In a second type of possible response, the patient may perceive and mark only the distortion associated with the presence of the retinal lesion (only the PROD). This second response type is referred to as a "P type" response hereinafter, to indicate that the patient reported only the PROD.

In a third type of possible response, the patient may perceive and mark only a distortion associated with the presence of the distortion which was artificially introduced into the presented test pattern (only an AIOD). This third response type is referred to as an "A type" response hereinafter, to indicate that the patient reported only the AIOD.

In the fourth type of possible response, the patient may not observe or mark any distortion at all. This fourth response type is referred to as an "N type" response hereinafter, to indicate that the patient did not report any observed distortion.

Figure 11:
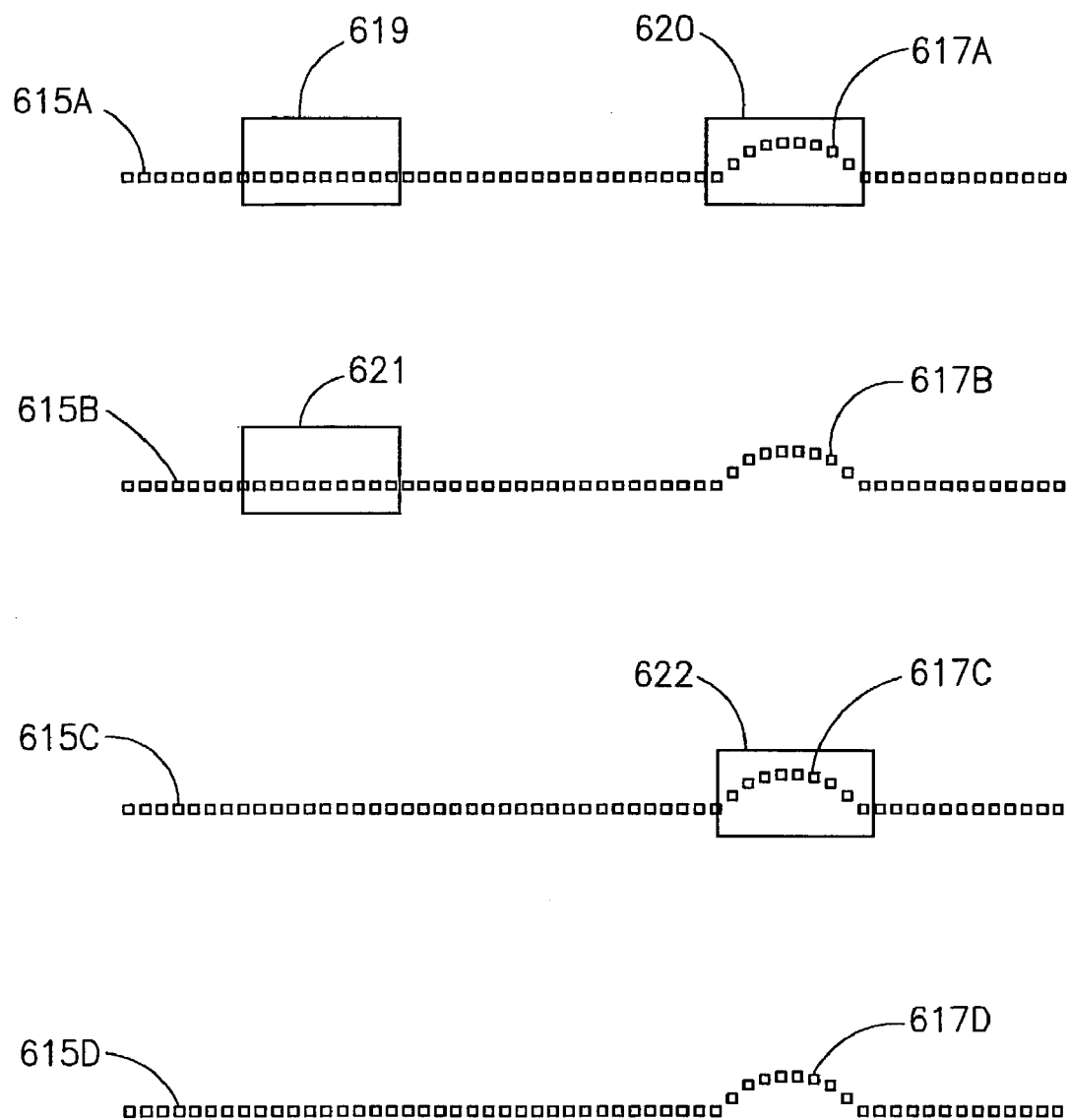
FIG. 11 is a diagram schematically illustrating four different possible response types of the same patient when the patient is presented with a test pattern including an artificial distortion, such that part of the projected image of the test pattern falls on a retinal or choroidal lesion in the patient's retina.

Reference is now made to FIG. 11 which is a diagram schematically illustrating four different possible response types of the same patient when the patient is presented with a test pattern including an artificial distortion, such that part of the projected image of the test pattern falls on a retinal lesion in the patient's retina.

The distorted segmented lines 615A, 615B, 615C, and 615D schematically represent a test pattern presented to the patient as disclosed in detail hereinabove (by presentation on a display device, such as for example the screen 112 disclosed hereinabove, or by direct retinal projection such as for example by using the system 600 disclosed hereinabove). It is noted that the distorted segmented lines 615A, 615B, 615C, and 615D schematically represent the test pattern as presented to the patient (and not the patterns as observed by the patient).

The artificial distortions 617A, 617B, 617C, and 617C comprise displaced segments of the segmented lines 615A, 615B, 615C, and 615D, respectively. The rectangular boxes 619, 620, 621,and 622, schematically represent regions of the test pattern in which the patient placed a mark in the various different response types. It is noted that the boxes 619, 620, 621,and 622 do not indicate the precise position in which the patient marked an observed distortion but rather schematically represent the approximate position at which the patient observed a distortion.

The segmented line 615A and the rectangular boxes 619 and 620 superimposed thereon schematically represent a non limiting example of a response in which the patient reports at least two observed distortions by marking at least two different regions on the test pattern in response to the presentation of a test pattern including an AD 617A. The box 619 schematically represents the region in which the patient observed a distortion due to a retinal lesion (a PROD), and the, box 620 schematically represents the region in which the patient observed a distortion due to the artificial distortion 617A (an AIOD). It is noted that while this non-limiting schematic example shown illustrates a case in which the patient marked only two positions in response to the presentation of the test pattern 615A (one marked position corresponding to an AIOD and the second marked position corresponding to a PROD), in other possible responses the patient may mark more than two positions. For example, the patient may mark one position in the region of the artificial distortion 617A and two or more positions in other regions (not shown in FIG. 11) of the test pattern 615A.

The segmented line 615B and the rectangular box 621 superimposed thereon schematically represent a non-limiting example of a response in which the patient reports one or more observed distortions by marking one or more positions on the display screen, in response to the presentation of a test pattern 615B including an AD 617B, as disclosed in detail hereinabove. The box 621 schematically represents the region in which the patient observed a distortion due to the retinal lesion in the tested eye. In this type of response the patient did not report an observed distortion in the region of the artificial distortion 617B.

The segmented line 615C and the rectangular box 622 superimposed thereon schematically represent a non-limiting example of a response in which the patient reports a single observed distortion by marking one position on the display. The box 622 schematically represents the region in which the patient observed a distortion due to the artificial distortion 617C. In this type of response the patient does not observe (and therefore does not mark) a distortion due to the presence of the retinal lesion.

The segmented line 615D having no boxes superimposed thereon schematically represents a response in which the patient did not mark any position on the display, in response to the presentation of the test pattern because no distortion was observed (and therefore no distortion was marked) by the patient neither in the region of the AD 617D presented in the test pattern 615D nor in the region of the retinal lesion.

It is noted that the response types illustrated in FIG. 11 are schematic and are given by way of example only, and that the type of response of a patient to the presentation of a test pattern may depend, inter alia, on the individual patient being tested, the shape and type of the presented test pattern, the actual size and shape of the artificial distortion introduced into the test pattern, and the type and severity of the retinal lesion in the retina of the tested eye.

The inventors of the present invention have found that when patients are presented with test patterns including artificially introduced distortions such that part of the projected image of the test pattern falls on a lesioned region of the retina, there is a correlation between the retinal lesion type of the patient (i.e. the severity of the lesion) and the type of patient response exhibited. Moreover, the type of response also depended on the size or magnitude of the distortion artificially introduced into the test patterns presented to the patient.

By varying the magnitude of the artificial distortion introduced into the test patterns presented to patients in clinical experiments it was unexpectedly found that for a particular retinal lesion, as the artificially introduced distortion in the presented test pattern becomes larger in magnitude, there is a higher probability that the patient may preferentially observe and report the artificially introduced distortion while not observing and reporting a distortion due to the presence of the retinal lesion.

Thus, as empirically and unexpectedly found by the inventors of the present invention, when patients are presented with test patterns including artificially introduced distortions such that part of the projected image of the artificially distorted test pattern falls on a lesioned region of the retina, the probability that a patient will respond to the presentation of the artificially distorted test pattern with the above described third type of response (observing and reporting only the AIOD) increases as the magnitude of the distortion increases.

While the exact psychophysical basis for this phenomenon is not yet clear, it may appear as if the PROD and the AIOD "compete" for patient's attention and that there is a higher probability that a distortion which is larger or more noticeable or more prominent may be preferentially noticed and reported by the patient, and that there may be is a smaller probability that the smaller or less noticeable or less prominent distortion will be noticed and reported.

The inventors of the present invention have thus noticed that by presenting a patient with test patterns having artificially introduced distortions of various sizes, or amplitudes, or magnitudes (graded distortions) which are presented to the patient such that they fall on the lesioned retinal region and by recording and analyzing the responses of the patient it may be possible to assess the severity of the patient's lesion or to classify the patient as belonging to a particular class of clinically defined disease progression state. For example, in the case of tested AMD patients it may be possible to classify the tested patients into groups representing different stages of AMD, as is disclosed in detail hereinafter.

Results of "Competition" Experiments

The competition experiments were performed using artificially distorted test patterns which were displayed to the patients on the display screen of a laptop computer. The Laptop personal computer used was a Dell Latitude laptop computer model C-600, having a 14.1 inch TFT color screen, but any other suitable computer or display may also be used.

It is noted that all the angular dimensions disclosed hereinbelow are given as cone angles of the visual field of the subject (when the subject's eye is positioned 50 centimeters from the screen of the display device, such as the display of laptop computer used for the test). Each of the test patterns displayed on the screen included 27 square segments arranged as a segmented line, the segments were white segments presented on a black background. Each square segment had the dimensions of 0.26° by 0.26° (cone angles, when observed at a distance of 50 centimeters from the patient's tested eye as disclosed hereinabove).

In the non-distorted (flat) linear test patterns (not shown), all the segments were linearly arranged and the distance separating the adjacent ends of two adjacent segments was 0.22°. The distance between the centers of two adjacent segments is 0.52°.

In the exemplary artificially distorted test patterns used in the competition experiment, three segments out of the twenty seven square segments of the test pattern are displaced such that they are not linearly arranged relative to the other remaining segments. The remaining twenty four segments are linearly arranged such that their centers all lie on a straight line (see, for example, imaginary line 660 of FIG. 12 below).

Figure 12:
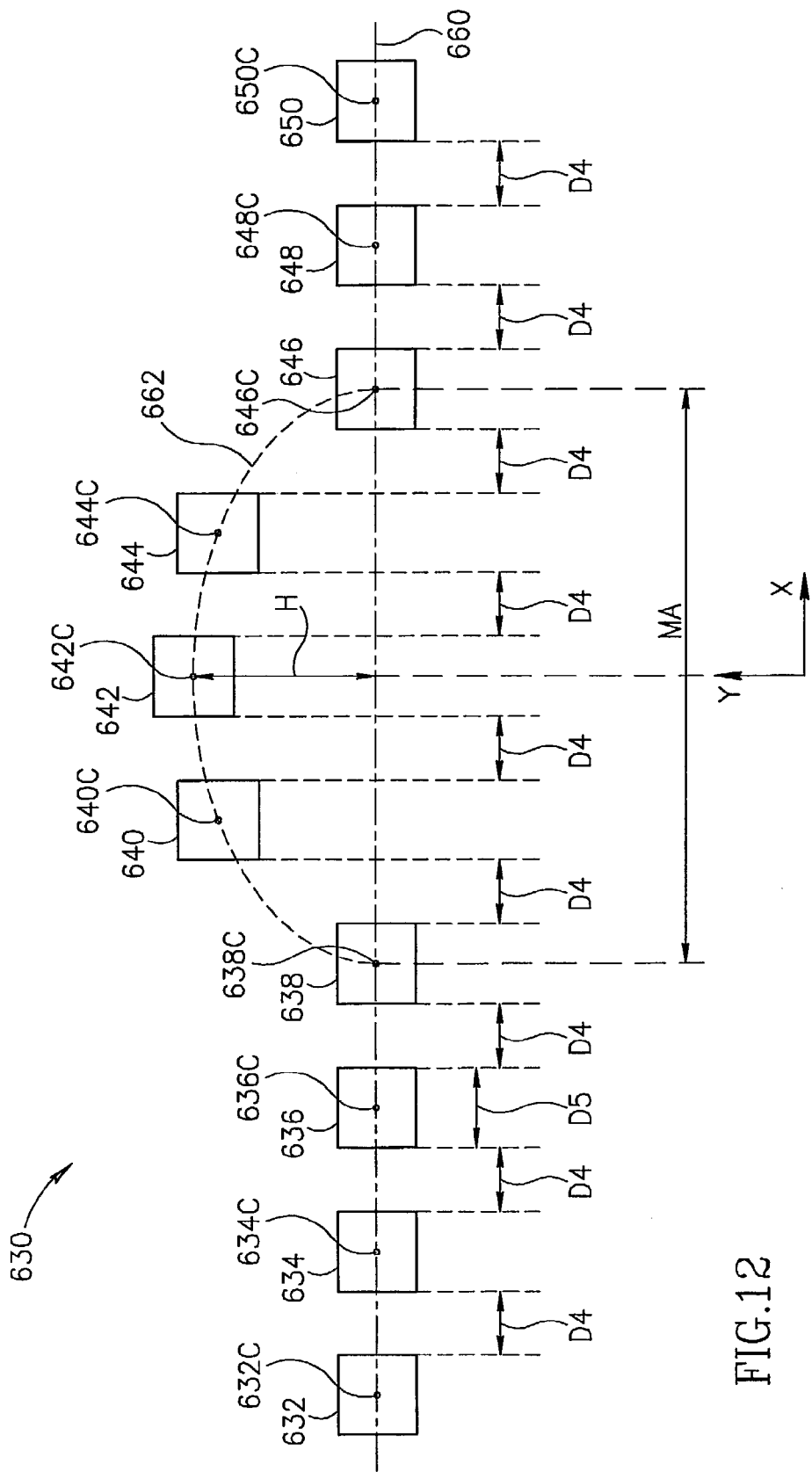
FIG. 12 is a schematic diagram illustrating in detail part of a schematic artificially distorted test pattern used in the competition experiments performed in accordance with an embodiment of the present invention.

Reference is now made to FIG. 12 which is a schematic diagram illustrating in detail part of a schematic artificially distorted test pattern used in the competition experiments performed in accordance with an embodiment of the present invention.

In FIG. 12, a part of an artificially distorted test pattern 630 is illustrated. Only ten segments 632, 634, 636, 638, 640, 642, 644, 646, 648, and 650 of the twenty seven segments of the test pattern 630 are shown.

The segments 632, 634, 636, 638, 646, 648, and 650 are arranged such that their centers 632C, 634C, 636C, 638C, 646C, 648C, and 650C, respectively are all disposed along a straight line 660, while the segments 640, 642 and 644 are disposed such that their centers 640C, 642C and 644C, respectively, are offset from the line 660 (it is noted that the line 660 is an imaginary line given only for the purpose of illustrating the arrangement of the various segments of the test pattern 630, the line 660 does not form a part of the test pattern 630 and is not shown to the patient). The seventeen segments included in the test pattern 630 and not shown in FIG. 12 (for the sake of clarity of illustration) may be disposed on the straight line 660 adjacent to the segment 632, or adjacent to the segment 650. Alternatively some of the remaining seventeen segments which are not shown in FIG. 12 may be disposed on the straight line 660 adjacent to the segment 632 and the rest of the remaining seventeen segments may be disposed on the straight line 660 adjacent to the segment 650.

The left and the right sides of each of the twenty seven segments included in the test pattern 630 are preferably oriented such that they are perpendicular to the line 660 (it may, however, also be possible to use other orientations).

The distance D4 between adjacent segments (represented by the double headed arrows D4) is 0.22° and the side D5 of all the square segments of the test pattern 630 is 0.26° (as indicated above, the values of D4 and D5 represent cone angles, when observed at a distance of 50 centimeters from the patient's tested eye as disclosed hereinabove).

The distorted part of the exemplary test pattern 630 comprises the segments 640, 642, and 644. The centers 640C, 642C and 644C of the segments 640, 642 and 644, respectively, are disposed on an (imaginary) half ellipse curve 662 (schematically represented by the dotted line labeled 662). It is noted that the half ellipse curve 662, and the center points 632C, 634C, 636C, 638C, 640C, 642C, 644C, 646C, 648C, 650C are shown in FIG. 12 for explanatory and illustrative purposes only, and do not appear in the test patterns shown to the patients.

The distance H between the center point 642C of the segment 642 (the central segment of the three segments 640, 642 and 644 forming the artificial distortion) and the straight line 660 is defined as the height of the artificial distortion. The distance H comprises half of the minor axis of an ellipse (not shown in its entirety) which includes the half ellipse curve 662. The distance MA is the major axis of such an ellipse.

For the exemplary test pattern 630 partially illustrated in FIG. 12, the computer program which generates the test patterns for display on the screen 112 may compute the positions of the segments of the test pattern by using the above indicated segment dimensions (0.26° by 0.26°) and segment spacing (0.22°) to determine the horizontal coordinate of the center point 642C (defined as the position of the center point 642C along the horizontal axis labeled X), and the vertical coordinate of the center point 642C (defined as the position of the center point 642C along the vertical axis labeled Y). The computer program may then compute the vertical coordinates of the center points 640C, and 644C as disposed on the computed half ellipse curve 662. The horizontal coordinates of the center points 640C, and 644C may be computed from the computed horizontal coordinate of the center point 642C and from the known values of D5 and D4.

Thus, for artificial distortions having different values of H, the imaginary half ellipse curves may be of different sizes.

It is noted that while in the exemplary test pattern 630 of FIG. 12 The major axis MA of the ellipse which includes the half ellipse curve 662 starts at the center point 638C of the segment 638 and ends at the center point 646C of the segment 646, this need not be the case for artificial distortions having different values of the distortion heights H. In other test patterns (not shown) the computed half ellipse curve (not shown) may intersect the straight line 660 at points which are different than the center points 638C and 646C. The exact points of intersection of the (imaginary) half ellipse curve and the line 660 may depend on the values of D4, D5, and H. For example, in accordance with one non-limiting example the computed half ellipse curve (not shown) may intersect the straight line 660 at a first point (not shown) located between the center points 636C and 638C and at a second point located between the center points 646C and 648C.

It is noted that in EXPERIMENT 1 and EXPERIMENT 2 detailed below, the computations were rounded to the nearest pixel value to accommodate for the finite pixel size and resolution on the TFT screen of the laptop computer used in the test.

The computer program used for calculating the positions of the various segments of the test patterns (such as but not limited to the test pattern 630 partially illustrated in FIG. 12), computed the positions of the segments 640, 642, and 644 included in an AD having a height H by using the equation for an elliptical curve as is known in the art and the known values of D4, and D5. Such a computation is well known in the art and may be implemented using many computational methods or program code all of which are known in the art and are therefore not described in detail hereinafter.

Competition Study Details

The competition study included two different experiments (EXPERIMENT 1 and EXPERIMENT 2 disclosed hereinbelow). Each experiment was performed by testing different patient groups. In both experiments, each tested patient was presented with test patterns using the flash method disclosed hereinabove with a test pattern presentation duration of 160 milliseconds.

The dimensions are given as cone angles wherein each degree represents 300 micron over the retina. If the subject is 50 cm from the display screen of the computer, each degree is equivalent to a length of 0.88 centimeter on the display screen.

Some of the test patterns were linear (flat) test patterns as disclosed hereinabove, and did not include an artificial distortion. Most of the test patterns included a single artificial distortion.

Experiment 1

In this experiment two groups were tested. The first group included 28 subjects all clinically diagnosed to have normal retinas (normal group). The second group included 32 subjects clinically diagnosed to have AMD with high risk characteristics (AMD with HRC group). All subjects (ranging in age between 50–90 years old) were given a complete eye examination by a retina specialist prior to performing the tests for the experiment. After the diagnosis was recorded by the retina specialist each of the patients was tested using an MCPT adapted for the experiment as disclosed hereinafter.

The artificial distortions presented were selected from artificial distortions (AD) having a height of 0.19°, 0.22° as disclosed hereinabove. Each test pattern had a dimension of approximately 14°. Half of the test patterns presented to each patient, were generally horizontally oriented and the other half were generally vertically oriented, as disclosed hereinabove. Altogether, the test patterns were adapted to map a 14°×14° grid on the macula with a 1° resolution. The fovea of the tested eye was at the center of the mapped region. The sequence of presentation of the horizontal and vertical test patterns within a single test was randomly selected. The sequence of presenting signals with an AD and without an AD was also randomized. The sequence of presentation of the test patterns having different-heights (heights of 0.19°, 0.22°) was also randomized.

Each eye was tested by presenting test patterns at thirty different locations on the display of the laptop computer. Fifteen locations were horizontally oriented on the display of the laptop computer and fifteen locations were vertically oriented on the display of the laptop computer. At each of the thirty different locations on the display of the laptop computer there were five randomized presentations of the test patterns, one presentation of a test pattern with no AD (a flat test pattern), two presentations of a test pattern including an AD with a height of 0.19°, and two presentations of a test pattern including an AD with a height of 0.22°. Altogether, each test included 150 presentations of test patterns to the tested patient's eye.

In the pair of test pattern presentations including an AD with a height of 0.19°, the position within the test pattern of the three segments forming the AD was randomly selected, but the minimal distance between the positions of the AD in the two presentations was 5° (In other words, if the test patterns presented at each of the two presentations were to be superimposed on each other, the distance between the center points of the central segments of each of the ADs would be equal to or larger than 5°).

Similarly, in the pair of test pattern presentations including an AD with a height of 0.22°, the position within the test pattern of the three segments forming the AD was randomly selected, but the minimal distance between the positions of the AD in the two presentations was 5°.

It is noted that while the random distribution of the positions of the artificial distortions and the 5° distance ensures adequate distribution of the positions, other methods for setting the positions of the artificial distortions in the test patterns may also be used. For example, in other experiments, a look up table (LUT) stored in the memory of the laptop computer or other computer of the computer system 105 Was used. The LUT included a set of positions selected to generate a relatively uniform distribution of the artificial distortion's position in the test patterns presented within a test.

The distribution of the positions were sequentially read from the LUT and used by the system to determine the position of the AD within the test patterns. In accordance with other embodiments of the present invention, satisfactory results may thus be obtained using such a LUT or a random number generator, or a pseudo random generator, or any other algorithm adapted for generating randomly or non-randomly distributed positions of the artificial distortions, as long as the sequence of positions cannot be remembered or otherwise memorized or predicted by the patient or by the individual being tested.

The patients were asked to mark the positions at which a distortion was observed, by using a mouse connected to the Laptop computer as disclosed in detail hereinabove for the flash test. All the test data were stored in the laptop computer for further processing and analysis, including, inter alia, all the settings and parameters of the presented test patterns, the location and height of the AD in the artificially distorted test patterns, the sequence of presentation of the test patterns, and the patients responses to each test pattern presentations.

The Results were then Processed as Follows:

The percentage of marking "flat" test patterns by the patient $P_F$ was computed according to the equation $P_F=100 N_M/P_{FT}$, wherein $N_M$ is the total number of test pattern presentations in which the patient marked the presence of one or more observed distortions when presented with a test pattern having no AD (a flat test pattern), and $P_{FT}$ is the total number of test patterns having no AD ("flat" test patterns) which were presented to the patient in the test.

In the exemplary, non-limiting, tests performed in EXPERIMENT 1, the total number of presentations of such flat test patterns to a patient in a single test of EXPERIMENT 1 is thirty presentations ($P_{FT}=30$).

The computer further analyzed the position of the markings by the patient in response to the presentation of test patterns having an AD, and classified the responses into different types.

The computer analyzes the patient responses to detect two different patient response types. The first patient response type is a response in which the patient marked one or more positions in response to the presentation of a test pattern including an AD, and in which all of the positions marked by the patient were defined as being due to the presence of a retinal lesion by applying the criteria disclosed hereinafter and illustrated in FIGS. 13 and 14. This type of patient response is defined as a P type response hereinafter.

Figure 13:
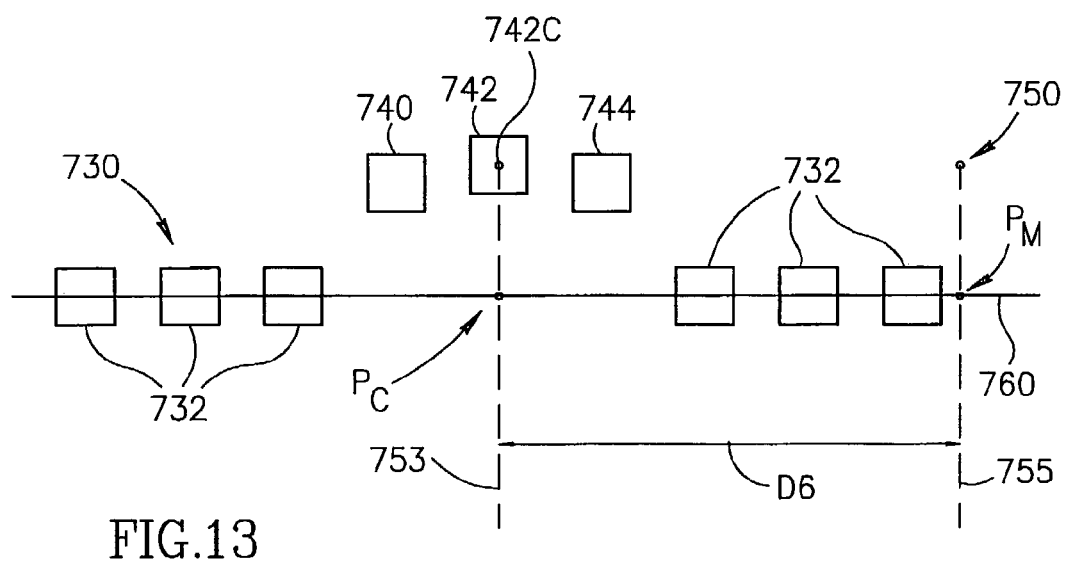
FIGS. 13 and 14 are schematic diagrams illustrating in detail the criterion for determining if a position marked by the patient is due to a pathology related observed distortion (PROD) indicating the presence of a retinal or choroidal lesion or due to an artificially induced observed distortion (AIOD) indicating the observation of an artificial distortion, in accordance with one embodiment of the present invention.
Figure 14:
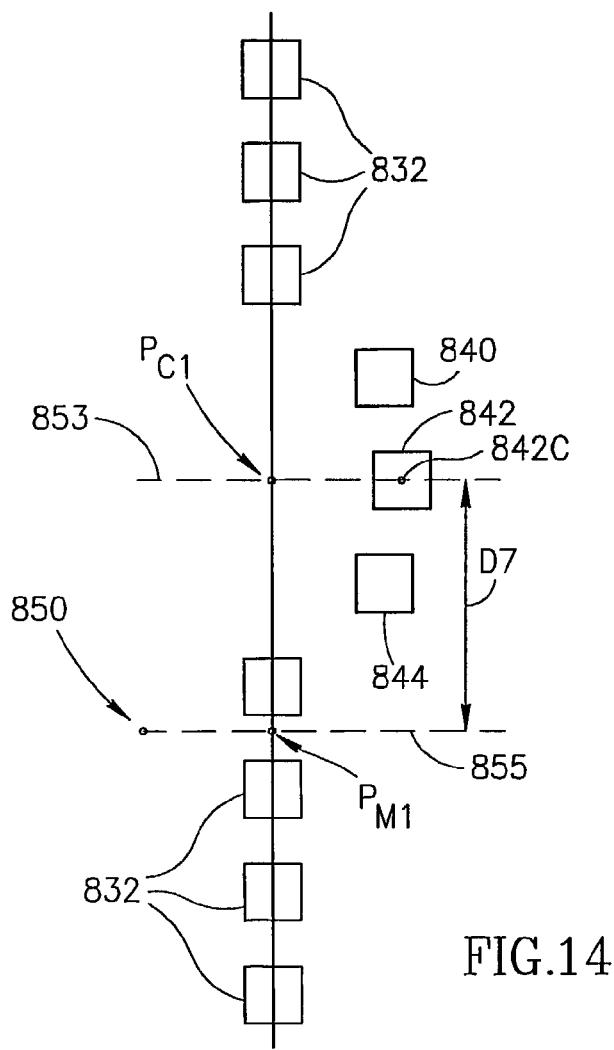

The second patient response type is a response in which the patient marked at least two positions in response to the presentation of a test pattern including an AD, and in which at least one of the positions marked by the patient was defined as being due to the presence of a retinal lesion, and at least one of the positions was defined as being due to the artificial distortion present in the test pattern, wherein the definitions were made by applying the criteria disclosed hereinafter and illustrated in FIGS. 13 and 14. This type of patient response is defined as a B type response hereinafter.

In the first type of patient response, if all the positions marked by the patient in response to the presentation of a test pattern including an AD are at a distance equal to or greater than 2.83° from the position of the center of the AD, the markings are considered to represent a PROD indicating that the patient observed distortion(s) due to the presence of a real retinal lesion (or lesions) or abnormality, and the response is identified and recorded as a P type response.

In the second type of patient response there are at least two positions marked by the patient. At least a first position marked by the patient in response to the presentation of a test pattern including an AD is at a distance smaller than 2.83° from the position of the center of the AD. This marking is considered to be due to an AIOD (assuming that the distortion marked by the patient is due to the AD). Additionally, at least a second position marked by the patient in response to the presentation of the test pattern is at a distance equal to or greater than 2.83° from the position of the center of the AD. This second marked position is considered to be due to a PROD (assuming that the distortion marked by the patient is due to a retinal lesion). Such a response is identified and recorded as a B type response.

Reference is now made to FIGS. 13 and 14 which are schematic diagrams illustrating in detail the criterion for determining if a position marked by the patient is due to a PROD indicating the presence of a retinal lesion or due to an AIOD indicating the observation of an artificial distortion, in accordance with one embodiment of the present invention.

FIG. 13 illustrates part of a horizontal artificially distorted test pattern 730. The test pattern 730 includes square segments 732. The segments 732 are arranged such that their centers (not shown) are disposed on an imaginary straight line 760 (the imaginary line 760 is not part of the test pattern 730, is not shown to the patient, and is shown solely for illustrative purposes to indicate the arrangement of the segments included in the test pattern 730). The test pattern 730 includes additional segments which are not shown for the sake of clarity of illustration. The test pattern 730 is artificially distorted as disclosed hereinabove. The test pattern 730 includes segments 740, 742, and 744. The centers of the segments 740, 742 and 744 are offset from the imaginary line 760.

The dashed line 753 which starts at the center 742C of the segment 742 is perpendicular to the line 760, and intersects the line 760 at the point $P_C$. The point 750 schematically represents a position marked by the patient (on the display on which the test pattern 730 is presented) in response to the presentation of the test pattern 730. The dashed line 755 which starts at the point 750 is perpendicular to the line 760, and intersects the line 760 at the point $P_M$.

The double headed arrow labeled D6, represents the distance D6 between the points $P_C$ and $P_M$ along the line 760. If the distance D6 is equal to or greater than 2.83° (expressed as the cone angle at a distance of 50 centimeters of the tested eye from the display screen on which the test pattern 730 is displayed), the position of the marked point 750 is defined as being due to a PROD. If the distance D6 is smaller than 2.83°, the position of the marked point 750 is defined as being due to an AIOD.

FIG. 14 illustrates part of a horizontal artificially distorted test pattern 830. The test pattern 830 includes square segments 832. The segments 832 are arranged such that their centers (not shown) are disposed on an imaginary straight line 860 (the imaginary line 860 is not part of the test pattern 830, is not shown to the patient, and is shown solely for illustrative purposes to indicate the arrangement of the segments included in the test pattern 830).

The test pattern 830 includes additional segments which are not shown for the sake of clarity of illustration. The test pattern 830 is artificially distorted as disclosed hereinabove. The test pattern 830 includes segments 840, 842, and 844. The centers of the segments 840, 842 and 844 are offset from the imaginary line 860.

The dashed line 853 which starts at the center 842C of the segment 842 is perpendicular to the line 860, and intersects the line 860 at the point $P_{C1}$. The point 850 schematically represents a position marked by the patient (on the display on which the test pattern 830 is presented) in response to the presentation of the test pattern 830. The dashed line 855 which starts at the point 850 is perpendicular to the line 860, and intersects the line 860 at the point $P_{M1}$.

The double headed arrow labeled D7, represents the distance D7 between the points $P_{C1}$ and $P_{M1}$ along the line 860. If the distance D7 is equal to or greater than 2.83° (expressed as the cone angle at a distance of 50 centimeters of the tested eye from the display screen on which the test pattern 830 is displayed), the position of the marked point 850 is defined as being due to a PROD. If the distance D7 is smaller than 2.83°, the position of the marked point 850 is defined as being due to an AIOD.

Using the above disclosed exemplary (non-limiting) criteria, a patient's response to the presentation of a test pattern including an AD in which at least one marked position was defined as being due to a PROD, is recorded as a P type response, and a patient's response to the presentation of a test pattern including an AD in which at least one marked position was defined as being due to a PROD and at least one other marked position is defined as being due to an AIOD, is recorded as a B type response.

It is noted that the criteria illustrated in FIGS. 13 and 14 for classification patient responses as B type or P type responses, are general criteria which may be applied to all the specific positions of the artificial distortion within a test pattern, and to the different possible positions which may be marked by the patient in response to the presentation of a specific test pattern including an AD at a particular position. These criteria may be applied to responses presented at various different locations on the display device, as disclosed in detail hereinabove, and test patterns having ADs with different heights It is further noted, that while the criteria disclosed hereinabove for distinguishing between a marked position due to a PROD and a marked position due to an AIOD are schematically illustrated for an example (FIG. 13) in which the segments 740, 742, and 744, included in the artificial distortion, are offset above the line 760 (such an AD is defined as an upward curving AD hereinafter), the same criteria may also be applied to responses generated by test patterns (not shown) having an artificial distortion in which the segments are offset below the line 760 (such an AD is defined as a downward curving AD hereinafter).

Similarly, the criteria disclosed hereinabove may be similarly applied for responses to test patterns such as the exemplary test pattern 830 of FIG. 14 including the segments 840, 842, and 844 of the test pattern 830 of FIG. 14 in which the segments 840, 842, and 844 of the AD are offset to the left of the line 860 (such an AD is defined as a left curving AD hereinafter) and to test patterns (not shown) having an artificial distortion with segments which are offset to the right of the line 860 (such an AD is defined as a right curving AD hereinafter).

In all of the presentations of all the test patterns including an AD of EXPERIMENT 1, the direction of curvature of the artificial distortion was randomized. Thus, for horizontal test patterns including an AD the probability that the AD in the presented test pattern is an upward curving AD was equal to the probability that the AD is a downward curving AD (and both of these probabilities were equal to 0.5). Similarly, for vertical test patterns including an AD the probability that the AD in the presented test pattern is a right curving AD was equal to the probability that the AD is a left curving AD (and both of these probabilities were equal to 0.5).

It is, however, noted, that the direction of the curvature of the AD need not be randomized in the artificially distorted test patterns which are presented to a patient within a test. Moreover, it was experimentally discovered, in later experiments, that the direction of curvature of the distortions observed by patients in response to the presentation of linear (distorted or non-distorted) test patterns, depends on the direction of movement of the test pattern (in tests using the "moving pattern" method disclosed hereinabove), or on the direction of the presented test pattern relative to the fixation target (in tests using the flash method disclosed hereinabove).

Typically, the PROD observed by the patients was reported to be curved in the same direction of "movement" of the test pattern (in tests using the moving pattern method), and in the direction pointing from the fixation point toward the flashed test pattern (in tests using the flash method). In other words, the distorted part of the test pattern as observed by the patient seemed to be offset (protruding) from the test pattern in the direction of the "movement" of the test pattern (in tests using the moving pattern method), and in the direction pointing from the fixation point toward the flashed test pattern target (in tests using the flash method).

Thus, in accordance with another embodiment of the invention, it may also be possible to use in the tests ADs in which the distorted part of the test pattern (the AD) presented to the patient is offset (protruding) from the test pattern in the direction of the "movement" of the test pattern (in tests using the moving pattern method), and in the direction pointing from the fixation point toward the flashed test pattern target (in tests using the flash method).

Furthermore, in accordance with yet another embodiment of the invention, it may also be possible to use in the tests ADs in which the distorted part of the test pattern (the AD) presented to the patient is offset (protruding) from the test pattern in a direction opposite to the "movement" of the test pattern (in tests using the moving pattern method), or opposite to the direction pointing from the fixation point toward the flashed test pattern target (in tests using the flash method).

After determining the response types for all of the patient's responses evoked by the presentation of test patterns including an AD, the computer further calculates the following parameters. For all of the test patterns including an AD with the same height, the computer computes the values $R_H$, and $B_H$, wherein $R_H$ is the percentage of responses classified as P type responses out of the total number of test patterns including an AD with a height H which were presented to the patient, and wherein $B_H$ is the percentage of responses classified as B type responses out of the total number of test patterns including an AD with a height H which were presented to the patient.

For example, if the patient was presented with 60 test patterns having an artificial distortion with a height H=0.22° (represented as degrees of the cone angle for a distance of 50 centimeters of the tested eye from the display on which the test patterns are presented), and 6 responses out of all the patient's responses to the presentation of these 60 test patterns were classified as P type responses, then $R_{0.22}$=10%. For the same patient presented with the above indicated 60 test patterns having an artificial distortion with a height H=0.22°, if three responses out of all the patient's responses to the presentation of these 60 test patterns were classified as B type responses, then $B_{0.22}$=5%.

The computer then further calculated the value of the competition grade $C_H$ for an artificial distortion having a height H, wherein $C_H = R_H + B_H$.

For example, for the above exemplary test of the same patient for which $R_{0.22}$=10% and $B_{0.22}$=5%, the value of $C_{0.22}$ is $C_{0.22}$=10%+5%=15%. Thus, for this particular test of the above exemplary (hypothetical) patient, the competition grade for an artificial distortion having a height of 0.22°, is 15 percent.

After performing various different empirical calculations based on the analysis of results of the patients tested in EXPERIMENT 1, the following criteria were selected for determining if the patient belongs to the group with normal retina, or belongs to the group having AMD with HRC, based on the results of the test patterns having ADs with a height of 0.19° (it is noted that the data from the results of the test patterns having ADs with a height of 0.22° were not used for establishing these criteria):

A patient belongs to the group with high risk characteristics AMD (AMD with HRC group) if at least one of the following two conditions is satisfied:
1) $P_F > 10\%$
2) $C_{0.19} > 7\%$ wherein $P_F$ and $C_{0.19}$, are as defined in detail hereinabove.

If none of the above two criteria is satisfied, the patient belongs to the group having normal retinas (normal group).

When these classification criteria are applied to the test results of all the patients tested in EXPERIMENT 1, the results were as indicated in TABLE 1 below.

TABLE 1

|  | Patients ophtalmologically diagnosed as having AMD with HRC | Patients ophtalmologically diagnosed as having Normal retinas | Total |
| --- | --- | --- | --- |
| Patients which satisfy at least one of the conditions: $P_F > 10\%$ $C_{0.19} > 7\%$ | 28 | 2 | 30 |
| Patients which do not satisfy any of the conditions: $P_F > 10\%$ $C_{0.19} > 7\%$ | 4 | 26 | 30 |
| Total | 32 | 28 | 60 |

Calculated sensitivity 87.5%
Calculated specificity 93%
P < 0.001

Experiment 2

In this experiment, two groups were tested. The first group included 43 subjects clinically diagnosed to have AMD with high risk characteristics (AMD with HRC group). The second group included 20 subjects clinically diagnosed to have CNV. All subjects (in the age range of 50–90 years old) were given a complete eye examination by a retina specialist prior to performing the tests for the experiment. After the diagnosis was recorded by the retina specialist each of the patient was tested using an MCPT adapted for the experiment as disclosed hereinafter.

The artificial distortions presented were selected from artificial distortions (AD) having a height of 0.19°, 0.22°, and 0.28° as disclosed hereinabove. Each test pattern had a dimension of approximately 14°. Half of the test patterns presented to each patient, were generally horizontally oriented and the other half were generally vertically oriented, as disclosed hereinabove. Altogether, the test patterns were adapted to map a 14°×14° grid on the macula with a 1° resolution. The fovea of the tested eye was at the center of the mapped region. The sequence of presentation of the horizontal and vertical test patterns within a single test was randomly selected. The sequence of presenting signals with an AD and without an AD was also randomized. The sequence of presentation of the test patterns having different heights (selected from heights of 0.19°, 0.22°, and 0.28°) was also randomized, as disclosed hereinafter.

In all of the presentations of all the test patterns including an AD of EXPERIMENT 2, the direction of curvature of the artificial distortion was randomized. Thus, for horizontal test patterns including an AD the probability that the AD in the presented test pattern is an upward curving AD was equal to the probability that the AD is a downward curving AD (and both of these probabilities were equal to 0.5). Similarly, for vertical test patterns including an AD the probability that the AD in the presented test pattern is a right curving AD was equal to the probability that the AD is a left curving AD (and both of these probabilities were equal to 0.5).

Each eye was tested by presenting test patterns at thirty different locations on the display of the laptop computer. Fifteen locations were horizontally oriented on the display of the laptop computer and fifteen locations were vertically oriented on the display of the laptop computer. At each of the thirty different locations on the display of the laptop computer there were three (3) randomized presentations of the test patterns, one presentation of a test pattern with no AD (a flat test pattern), each of the two other presentations of a test pattern at the location included an AD. Altogether, each test included 90 presentations of test patterns to the tested patient's eye.

The height of the AD in each of these two remaining presentations was randomly selected from the heights 0.19°, 0.22°, and 0.28° without repetition (without repetition means herein that the two ADs presented at the same location were always of different heights). It is noted that since only two (out of three possible) different heights of AD were used in the test patterns presented at the same location and orientation, the data for each specific location and orientation of a test pattern did not include all possible AD heights.

In the two test pattern presentations including an AD, the position within the test pattern of the three segments forming the AD was randomly selected, but the minimal distance between the positions of the AD in the two presentations was 5°, as explained in detail for EXPERIMENT 1 hereinabove.

The patients were asked to mark the positions at which a distortion was observed, by using a mouse connected to the Laptop computer as disclosed in detail hereinabove for the flash test. All the test data were stored in the laptop computer for further processing and analysis, as disclosed in detail for EXPERIMENT 1 hereinabove.

The results of EXPERIMENT 2 were then processed as follows. The computer analyzed the position of the markings by the patient in response to the presentation of test patterns having an AD, and classified the responses as follows. Turning back to FIGS. 13 and 14, for horizontal test patterns if the distance D6 (FIG. 13) is smaller than 2.83°, the position of the marked point 750 is defined as being due to an AIOD. Similarly, for vertical test patterns, if the distance D7 (FIG. 14) is smaller than 2.83°, the position of the marked point 850 is defined as being due to an AIOD.

If, in response to the presentation of a test pattern including an AD, all the positions marked by the patient are defined to be due to an AIOD using the definition as disclosed hereinabove, the response is classified as an A type response (indicating that all of the positions marked by the patient are considered to be due to an AIOD).

After determining the response type for all of the patient's responses evoked by the presentation of test patterns including an AD, the computer further calculated the following parameters. For all of the test patterns including an AD with the same height H, the computer computed the value $A_H$, wherein $A_H$ is the percentage of responses classified as A type responses out of the total number of test patterns presented to the patient which contained an AD with a height H.

For example, if the patient was presented with twenty (20) test patterns having an artificial distortion with a height of H=0.28° (represented as degrees of the cone angle for a distance of 50 centimeters of the tested eye from the display on which the test patterns are presented), and five (5) responses out of all the patient's responses to the presentation of these twenty test patterns were classified as A type responses, then $A_{0.28}$=25%.

After performing various different empirical calculations based on the analysis of results of the patients tested in EXPERIMENT 2, the following criterion was selected for determining if the patient belongs to the group having CNV, or belongs to the group having AMD with HRC, based on the results of the test patterns having ADs with a height of 0.28° (it is noted that the data from the results of the test patterns having ADs with heights of 0.19° and 0.22° was not used for establishing the criterion below):

A patient belongs to the group with CNV if $A_{0.28}$<75%

If $A_{0.28} \geq 75\%$, the patient belongs to the group having high risk characteristics AMD (AMD with HRC group).

When this patient classification criterion is applied to the test results of all the patients tested in EXPERIMENT 2, the results were as indicated in TABLE 2 below.

TABLE 2

|  | Patients ophtalmologically diagnosed as diagnosed as having CNV | Patients ophtalmologically diagnosed as having AMD with HRC | Total |
|---|---|---|---|
| Patients for which $A_{0.28}$ < 75% | 18 | 6 | 24 |
| Patients for which $A_{0.28} \geq 75\%$ | 2 | 37 | 39 |
| Total | 20 | 43 | 63 |

Calculated sensitivity 90%
Calculated specificity 85%
P < 0.001

It will be appreciated by those skilled in the art that the specific classification criteria disclosed hereinabove for classifying patients as belonging to specific different AMD disease progression groups, are given by way of example only and are not intended to limit the scope of the invention. Other different criteria may be empirically determined and used by modifying or fine tuning the parameters of the test or the parameters of the test patterns used in the test. Systematically varying one or more of the parameters of the test or of the test patterns used therein may be therefore used to fine tune or improve or optimize the test to yield better or improved classification criteria. Such systematic variations are known to those skilled in the art, and are therefore not described in detail hereinafter.

It is noted that while in the non limiting examples of the embodiments of the competition method of the present invention which are described in EXPERIMENT 1 and EXPERIMENT 2 disclosed hereinabove, the data used for distinguishing or classifying the tested individuals into different groups was taken from a group of test patterns having an AD of a certain selected height (the group of data obtained using test patterns with ADs having a height H=0.19 in EXPERIMENT 1 and the group of data using test patterns with ADs having a height H=0.28 in EXPERIMENT 2), this is not mandatory and other embodiments of the present invention may use different or additional classification criteria based on processing of the results obtained from the presentation of test pattern groups having different artificial distortion heights.

For example, in accordance with other possible embodiments of the invention it may be possible to use classification criteria which use data from more than one group of test patterns having ADs of different heights. For example, using the data obtained in EXPERIMENT 2, one may use a classification criterion that classifies a patient as having AMD with HRC if $A_{0.28} \geq m$ and $A_{0.22} \geq n$, and classifies the patient as having CNV if $A_{0.28}<m$ and $A_{0.22}<n$, wherein m and n are percentage values which are empirically determined to give desired or acceptable levels of specificity and sensitivity.

Moreover, other classification criteria may be used which may use the values of $A_H$ computed from results of two or three groups of test patterns presenting ADs with H=0.28, H=0.22 and H=0.19. For example, one may used weighted results in the classification criterion.

An exemplary (non-limiting) form of such criteria using weighted results may be, the patient may be classified as having AMD with HRC if:

$$(\alpha A_{0.28}+\beta A_{0.22}+\gamma A_{0.19}) \geq q$$

and as having CNV if:

$$(\alpha A_{0.28}+\beta A_{0.22}+\gamma A_{0.19}) < q$$

wherein $\alpha$, $\beta$, and $\gamma$ are empirically determined weighting factors, and q is an empirically determined number.

The above criteria and other empirically determined criteria may be used to implement the classification of the tested individuals into groups having different clinical stages of AMD (or other retinal or choroidal pathologies).

It will thus be appreciated that while the results of EXPERIMENT 1 and EXPERIMENT 2 demonstrate that it is possible to classify patients into groups having different clinical stages of AMD by using the responses of the tested patients to the presentation of test patterns having artificial distortions with a single AD height (for example, the test patterns having H=0.19 of EXPERIMENT 1 or the test patterns having H=0.28 of EXPERIMENT 2) it may also be possible to use within a single test patterns having ADs with more than one height or amplitude and to process the patient responses data to classify the tested patients with proper modification of the classification criteria used.

It is noted that while the "competition" method of using different graded distortion magnitudes for assessing the severity, or the magnitude, or the dimensions of a retinal or choroidal lesion may be based on the use of artificial distortions included in the segmented test patterns having different graded distortion heights as disclosed hereinabove, other types of graded artificial distortions having various magnitudes or amplitudes or size may also be used in the present invention.

Furthermore, while the competition tests disclosed hereinabove included the use of linear and distorted segmented test patterns, many other types of test patterns may also be used for implementing embodiments of the present invention, the test patterns may include but are not limited to, non-segmented (continuous) lines like any of the types disclosed hereinabove with respect to the MCPT test, and may include but are not limited to straight lines, curved lines, straight or curved lines having a distorted portion or part, or the like. The parts of the test patterns which are distorted may be curved like part of an elliptical curve, or parabolic curve, or an undulating curve, or any other suitable curve shape that may mimic the appearance of a distortion perceivable by a patient having a retinal lesion. Additionally, the distorted part of the test pattern (irrespective whether the test pattern is segmented or non-segmented) may be configured to have a linear shape, such as for example, a triangular distortion shape, or the like. Moreover, the segments (or alternatively the continuous part of the test pattern) comprising the distortion may be arranged as any desired type of distortion having any suitable shape.

In another example, in accordance with other embodiments of the present invention it may be possible to use artificial distortions with a triangular shape (not shown) having graded heights of the triangle-like distortion, or curved artificial distortions in which the segments of the artificial distortion are arranged along non-linear curves other than an ellipse and having graded curve parameters. Such non-linear curves may include but are not limited to parabolas, irregular curves, and curves having multiple extremum points.

Thus, the shapes, curvature, dimensions and magnitudes of the artificial distortions disclosed hereinabove, illustrated in the drawing figures and used in the experiments, are given by way of example only and are not obligatory to practicing the invention. It is therefore noted that many other types of artificial distortions and test patterns having other different parameters may also be used in practicing the invention all of which are considered to be included within the scope of the present invention.

It is noted that while the distortion type used in EXPERIMENT 1 and EXPERIMENT 2 is symmetrical (with respect to the minor axis of the half ellipse curve 662 used for determining the position of the center points 640C and 644C of the segments 640 and 644, respectively, illustrated in FIG. 12), the distorted part of the curve need not necessarily be symmetrical. Thus, the distortion types usable in different embodiments of the present invention (irrespective of whether the test pattern is segmented or non-segmented) may be a symmetrical distortion or a non-symmetrical distortion.

For example, possible embodiments of the methods and test patterns of the invention it may include, inter alia, embodiments in which one or more of the following test parameters may be varied: the number of segments in the test patterns, the segment size and/or shape (for example, circular shapes may be used instead of square segments), the segment shape, the distance between segments, the size and/or shape and/or amplitude, and/or the longitudinal dimension of the artificial distortion along the test pattern (the width of the distortion), and/or curvature of the artificial distortion (including the curvature degree and/or curvature direction of the artificial distortion), the color and/or luminosity, of the test patterns and/or of the background on which the test patterns are displayed or presented to the patient, the sequence of presentation of the test patterns (including fixed sequences, random sequences, and pseudo-random sequences of test pattern presentations), the positioning of the AD within the test pattern, the AD magnitudes or amplitudes used in the test, the duration of presentation of the test pattern to the patient in the flash method, the method of position marking used by the patient for reporting the position of the observed distortions, the number, type, and sequence of the test patterns included in a test, or the like.

It will be appreciated by those skilled in the art that if one or more of the parameters of the test patterns or of the artificial distortions used are modified, the methods and criteria used for processing the data and for analyzing the results may have to be adapted to the changes made.

For example, in accordance with one possible embodiment of the present invention, the artificial distortions used may be graded according to their width or longitudinal dimension along the test pattern. Returning briefly to FIGS. 12–14, the artificial distortions may also graded by graded changing of the longitudinal dimension of the artificial distortion along the test pattern. For example, the distance MA (FIG. 12) may be varied in a graded manner in different ADs instead of the distance H (FIG. 12). In such a case it may be necessary to adapt the distance from the center of the AD which is used as a criterion to decide if a position marked by the tested individual is assumed to be due to the artificial distortion (or defined as an AIOD as disclosed in detail hereinabove).

For example, in accordance with one possible embodiment of the invention, one may use three different ADs in a test. All the ADs used have the same distance H (such as, but not limited to, 0.22°), but each AD may have one of three possible values of the distance MA, such as, but not limited to, 1.92°, 2.62°, and 3.32°. This may be achieved, for example, by displacing three, five, and seven segments of the test pattern 630 respectively, vertically above the line 660 of FIG. 12, using a suitable half ellipse curve, or by suitably increasing the distance D4 between the segments 638, 640, 642, 644, and 646 without changing the distance between each of the segments 640 642 and 644 and the straight line 660, or by any suitable combination of the above exemplary methods, or by any other method for increasing the width or longitudinal dimension (on the axis labeled X of FIG. 12) of the AD along the test pattern 630.

In such a case, it may be desired to modify the criterion of distance of the marked position from the center point of the AD for each of the three different graded forms of the AD. For Example, the criterion distance for ADs having MA=1.92° may be 2.83° as disclosed above, while the criterion distance used for ADs having MA=2.62°, and MA=3.32° may be 3.53°, and 4.23°, respectively (all cone angles assuming a distance of approximately 50 centimeters from the tested eye and the screen 112).

Similarly, if any other parameters of the test patterns are changed, or the type and/or density of the grid which they may form on the retina if they were all simultaneously projected thereon are changed, it may or may not be necessary to suitably change or adapt the processing of the data, such as, but not limited to, the proximity criteria used for processing the responses to pairs of test patterns projected, or the like.

Furthermore, it will be appreciated by those skilled in the art that while the shape and dimensions of the ADs used in the experiments may be computed or determined using mathematical methods for constructing the test patterns including ADs (such as in the exemplary embodiment for computing of the position of the center points of the segments 640 642 and 644 of FIG. 12 using a half ellipse curve computation), it may also be possible to use test patterns having ADs which are empirically found to give a satisfactory sensitivity and selectivity in classification studies similar but not identical to the studies disclosed in EXPERIMENT 1 and EXPERIMENT 2 above.

In such studies one may possibly test many different types of arbitrarily or non-computationally created artificial distortions in order to empirically define a set of ADs which yields satisfactory classifications of AMD stages. Such artificial distortions may be constructed to differ one from the others in shape or dimensions or color or any other single or multiple characteristics of the ADs.

For example, if one uses within the same test an ellipsoidaly shaped AD, a triangularly shaped AD and a rectangularly shaped AD, and it is found that each of these ADs has a different efficacy as a competing stimulus, such AD combinations may also be practically used in the classification tests of the present invention.

It is noted that it may also be possible to use in the tests of the present invention ADs in which the AD may include arbitrarily selected changes in any visually perceivable characteristic(s) of the test pattern or of parts thereof. Such changes may be in the color or brightness or blurriness or in any other suitable perceivable characteristic of the test pattern or part thereof, as long as the used sets of AD have been empirically tested and proven to give satisfactory performance is clinical tests in humans with eye disease.

Moreover, while the precise mechanism underlying the competition phenomenon disclosed herein is not known, it may be possible that when the patient is simultaneously presented with multiple stimuli, there is a "competition for attention". It may therefore be possible that when a patient is simultaneously exposed to multiple sensory stimuli there is a certain probability that the more prominent or noticeable or larger stimulus will be preferentially noticed (and therefore preferentially reported by the patient).

When the two stimuli are of the same sensory modality, such as for example in the cases in which a test pattern including an AD is projected on a retinal position having a retinal lesion, the perceived distortion which is of a larger magnitude or which is more noticeable or perceived as larger or more prominent may be statistically preferentially perceived by the patient (and therefore may be statistically preferentially reported by the patient).

It may therefore be possible, in accordance with additional embodiments of the present invention to use in the "competition method" other different types of sensory stimuli for competing with the PROD, including but not limited to, visual stimuli, auditory stimuli, somatosensory stimuli (including but not limited to various temperature stimuli, touch stimuli, pressure stimuli, itch stimuli, or the like), kinesthetic stimuli such as moving various different limbs or digits or other organs, various different pain stimuli, or any other suitable sensory stimuli having various different modality.

Such sensory stimuli of various differing sensory modalities are generally referred to as competing stimulus (CS) hereinafter. In the present application, the definition of a competing stimulus is any sensory stimulus which may be delivered or applied or presented to a tested patient and which may affect the probability that the patient will report a PROD when a test pattern is presented to the patient at a location such that the image of the test pattern is projected on a lesioned retinal or choroidal region.

The different sensory stimuli may be administered or applied or presented to the patient before and/or simultaneously with the presentation of the visual test patterns disclosed hereinabove in detail or with the presentation of other suitable different visual test patterns. These different sensory stimuli may possibly function as "distracting stimuli" or as "competing stimuli" that compete for patient's attention for obtaining results which are similar (though not necessarily identical) to the results of the competition experiments using visual AD's as disclosed hereinabove.

Additionally, one or more of the parameters of these additional sensory stimuli may be varied systematically or graded in different presentations of the stimuli. By varying one or more of the parameters of the additional sensory stimuli presented with or before or after the primary visual test patterns (such as, but not limited to the linear segmented test pattern 322 of FIG. 3, or the test patterns 382 of FIG. 5B disclosed hereinabove), and by recording and analyzing the patient's responses, it may be possible to empirically establish classification criteria for diagnosing a patient as belonging to a group with a defined stage of the disease. For example, using such criteria it may be possible to distinguish between different clinically distinguishable stages of AMD (such as but not limited to the different AMD stages disclosed hereinabove in EXPERIMENT 1 and EXPERIMENT 2).

It will be appreciated by those skilled in the art that such criteria may be different than the empirical criteria disclosed hereinabove for the use of artificially distorted test patterns disclosed for EXPERIMENT 1 and EXPERIMENT 2 hereinabove.

Thus, in accordance with one exemplary embodiment of the invention, the distracting stimulus may be an auditory stimulus. For example, the patient may perform a modified version of an MCPT test in which an auditory stimulus may be delivered to the patient before, during, or after the presentation of a visual test pattern. The auditory stimulus may be delivered to the patient by using earphones (not shown) or suitable speakers, or the like. The auditory stimulus may be in the form of a click, or a beep, or a pure sine wave having a finite duration, or a telephone-like ringing, or any other suitable type of auditory stimulus known in the art. The auditory signal may be delivered to the patient before, during, or after the presentation of a test pattern (the test pattern may or may not include an AD) to a tested eye of the patient. If the test pattern is presented at a location such that the patient may perceive a PROD, the delivery of the auditory stimulus may distract the patients attention. By repeating the presentation of the test pattern together with the auditory stimulus, varying (grading) one or more of the parameters of the auditory stimulus delivered, and recording the patient's responses to the presentation of the test stimuli it may be possible to analyze the competition of the auditory stimulus with the PROD and to empirically determine classification criteria for various AMD stages, or for other stages of other different retinal pathologies or diseases.

The parameters of the auditory stimulus that may be varied (graded) in different presentations of test patterns may be but is not limited to one or more of the amplitude, duration, frequency (or frequency range and content for stimuli including a range of frequencies), or waveform of the auditory stimulus. Additionally, it may be possible to use a group of different auditory stimuli which are empirically selected on the basis of having different psychophysical efficacy as distracting or competing stimuli.

Experiment 3

This experiment was performed to test different types of auditory stimuli for their efficacy as competing stimulus (CS), in accordance with yet another embodiment of the present invention. The study included three tested individuals having normal retinas (as ascertained by full ophtalmological examination as disclosed hereinabove). Each one of the tested individuals was subjected to five different tests (designated as tests 1–5). Each of the tests 1–5 included presenting a total of thirty eight (38) test patterns to the tested individual using the flash method as disclosed in detail hereinabove. The test patterns were segmented straight lines as disclosed in detail hereinabove for EXPERIMENT 2. Of the thirty eight test patterns presented in each test, nineteen test patterns were vertical and the other nineteen test patterns were horizontal. Each of the 38 test patterns included an AD having a height of 0.12°, as disclosed hereinabove. The position of the AD within the test pattern was randomized using an LUT as disclosed hereinabove.

Figure 15:
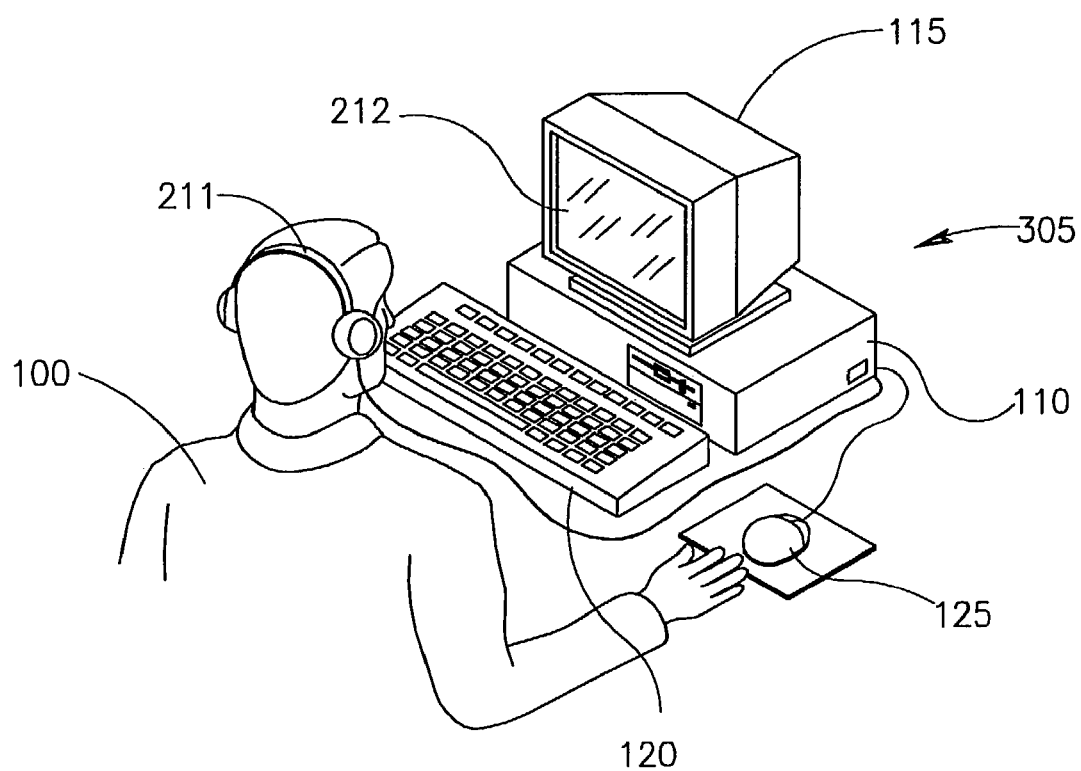
FIG. 15 is a schematic diagram illustrating is a schematic diagram illustrating a system for carrying out an eye test to detect and or assess an eye disease using auditory competing stimuli in accordance with another embodiment of the present invention.

Reference is now made to FIG. 15 which is a schematic diagram illustrating a system useful for carrying out an eye test to detect and or assess an eye disease using auditory competing stimuli in accordance with another embodiment of the present invention. The system 305 is similar to the system 105 disclosed hereinabove, except that the screen 212 of the display device 115 was a touch sensitive screen, and the tested subject 100 marked the positions of the ADs or other perceived differences on the screen 212 using his finger instead of using the mouse 125, and that the system 305 also included a stereophonic headphones set 211.

For the duration of the tests, the tested subject 100 was wearing the headphones set 211. In all the tests performed in EXPERIMENT 3 and EXPERIMENT 4, the headphones set 211 were model MDR-305 stereophonic headphones, commercially available from Sony Corp., Japan.

It is, however noted, that any other suitable sound source may be_used for performing the method of the present invention, including but not limited to monoaural sound sources, single earphones worn by the tested individual, various types of loudspeakers such as one or more loudspeakers which are built into or form part of the computer system 105 or 305, one or more loudspeakers positioned in the room in which the individual 100 is being tested, or any other single or multiple sound sources known in the art.

The headphones set 211 were suitably connected to the line output of the sound card (not shown) installed in the computer 110. The computer 110 in this study was a Dell Latitude Laptop computer, model C600 commercially available from Dell Computer Corporation U.S.A, and the operating system was the Microsoft Windows 2000 Professional (Version 5.0.2195 Service Pack 1, Built 2195) commercially from Microsoft Corporation, U.S.A. During all tests the distance between the screen 212 and the tested eye was approximately 50 centimeters.

The sound card used for the production of the CS was the onboard sound card hardware provided with the Dell Latitude C600 laptop computer (ESS Maestro PCI audio, from Engineering Software Services companies Fl, U.S.A). All Sound measurements were performed using the "Environmental noise measurement system" software (version 3.1.1.2) commercially available from Yoshimasa Electronic Inc., Japan, using the sound pressure level (SPL) measurement mode.

For measuring the sound pressure levels, a model MIC111 Maxxtro omni-directional microphone was used (commercially available from Gembird Electronics Ltd., Hong Kong). The microphone had a frequency response of 15 Hz–13 KHz, an impedance of >2,200 Ohms, and a sensitivity of 58 dB±2 dB. The microphone was connected to the line-in audio input jack of the laptop computer and the microphone was placed between the two earphones at a distance of approximately 3 millimeters from each earphone.

In two of the tests conducted (TEST 1 and TEST 3) no sound was used during the test. These tests served as control tests.

In TEST 2, TEST 4 and TEST 5, sound was used as a competing stimulus (CS). The test pattern presentation duration was 160 milliseconds as disclosed hereinabove. The duration of the sound used as the auditory CS was 900 milliseconds. The auditory CS started at the time of presentation of the test pattern and ended 740 milliseconds after the end of the presentation of the test pattern on the screen 212.

Three different auditory CS types were used. In TEST 2 the auditory CS was a sound having an increasing pitch (defined as sound type 1). Sound type 1 was obtained by playing through the headphones set 211 the sound file "SOUND20.WAV" taken from the Windows XP® sound library. The file was played as the auditory CS through the headphones set 211 at a sound pressure level of 40 dB.

In TEST 4 the auditory CS was a synthesized telephone ring-like sound (defined as sound type 2) Sound type 2 was obtained by playing through the headphones set 211 the sound file "RINGIN.WAV" taken from the Windows XP® sound library. The intensity of the auditory CS was 40 dB.

In TEST 5 the auditory CS was a synthesized sound of electronic drums which was panned as if moving from the right side to the left side in space, by changing the sound intensity in the left and right earphones of the headphones set 211 (defined as sound type 3). Sound type 3 was obtained by playing through the headphones set 211 the sound file "TestSnd.wav" taken from the Windows XP® sound library. The sound pressure level of the auditory CS was 40 dB.

In all tests the subject 100 was requested to mark all the perceived distortions in all the test patterns as disclosed in detail hereinabove. The tested subject marked the perceived distortions by touching the touch sensitive screen 212 with his finger at the position at which a distortion or a difference or deviation from a reference segmented straight line was perceived.

The following parameters were recorded for analysis. A response in which the presented AD was detected and correctly marked (according to the criteria as disclosed hereinabove for EXPERIMENTS 1 and 2) is recorded as "FOUND".

A response in which the presented AD was not detected by the tested subject 100 (according to the criteria as disclosed hereinabove for EXPERIMENTS 1 and 2) is recorded as "NOT FOUND".

A response in which the position marked by the tested subject 100 was far from the location of the center of the AD (the criterion used here was when the position marked was at a cone angle of more than 2 degrees from the center of the AD) is referred to as "REAL", indicating that the tested subject did observe a distortion or difference which is assumed not to be due to the presence of the AD presented in the test pattern.

In analyzing the results, a "competition index" $C_I$ was defined as follows, $$C_I = F/(NF+R)$$

Wherein, $C_I$ is the competition index for sound type I (for example, $C_1$ is the competition index for sound type 1, $C_2$ is the competition index for sound type 2, etc.), F represents the number of test pattern presentations in the test for which a "FOUND" response was recorded, NF represents the number of test pattern presentations in the test for which a "NOT FOUND" response was recorded, and R represents the number of test pattern presentations in the test for which at least one "REAL" response was recorded.

Higher values of $C_I$ indicate a higher percentage of correct identifications of the artificial distortions, while lower values of $C_I$ indicate a lower percentage of correct identifications of the artificial distortions.

The raw data of all test results in EXPERIMENT 3 is shown in TABLE 4 below.

In TABLE 4, the first column lists the tested subject number (test subjects 1, 2, and 3). The second column indicates the test number. For the column group labeled "Found", the sub-column labeled H represents the number of horizontal test patterns for which a "Found" result was recorded in the test indicated in the appropriate row, the sub-column labeled V represents the number of vertical test patterns for which a "Found" result was recorded in the test indicated in the appropriate row, and the sub-column labeled T represents the total number of test patterns (horizontal and vertical) for which a "Found" result was recorded in the test indicated in the appropriate row.

Similarly, for the columns group labeled "Not Found", the sub-column labeled H represents the number of horizontal test patterns for which a "Not Found" result was recorded in the test indicated in the appropriate row, the sub-column labeled V represents the number of vertical test patterns for which a "Not Found" result was recorded in the test indicated in the appropriate row, and the sub-column labeled T represents the total number of test patterns (horizontal and vertical) for which a "Not Found" result was recorded in the test indicated in the appropriate row, and for the columns group labeled "Real", the sub-column labeled H represents the number of horizontal test patterns for which a "Real" result was recorded in the test indicated in the appropriate row, the sub-column labeled V represents the number of vertical test patterns for which a "Real" result was recorded in the test indicated in the appropriate row, and the sub-column labeled represents the total number of test patterns (horizontal and vertical) for which a "Real" result was recorded in the test indicated in the appropriate row.

The columns labeled R+NF and F/(NF+ R) show the values of these expressions (calculated as disclosed in detail hereinabove) for the test indicated in the appropriate row.

Summary of the Results of Experiment 3

The raw results shown in TABLE 4 above were further pooled and averaged as shown below.

1. The value of the pooled competition index for all the tests with no auditory competing stimulus was calculated as follows, the results from TEST 1 and TEST 3 (the tests with no auditory competing stimuli) of all three test subjects (tested subjects 1,2, and 3), and the computed $Q_I$ values for all six tests were averaged. The resulting mean was 3.23±0.77 (Mean±S.D.; n=6 tests).

2. The value of the pooled competition index for all the tests in which auditory competing stimuli was presented was calculated as follows: The results from TEST 2, TEST 4 and TEST 5 (the tests with auditory competing stimuli) of all three test subjects (tested subjects 1,2, and 3), and the $Q_I$ values for all nine tests were averaged. The resulting mean was 2.16±1.38 (Mean±S.D.; n=9 tests).

The results for each one of the tests (TEST 1–TEST 5) were also averaged by averaging the competition index calculated for all three tested subject as follows:

3. The value of the calculated competition indexes for TEST 1 (no auditory competing stimulus) was averaged for all three tested subjects (tested subjects 1,2, and 3). The computed $Q_I$ values for the tests were averaged. The resulting mean was 3.37±0.77 (Mean±S.D.; n=3 tests).

4. The value of the pooled competition index for all the tests in which the presented auditory competing stimuli number was Sound type 1 was calculated as follows: The results from TEST 2 (the test in which the auditory competing stimulus was sound type 1) for all three test subjects (tested subjects 1–3) were averaged, and the mean $Q_I$ value for TEST 2 in all three subjects was 2.27±1.1 (Mean±S.D.; n=3 tests).

5. The value of the calculated competition indexes for TEST 3 (no auditory competing stimulus) was averaged for all three tested subjects (tested subjects 1,2, and 3). The computed $Q_I$ values for the tests were averaged. The resulting mean was 3.10±0.67 (Mean±S.D.; n=3 tests).

6. The value of the pooled competition index for all the tests in which the presented auditory competing stimuli number was Sound type 2 was calculated as follows: The results from TEST 4 (the test in which the auditory competing stimulus was sound type 2) of all three test subjects (tested subjects 1–3), and the $Q_I$ values for all three tests were averaged. The resulting mean was 1.88±0.86 (Mean±S.D.; n=3 tests).

7. The value of the pooled competition index for all the tests in which the presented auditory competing stimuli number was Sound type 3 was calculated as follows: The results from TEST 5 (the test in which the auditory competing stimulus was sound type 3) of all three test subjects (tested subjects 1–3), and the $Q_I$ values for all three tests were averaged. The resulting mean was 2.32±2.04 (Mean±S.D.; n=3 tests).

To summarize, the results of EXPERIMENT 3 demonstrate that auditory stimuli of different types may reduce the ability of the tested individual to perceive and/or report an artificial distortion in a visually presented test pattern. The mean competition index for all tests without an auditory competing stimulus (no sound), is 3.23±0.77 (Mean±S.D.; n=6 tests) as compared to a lower value of 2.16±1.38 (Mean±S.D.; n=9 tests) in the tests in which a competing auditory stimulus was presented to the tested subject. It may also be seen from the above presented results that different

TABLE 4

| Tested Subject and Test Number | "Found" | | | "Not Found" | | | "Real" | | | R + NF | F/ (NF + R) |
|---|---|---|---|---|---|---|---|---|---|---|---|
| | H | V | T | H | V | T | H | V | T | | |
| 1. test 1 | 19 | 12 | 31 | 0 | 3 | 3 | 0 | 4 | 4 | 7 | 4.43 |
| test 2 | 14 | 14 | 28 | 1 | 1 | 2 | 4 | 4 | 8 | 7 | 4.00 |
| test 3 | 17 | 14 | 31 | 0 | 0 | 0 | 2 | 5 | 7 | 10 | 3.10 |
| test 4 | 14 | 14 | 28 | 0 | 0 | 0 | 5 | 5 | 10 | 10 | 2.80 |
| test 5 | 17 | 14 | 31 | 1 | 1 | 2 | 1 | 4 | 5 | 7 | 4.43 |
| 2. test 1 | 15 | 14 | 29 | 1 | 5 | 6 | 3 | 0 | 3 | 9 | 3.22 |
| test 2 | 16 | 9 | 25 | 3 | 10 | 13 | 0 | 0 | 0 | 13 | 1.92 |
| test 3 | 14 | 16 | 30 | 1 | 1 | 2 | 4 | 2 | 6 | 8 | 3.75 |
| test 4 | 10 | 10 | 20 | 5 | 7 | 12 | 4 | 2 | 6 | 18 | 1.11 |
| test 5 | 2 | 8 | 10 | 13 | 10 | 23 | 4 | 1 | 5 | 28 | 0.36 |
| 3. test 1 | 12 | 15 | 27 | 4 | 1 | 5 | 3 | 3 | 6 | 11 | 2.45 |
| test 2 | 10 | 8 | 18 | 7 | 5 | 12 | 3 | 5 | 8 | 20 | 0.90 |
| test 3 | 14 | 13 | 27 | 5 | 3 | 8 | 0 | 3 | 3 | 11 | 2.45 |
| test 4 | 14 | 10 | 24 | 5 | 6 | 11 | 0 | 3 | 3 | 14 | 1.71 |
| test 5 | 12 | 14 | 26 | 6 | 3 | 9 | 1 | 2 | 3 | 12 | 2.17 | types of auditory stimuli having different characteristics may have different efficacy in competing against the presented visual stimuli (the AD). For example, from the three different types of auditory stimulus, sound type 2 was the most efficient in competing with sound types 1 and 3 have lower efficacy than sound type 2. This was consistent for all three tested subjects.

While the physiological or psychophysical basis for this phenomenon is not presently clearly understood, it may be possible that the different types of sound have different efficacy as distracting stimuli in distracting the attention of the tested subject from the visual stimuli presented in the test. It may therefore be concluded that sounds having various different characteristics may be used for assessing or quantifying the severity of retinal or choroidal lesions or abnormalities.

Experiment 4

This experiment was performed to test the ability of a specific form of auditory competing stimulus presented at different sound intensities to compete in a graded manner with visual stimuli for patient attention in tests requiring the reporting of artificially introduced distortions in visual test patterns.

The same three individuals from EXPERIMENT 3 were tested. The tests in experiment 4 were performed as described in detail for EXPERIMENT 3 hereinabove. Each of the three tested individuals having normal retinas were given three consecutive tests (TEST 6, TEST 7 and TEST 8). Each test included 38 test patterns (19 vertical and 19 horizontal) performed as disclosed for TEST 4 of EXPERIMENT 3, except that the sound pressure levels used were different than the sound intensity used in TEST 4. The auditory CS was Sound type 2, obtained by playing through the headphones set 211 the sound file "RINGIN.WAV" taken from the Windows XP® sound library.

In all the tests included in EXPERIMENT 4 (tests 6, 7 and 8), the duration and the timing of the auditory CS was as disclosed in detail for TEST 4 of EXPERIMENT 3.

In TEST 6 the sound pressure level of the CS was 35 dB, in TEST 7 the sound pressure level of the CS was 45 dB, and in TEST 8 the sound pressure level of the CS was 50 dB.

The raw test results for EXPERIMENT 4 are given in TABLE 5 below, (the column arrangement and abbreviations in TABLE 5 are as described for TABLE 4).

The competition index $Q_I$ was calculated for all tests (as given in the rightmost column of TABLE 5). For each test the computed $Q_I$ values from all three tested individuals were averaged and the results are summarized in TABLE 6 below.

TABLE 5

| Tested Subject and Test Number | "Found" | | | "Not Found" | | | "Real" | | | F/ (NF + R) | (NF + R) |
|---|---|---|---|---|---|---|---|---|---|---|---|
| | H | V | T | H | V | T | H | V | T | R + NF | |
| 1. test 6 | 17 | 13 | 30 | 0 | 4 | 4 | 2 | 2 | 4 | 8 | 3.75 |
| test 7 | 16 | 13 | 29 | 3 | 5 | 8 | 0 | 1 | 1 | 9 | 3.22 |
| test 8 | 14 | 10 | 24 | 4 | 9 | 13 | 1 | 0 | 1 | 14 | 1.71 |
| 2. test 6 | 15 | 8 | 23 | 3 | 5 | 8 | 1 | 6 | 7 | 15 | 1.53 |
| test 7 | 10 | 9 | 19 | 7 | 9 | 16 | 2 | 1 | 3 | 19 | 1.00 |
| test 8 | 8 | 10 | 18 | 10 | 8 | 18 | 1 | 1 | 2 | 20 | 0.90 |
| 3. test 6 | 16 | 15 | 31 | 2 | 2 | 4 | 1 | 2 | 3 | 7 | 4.43 |
| test 7 | 13 | 8 | 21 | 4 | 7 | 11 | 2 | 4 | 6 | 17 | 1.24 |
| test 8 | 11 | 10 | 21 | 6 | 8 | 14 | 2 | 1 | 3 | 17 | 1.24 |

TABLE 6

| TEST NUMBER | Sound Pressure level of Auditory CS | averaged $Q_I$ value for all tested subjects Mean ± S.D. (n = 3) |
|---|---|---|
| TEST 6 | 35 dB | 3.24 ± 1.514 |
| TEST 7 | 45 dB | 1.82 ± 1.221 |
| TEST 8 | 50 dB | 1.28 ± 0.409 |

The results of EXPERIMENT 4 indicate that when a given sound type (specifically, sound type 2) is presented to the tested individuals at different sound pressure levels during the visual testing as described hereinabove, the computed competition index is a function of the sound pressure level of the auditory competing stimulus. As is shown in TABLE 5 and TABLE 6 above, there is a direct correlation between sound pressure level and the ability of the tested individual(s) to correctly report the positions of the AD in the test patterns (in accordance with the specific criteria used in the tests). Thus, while the physiological or psychophysical basis for this phenomenon are not presently clearly understood, it may be possible that the different intensities of sound have different efficacy as distracting stimuli in distracting the attention of the tested subject from the visual stimuli presented in the test. It may therefore be concluded that sounds having graded intensity values may be used for assessing or quantifying the severity of retinal or choroidal lesions or abnormalities.

Figure 16:
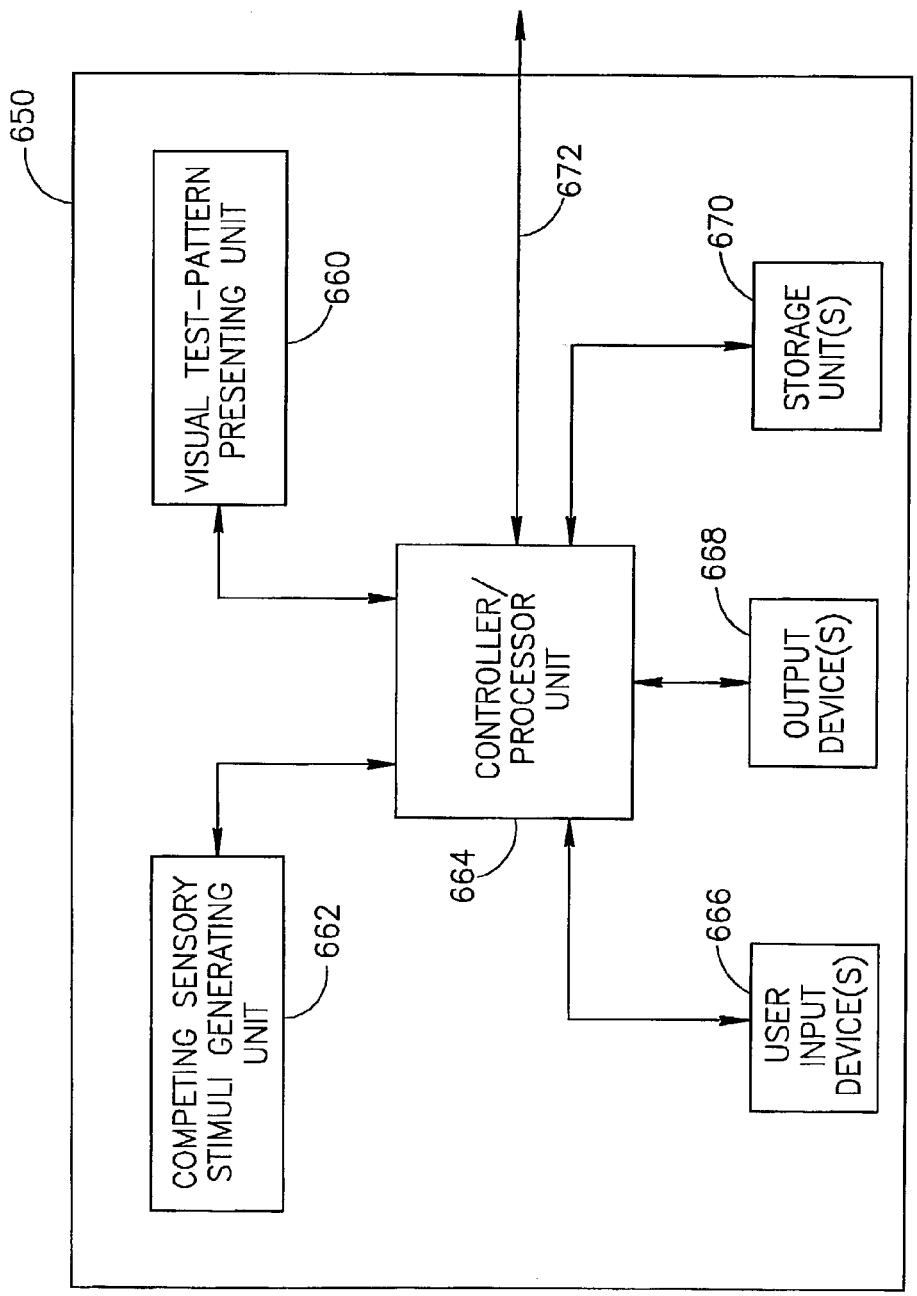
FIG. 16 is a schematic block diagram illustrating a system for applying visual tests and competing sensory stimuli to a test subject, in accordance with an embodiment of the present invention.

Reference is now made to FIG. 16 which is a schematic block diagram illustrating a system for applying visual tests and competing sensory stimuli to a test subject, in accordance with an embodiment of the present invention.

The system 650 may include a visual test pattern presenting unit 660 for presenting test patterns to a test subject (not shown), and a competing sensory stimuli generating unit 662 for presenting the tested subject competing sensory stimuli. The visual test-pattern presenting unit 660 and the competing sensory stimulus generating unit 662 may be suitably operatively coupled to a controller/processor unit 664. The controller/processor unit 664 may control and coordinate the presenting of visual and competing sensory stimuli to the test subject by the visual test-pattern presenting unit 660 and the competing sensory stimuli generating unit 662, respectively.

The system 650 may further include one or more user input device(s) 666, one or more output device(s) 668 and a storage unit 670 for storing data. The user input device(s) 666, the output device(s) 668, and the storage unit 670 may be suitably connected to the controller/processor unit 664.

The visual test-pattern presenting unit 660 may be any type of unit or device suitable for presenting visual test patterns to a test subject as disclosed hereinabove and as known in the art. For example, the visual test-pattern presenting unit 660 may be a computer with a coupled display device, such as a computer, or a desktop computer or a laptop computer or a workstation or any other device known in the art that is capable of controllably presenting test patterns to a test subject. For example, the visual test-pattern presenting unit 660 may be any of the systems 105 of FIG. 1 or the system 600 of FIG. 10, or any other type of display or screen based device known in the art, or any other type of device capable of scanning a beam of light into an eye, including, but not limited to, SLO devices and head up display (HUD) devices known in the art.

If the visual test-pattern presenting unit 660 includes a surface or a screen capable of displaying images of the test patterns (and fixation target, if required), the display may be any type of suitable display known in the art, including but not limited to a cathode ray tube (CRT) type display device, a liquid crystal display (LCD), a light emitting diode (LED) or organic light emitting diode (OLED) based display device, a plasma display device, a mechanical or micro-electromechanical (MEMS) based display device, or the like. Generally, any suitable device that may be adapted for displaying or projecting images on a surface or directly projecting images into an eye, or of controllably scanning a beam of light into an eye is considered to be within the scope of the present invention.

Generally, the competing sensory stimulus generating unit 662 may be any type of device or system or unit which is capable of delivering sensory stimuli to the individual which is being tested using the system 650.

For example, in accordance with one possible embodiment of the invention, the competing sensory stimulus generating unit 662 may be a system or device for delivering auditory stimuli (sound stimuli) to the tested individual, such as but not limited to a sound source suitably coupled to controller/processor unit 664. In the exemplary embodiment disclosed in detail hereinabove and illustrated in FIG. 15, the competing sensory stimulus generating unit 662 may include a computer add-on sound card (not shown in FIG. 15) installed in the computer 110 and coupled to the pair of headphones 211. It will be appreciated by those skilled in the art, that many other types of sound sources may be used as is disclosed in detail hereinabove or as is known in the art. Thus, any suitable type of sound source which may be used to generate sound stimuli in a controlled manner may be used in the present invention.

In accordance with other possible embodiments of the present invention, the competing sensory stimulus generating unit 662 may be any suitable device for delivering tactile sensory stimuli, or any suitable device for delivering other types of somatosensory stimuli capable of competing with the visual stimuli delivered by the system 650 to the tested individual, such as, but not limited to, nociceptive stimuli, tactile stimuli, thermal stimuli (temperature change related stimuli), pressure stimuli, mechanical stimuli delivered to the tested individual (such as, but not limited to, mechanically delivered vibrations applied to the skin of the tested individual), or any other suitable stimuli having other suitable sensory modalities.

For example, in accordance with one possible embodiment of the invention, the competing sensory stimulus generating unit 662 may include an electrically powered vibrator (not shown) or probe which is mechanically coupled or attached or put in contact with the skin of the tested individual and which is suitably connected to the controller/processor unit 664. For example, the vibrator may be a small flat piezoelectric transducer which put in contact with the skin of the tested individual is attached to the skin (of the finger, or the hand, or any other suitable body part of the tested individual) using a band or strap of flexible material (not shown). In operation, vibrations having different vibration amplitudes or frequencies may be delivered to the skin of the tested individual before, during or after the presentation of the test patterns as disclosed hereinabove. Many other types of vibrating devices or probes or other graded mechanical stimulus delivering devices may also be adapted for used with the present invention, as is well known in the art.

In accordance with another possible embodiment of the invention, the competing sensory stimulus generating unit 662 may be an electrically operated heating element, or Peltier device, (not shown in detail) which may thermally coupled to the skin and which may be used to controllably deliver heat or cold stimuli to the skin of the tested individual before, during or after the presentation of the test patterns as disclosed hereinabove. Additionally, a suitable laser device may be used to deliver heating pulses having different graded parameters to an area of the skin of the tested individual which may be used as thermal competing stimuli.

In accordance with another possible embodiment of the invention, the competing sensory stimulus generating unit 662 may be an electrically operated heating element, or Peltier device (not shown in detail) which may thermally coupled to the skin and which may be used to controllably deliver thermal (heat or coldness) stimuli to the skin of the tested individual before, during or after the presentation of the test patterns as disclosed hereinabove.

It is noted that the methods and devices for delivering various graded or non-graded) sensory stimuli to a patient or test subject are well known in the art, are not the subject matter of the present invention, and are therefore not disclosed in detail hereinafter. Generally, the competing stimuli (CS) of the method and systems of the present invention may be delivered to the test subject using any suitable device known in the art for controllably delivering such sensory stimulation to a tested individual.

The user input device(s) 666 may be one or more user interface devices which may be used by the tested individual to provide input to or to interact with the system 650 during the performing of tests. The input device(s) 666 may include but are not limited to, a computer pointing device, a mouse, a keypad, a keyboard, a touch sensitive screen (usable in conjunction with a suitable stylus or with a finger, or the like), a touch sensitive pad, other types of touch sensitive devices, a light pen, a stylus, a joystick, and any suitable combination of the above listed input devices, or any other suitable type of input device known in the art.

The output device(s) 668 may include but are not limited to a display device for providing instructions or images, or test patterns to the tested individual, a printer for providing hardcopy of the test results or of test schedules or of patient demographic or other data (including, but not limited to, raw test results, and/or processed test results, and or diagnostic information, in graphic form or alphanumeric form or any other symbolic form).

The storage unit(s) 670 of the system 650 may be any suitable type of storage known in the art and usable for storing data and/or programs for operating the system 650 or the controller/processor unit 664, and or raw or processed test results and the like. For example, the storage unit(s) 670, may include one or more solid state memory devices such as, but not limited to, RAM, DRAM, SDRAM ROM, RDRAM, FLASH, and compact FLASH memory devices, or combinations thereof. The storage unit(s) 670 may also include other types of storage devices having fixed or removable storage media, such as, but not limited to, magnetic drives, optical drives, magnet-optical drives, solid state drives having fixed or removable solid state media, holographic drives or storage devices, or the like.

It is noted that while the system 650 is shown is a specific configuration illustrated in FIG. 16, many other configurations thereof may be implemented. For example, while the controller/processor unit 664 of FIG. 16 is illustrated as a separate unit, the controller/processor unit 664 may be included as part of the visual test-pattern presenting unit 660 or of the visual test-pattern presenting unit 660. In other embodiments of the system 650, the visual test-pattern presenting unit 660 and/or the visual test-pattern presenting unit 660 may include additional controllers and/or processors (not shown in detail in FIG. 16). Furthermore, the system 650 may be (optionally) suitably connected via one or more communication line(s) 672 to other computers (not shown) or to a computer network such any of the networks disclosed hereinabove (including but not limited to, a LAN, a PAN, a WAN, a VPN or the like).

Thus, while in accordance with one embodiment of the present invention, the system 650 or the other systems disclosed in the application, may be a standalone system, such as a system which may be used in the office of an eye physician or in a clinic of an ophtalmologist or other eye specialist, for testing individuals, for patient screening, or for other diagnostic or treatment follow-up purposes, or for any other suitable. In this embodiment the testing and processing of the data, and the reporting of the test results may all be performed by the system.

In accordance with other embodiments of the invention, the systems 650, or 105 may be a simple and relatively inexpensive system for home use by the patient. In such embodiments it may be possible to process the data by the system and produce an output for the patient as disclosed in detail hereinabove, or it may be possible to send the processed test results or the raw data itself using any the network types disclosed hereinabove. The analyzed test results or the raw data (or both) may be communicated to a supervising physician's office or clinic or to a central data bank in a hospital or in an or to any other suitable health service provider, or the like.

Additional Possible Types of Competing Stimuli

An additional type of usable competing stimulus is a visual stimulus. In accordance with another embodiment of the invention, a visual test pattern is presented to the patient (such as but not limited to the segmented test patterns disclosed in EXPERIMENT 1 and EXPERIMENT 2 using the flash method of presenting the test pattern, as disclosed in detail hereinabove) and another visual stimulus is displayed on the same display device at a different location than the location of the test pattern. For example, the additional (distracting or competing) visual stimulus may be a visual pattern such as but not limited to a known symbol or character or the like such as for example, the letter C, or the number 5, or a graphic symbol (such as, for example, the symbol ☺), or any other suitable visual pattern or alphanumeric symbol or character or graphic sign, or the like. This additional visual stimulus is referred to as a "distracting visual stimulus" (DVS) hereinafter.

In accordance with another embodiment of the present invention, the DVS may be superimposed on part of the test pattern or may be separately presented on the display device. The DVS may or may not be presented synchronously with the test pattern. For example, if the test pattern is presented using the above described flash method, the DVS may be flashed together with the test pattern for the entire duration of the presentation of the test pattern, or may be presented before, and/or during, and/or after the presentation of the test pattern. Thus, the duration of the presentation of the DVS may be equal to, or smaller than, or larger than the duration of the presented test pattern.

In accordance with another embodiment of the present invention, the time period of the presentation of the test pattern may fully or partially overlap the time period of the duration of the DVS. The time period of the presentation of the DVS may, however, not overlap the duration of presentation of the test pattern, but may precede the time of presentation of the test pattern and may terminate before or simultaneously with the beginning of the presentation of the test pattern.

In accordance with another embodiment of the present invention, the DVS may also be any other type of visual pattern such as a picture or digital photograph or digital representation, or image of a human face, or any other suitable object. The distracting capability of the DVS may be related to the type or nature of the object presented in the DVS.

In accordance with another embodiment of the present invention, the DVS may be a part of the test pattern. For example, if the test pattern is a segmented test pattern (such as but not limited to the test pattern 382 of FIG. 5B), the DVS may include one or more of the segments of the segmented test pattern 382.

In a non-limiting example, the DVS may be one or more segments of the test pattern 382 which may be colored yellow, while all the rest of the segments of the test pattern 630 may be colored white (all the segments of the test pattern 682 may be presented on a black background). Thus, the different color of the segments which are included in the DVS may distract the attention of the patient or compete for attention with a PROD which may be observed by the patient when the test pattern 382 is presented at a location on the screen 112 such that at least part of the test pattern is projected on a retinal lesion. Similar to the results of the competition of the ADs introduced into the test pattern in EXPERIMENT 1 and EXPERIMENT 2, the presentation of this type of DVS (comprising yellow colored segments) may decrease the probability that the patient will report the PROD.

It is noted that while the exemplary embodiment disclosed hereinabove uses segmented lines, the use of different colored DVS may also be applied to any other type of usable test pattern, such as but not limited to continuous lines (including straight or curved lines), or any other suitable type of test pattern. For example, if the test pattern is a straight continuous line, the DVS may be a differently colored portion of the straight line.

In accordance with another embodiment of the present invention, the part of the test pattern the DVS may only partially overlap the test pattern. For example, if the test pattern used is similar to the test pattern 382 of FIG. 5B, the DVS may be a short segmented line (not shown) which is generally orthogonal to the test pattern 382 and has six yellow segments. One segment of the DVS may overlap one segment of the test pattern 382 such that the segment which is common to the DVS and the test pattern is yellow.

It is noted that the color yellow is arbitrarily chosen as a non-limiting example and that any other suitable color may be used in other embodiment of the invention.

Reference is now made to FIGS. 17A–17K which are schematic diagrams illustrating exemplary forms of various different test patterns and competing visual stimuli which may be used in accordance with some embodiments of the present invention.

Each of FIGS. 17A–17K illustrates a test pattern and a competing visual stimulus which may be used as a DVS as they may appear on part of the screen 112 of the system 105 of FIG. 1 or as may be projected on an area of interest of a tested retina. For the sake of clarity of illustration, the fixation target is not shown in FIGS. 17A–17K, but may be any type of suitable fixation target as disclosed and illustrated in detail hereinabove.

Figure 17A:
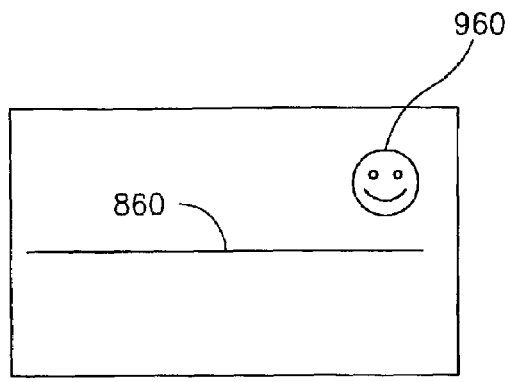
FIGS. 17A–17K are a schematic diagrams illustrating exemplary forms of various different test patterns and competing visual stimuli which may be used in accordance with some embodiments of the present invention.

In the example illustrated FIG. 17A, the test pattern is a horizontal straight line 860 and the competing visual stimulus used as a DVS is a graphic symbol 960 schematically resembling a human face.

Figure 17B:
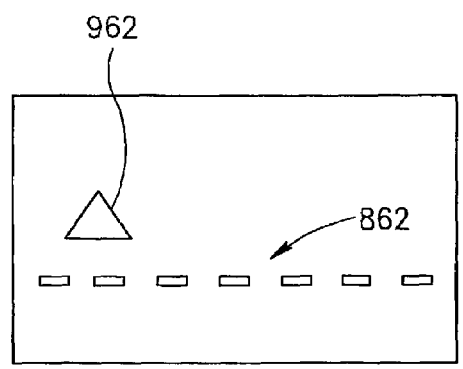

In the example illustrated FIG. 17B, the test pattern is a horizontal segmented straight line 862 and the competing visual stimulus used as a DVS is a triangular pattern 962.

Figure 17C:
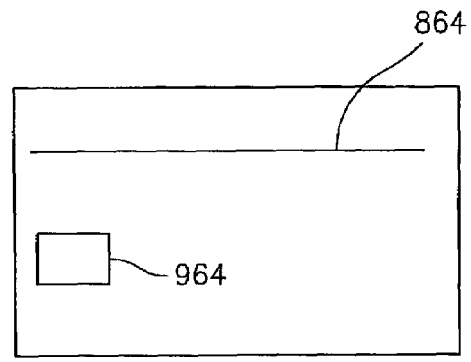

In the example illustrated FIG. 17C, the test pattern is a horizontal straight line 864 and the competing visual stimulus used as a DVS is a rectangular pattern 964.

Figure 17D:
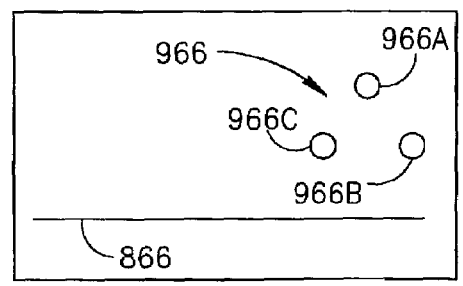

In the example illustrated FIG. 17D, the test pattern is a horizontal straight line 866 and the competing visual stimulus used as a DVS includes three dots 966A, 966B, and 966C arranged in a triangular pattern 966.

Figure 17E:
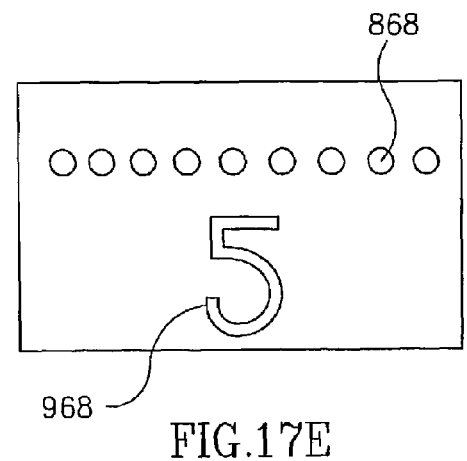

In the example illustrated FIG. 17E, the test pattern is a straight horizontal dotted line 868 and the competing visual stimulus used as a DVS is a pattern 968 shaped as the numeral "5".

Figure 17F:
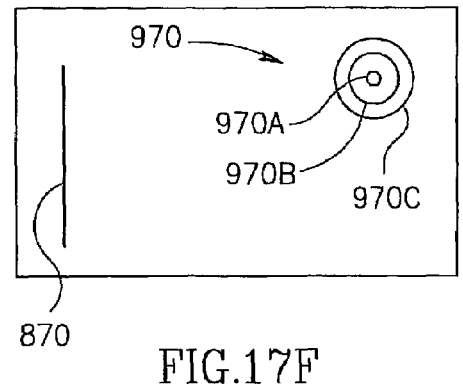

In the example illustrated FIG. 17F, the test pattern is a vertical straight line and the competing visual stimulus used as a DVS is a pattern 970 comprising three concentric rings 970A, 970B, and 970C.

Figure 17G:
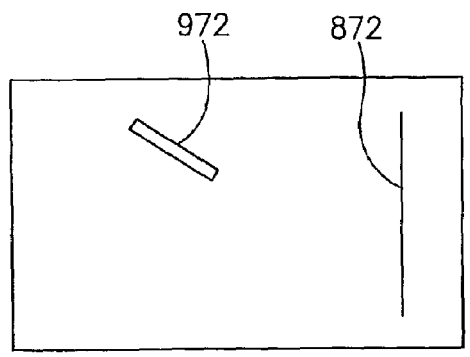

In the example illustrated FIG. 17G, the test pattern is a vertical straight line and the competing visual stimulus used as a DVS is a slanted short line 972 which is inclined at an angle to the vertical line 872.

Figure 17H:
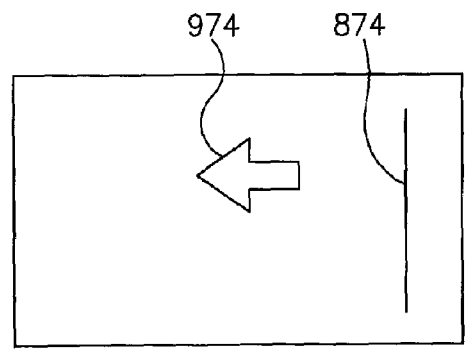

In the example illustrated FIG. 17H, the test pattern is a vertical straight line 874 and the competing visual stimulus used as a DVS is an arrow-like pattern 974.

Figure 17I:
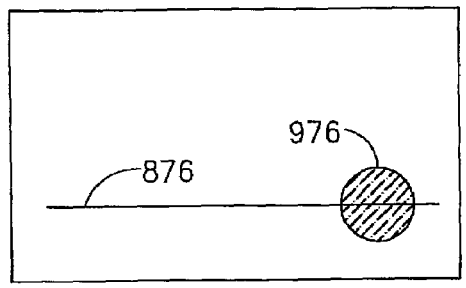

In the example illustrated FIG. 17I, the test pattern is a horizontal straight line 876 and the competing visual stimulus used as a DVS is a circular pattern 976 which is superimposed on the line 876.

Figure 17J:
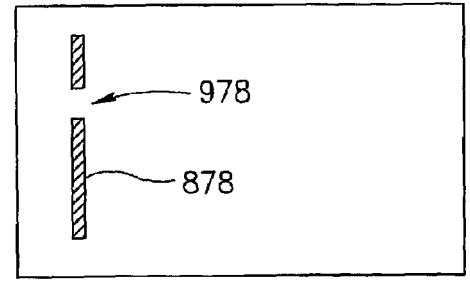

In the example illustrated FIG. 17J, the test pattern is a vertical straight line 878 and the competing visual stimulus used as a DVS comprises a gap 978 (a missing part) in the line 878.

Figure 17K:
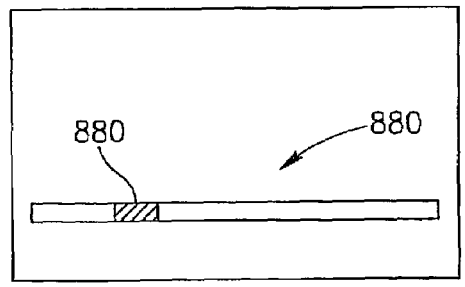

In the example illustrated FIG. 17K, the test pattern is a horizontal_straight line 880 and the competing visual stimulus used as a DVS comprises a part 880A of the line 880. The part 880A may have a color which is different than the color of the remaining parts of the line 880. Alternatively, the part 880A may have another visually perceivable characteristic, such as brightness, luminance, or the like, which is different than the same characteristic of the remaining parts of the line 880.

In performing the tests, the test patterns may be projected at different locations on the tested retina, using any of the test methods disclosed hereinabove (including, but not limited to the "flash" and the "moving line" methods). The visual patterns which are being used as competing visual stimuli or DVS may be projected on the retina before, during, or after the presentation of the test patterns as disclosed in detail hereinabove. In different repetitions one or more characteristics or parameters of the_competing visual stimulus may be varied in order to change it's efficacy as a competing or distracting stimulus.

For example one or more characteristic of the competing stimulus may be changed, including, but not limited to, the size, the color, the brightness, the hue, or the distance of the DVS from the test pattern may be varied. In specific forms of competing stimuli some types of characteristics may be changed. For example, for the competing stimulus 966 of FIG. 17D, the distance between the dots 966A, 966B, and 966C may be increased or decreased, but many other different types of changes may be made to change the competing efficacy or distracting efficacy of the competing stimulus or DVS.

Generally, the types and spatial arrangement of the test patterns and the competing visual stimuli, and the changing of the parameters or characteristics of the competing visual stimulus may be empirically determined by performing suitable clinical studies to test the efficacy of various different forms of visual (or other) competing stimuli (graded or non-graded) as competing stimuli. Such tests may be performed on test subjects having normal healthy retinas, by using ADs inserted into the test patterns and empirically assessing the competing efficacy of the competing stimuli as disclosed hereinabove. Alternatively or additionally, the tests may be performed on patients clinically diagnosed to have certain stages of AMD and various degrees of retinal or choroidal lesions.

It is also noted that the different competing stimuli used within a test need not be quantitatively graded. Turning briefly to FIG. 17C, while changing the size of the rectangular pattern 964 may suitably change it's efficacy as a competing stimulus or DVS, it may also be possible to use competing stimuli having qualitative differences in the test. For example it may be possible to use a red rectangular competing stimulus of a first size and a yellow rectangular competing stimulus having a second different size as competing visual stimuli within the same test, provided one pattern having a specific combination of characteristics is empirically determined to have a competing efficacy or distracting efficacy which is different than another of the used competing stimuli having a different combination of characteristics.

It is noted that because the efficacy of different competing visual stimuli may differ significantly, it may be also possible to mix different types of stimuli in the same test. For example in accordance with one possible embodiment of the invention, it may be possible to use the graphic symbol 960 (FIG. 17A, the rectangular pattern 964 (FIG. 17C) and the arrow-like pattern 974 (FIG. 17H) in the same test depending on their efficacy as competing visual stimuli or distracting stimuli. Thus, such combinations of different competing stimuli may be used to assess the degree, or size, or severity of a retinal or choroidal lesion or abnormality, based on their empirically tested efficacy.

It is noted that many possible variations and permutations of the DVS of the present invention are possible which are included within the scope of the present invention. A few non-limiting examples may include, but are not limited to, DVS which comprise one or more blinking segments of the test pattern, or one or more blinking portions of a continuous test pattern, or any other visual patterns or images which may or may not partially overlap the test pattern and which may have different colors than the test pattern, or a gray level, or a luminosity, or brightness which is different than the gray level, or the luminosity, or the brightness of the test pattern, respectively, or any suitable combinations of the above differences.

It will be appreciated by those skilled in the art that combinations of the above properties of the DVS may also be possible. For example, the DVS may include one or more segments of the test pattern which may have a different color than the color of the remaining segments of the test patterns and may also blink (turn on and off at a desired frequency).

Thus, DVS types usable in the present invention are not limited to the exemplary embodiments described herein but may be any suitable type of visual stimulus which is effective in affecting the probability that the patient will report a PROD when a test pattern is presented to the patient at a location such that the image of the test pattern is projected on a lesioned retinal (or choroidal) region.

By repeating the presentation of the test pattern and the DVS, varying (grading) one or more of the parameters or characteristics of the DVS, and recording the patient's responses to the presentation of the test stimuli it may be possible to analyze the competition of the DVS with the PROD and to empirically determine classification criteria for various AMD stages, or for other stages of other different retinal pathologies or diseases.

The parameters of the DVS that may be varied (or graded) in different presentations of test patterns may be, but are not limited to, one or more of the color (or colors) of the DVS, the brightness of the DVS (the absolute DVS brightness or the brightness of the DVS relative to the brightness of the test pattern), the luminosity of the DVS, the gray level of the DVS, the frequency of blinking of the DVS, the size or dimensions or shape of the DVS, the distance of the DVS from the test pattern, the inclination of the DVS relative to the test pattern, or combinations thereof. Additionally, it may be possible to use a group of different DVS types which are empirically selected on the basis of having different psychophysical efficacy as distracting stimuli.

Another lesion grading method may be implemented, in accordance with another embodiment of the present invention by introducing a controlled degree of "visual noise" into the test. For example, while the background on which the test patterns are presented may be a uniform black background, the background may also be a variable background. For example, one or more of the visual parameters the individual pixels (or of pixel groups) on the screen 112 which form the background for the test pattern may be varied randomly, or pseudo-randomly, or periodically, or a periodically. The pixel parameters which may be varied may include, but are not limited to, the intensity, color, luminosity, gray level, hue (for pixel groups or single composite pixels), and the like.

The "visual noisiness" of the background may be varied between different presentations of test patterns, thus, effectively allowing graded degrees of visual noise which may have different efficacy in changing the probability that the patient will report a PROD when a test pattern is presented to the patient on the noisy background at a location such that the image of the test pattern is projected on a lesioned retinal region.

Such graded degrees of background visual noise may be implemented, inter alia, by changing the frequency of the variation of the pixel or pixel group parameters, by changing the range of pixel parameter values between which the pixels are allowed to vary (for example, by increasing or decreasing the range of values within which the pixels' brightness, or the pixels' color, or the pixels' gray level is allowed to vary), or by modifying the number and/or the distribution of the background pixels that are varied (such as, for example, by changing the percentage of background pixels for which one or more visually detectable parameters are allowed to vary, or by suitably changing or modifying the values of other suitable parameters in a way which may affect the characteristics of the background noise).

Thus, the noisy background types usable in the present invention are not limited to the exemplary embodiments described herein but may be any suitable type of visual background variation or degree which is effective in affecting the probability that the patient will report a PROD when a test pattern is presented to the patient at a location (on the noisy background) such that the image of the test pattern is projected on a lesioned retinal region.

By repeating the presentation of the test pattern, while varying (grading) one or more of the parameters of the background, and recording the patient's responses to the presentation of the test stimuli on different backgrounds it may be possible to analyze the competition of the noisy background with the PROD and to empirically determine classification criteria for various AMD stages, or for other stages of other different retinal pathologies or diseases.

It is noted that generally it may be possible to subject the tested individual to a competing sensory stimulus (of any experimentally effective sensory modality) before, or during, or after the presentation of the test pattern to the tested individual, or before and during the presentation of the test pattern to the tested individual, or during and after the presentation of the test pattern to the tested individual, or before and during and after the presentation of the test pattern to the tested individual. The selection of the timing and duration of the presentation of the CS may be determined, inter alia, by the type and sensory modality of the CS, the method of presentation of the test pattern, the type and duration of the test patterns, and other practical considerations. It will be appreciated that the specific timing and duration parameters of the competing auditory stimuli of EXPERIMENT 3 and EXPERIMENT 4 above are given by way of example only and many other variations of the timing and duration of the auditory competing stimulus or of any other types of auditory, or visual competing stimuli or other sensory modality of competing sensory stimuli may be used in various implementations of the method of the present invention.

It is noted that while the experiments disclosed herein demonstrate the use of competing stimuli having graded stimulus parameter(s), the invention is not limited to the use of competing stimuli which are graded. The experiments with auditory competing stimuli disclosed herein demonstrate that while grading the sound intensity may be used to vary the competing efficacy of the CS, other non-graded changes in the stimulus may be effectively used to vary the competing efficacy of the CS (such as, but not limited to differences the spectral content of the sound). Moreover, in accordance with yet another embodiment of the present invention, it may be possible to used competing stimuli having different sensory modalities in the same test.

For example, it may be possible to perform the testing of the present invention by using within the same test visual competing stimuli and auditory competing stimuli. In a non limiting example, the system 305 of FIG. 15 may be used to deliver auditory competing stimuli (as disclosed in detail hereinabove to the tested individual 100 together with some of the repetitions of the displaying of the test patterns (such as, but not limited to, the segmented straight line test patterns disclosed hereinabove and illustrated in FIGS. 3, 5B, and 5E) while in some other repetitions of the displaying of the test patterns of the same test, the test patterns may include visual competing stimuli, such as, but not limited to, artificial distortions (such as for example any of the artificial distortions shown in FIG. 5J, or partially shown in FIG. 6, or the like) or, alternatively, the test patterns may be presented together with other competing visual stimuli (such as but not limited to, any of the DVS or competing visual stimuli disclosed herein and illustrated in the examples of FIGS. 17A–17K, or the like). Since each of the different competing stimuli (including but not limited to, any type of AD or DVS and auditory competing used within the same test) may have a different competing efficacy, it is possible to empirically determine the specific efficacies of such competing stimuli in experiments in known clinically diagnosed patient groups and to establish suitable diagnostic criteria for use in screening or testing patients as disclosed in detail hereinabove for experiments using graded artificial distortions only.

In an exemplary mixed modality test one may use two repetitions of a presentation of a straight segmented line together with exposing the tested individual to sound type 2 (as disclosed in detail in EXPERIMENT 4 above) and two repetition of presenting an artificially distorted test pattern (such as, but not limited to, the artificial distortion having a height of 0.19° of EXPERIMENT 1 above) at each tested retinal location. When using competing stimuli of different sensory modalities within the same test, the criteria for establishing the clinical stage of AMD (or of other types of eye disease) by empirically determining the diagnostic criteria in experiments using known clinically diagnosed patient groups, as disclosed in detail hereinabove in EXPERIMENT 1.

The determination of suitable diagnostic criteria (for assessing the clinical stage of AMD in patients or for determining the stages of other types of eye disease) using single sensory modality competing stimuli or mixed sensory modality competing stimuli within the same test may be implemented by those skilled in the art based on the specific examples in the experiments disclosed and the general principles and methods of competition of stimuli as disclosed herein.

It is further noted that the methods, systems and devices of the present invention may be used to detect and assess retinal and choroidal lesions which cause vision abnormalities in the eye. While the devices methods and systems disclosed hereinabove and illustrated in the drawings have been adapted for detecting and assessing the presence and/or clinical stages of AMD, the devices methods and systems disclosed may also be used or adapted for detecting or assessing other types of vision abnormalities or eye diseases. For example the following types of eye diseases or retinal or choroidal pathologies may be detected or assessed or diagnosed by suitable adaptation and/or modifications of the methods devices and systems of the present invention, ocular hystoplasmosis, myopia, central serous retinopathy, central serous choroidopathy, glaucoma, diabetic retinopathy, media opacities (such as, but not limited to, cataract), retinitis pigmentosa, optic neuritis, epiretinal membrane, vascular abnormalities and/or occlusions, choroidal dystrophies, retinal dystrophies, macular hole, choroidal or retinal degeneration, lens abnormalities, and the like.

It will be appreciated that the preferred embodiments disclosed hereinabove and illustrated in the drawings are given by way of example only and that many variations, permutations and modifications of the present invention may be made which are within the scope and spirit of the present invention.

The invention claimed is:

1. A method for obtaining data on the vision of an individual, comprising:
   presenting, for a first duration, a test pattern to the individual, to allow the individual to form a perceived image of said test pattern;
   receiving from said individual, input indicative of a difference between said perceived image and the test pattern, if said individual perceived a difference,
   the presenting and receiving being repeated one or more times, wherein for at least one of the repetitions said individual is subjected to a competing sensory stimulus; and
   analyzing the received input to determine information on the vision of said individual,
   wherein the analysis is at least partially responsive to one or more characteristics of said competing sensory stimulus.

2. A method according to claim 1, wherein said first duration is in the range of 100–160 milliseconds.

3. A method according to claim 1, wherein analyzing the received input comprises analyzing to determine whether the individual has an eye disease.

4. A method according to claim 3, wherein said eye disease is selected from the group consisting of age-related macular degeneration, choroidal neovascularization, ocular histoplasmosis, myopia, central serous retinopathy, central serous choroidopathy, glaucoma, diabetic retinopathy, media opacities, cataract, retinitis pigmentosa, optic neuritis, epiretinal membrane, vascular abnormalities, vascular occlusions, choroidal dystrophies, retinal dystrophies, macular hole, choroidal degeneration, retinal degeneration, lens abnormalities, and combinations thereof.

5. A method according to claim 1, wherein analyzing the received input comprises determining if said individual belongs to a group having a defined clinical stage of an eye disease.

6. A method according to claim 1, wherein the analysis is at least partially responsive to the magnitude of the competing sensory stimulus.

7. A method according to claim 1, wherein the analysis is at least partially responsive to the position and/or orientation of the test pattern.

8. A method according to claim 1, wherein the analysis is at least partially responsive to patient indications of locations within the patterns of the differences between the perceived image and the test pattern.

9. A method according to claim 1, wherein the competing stimulus in at least one of the repetitions is presented only before the presenting of the test pattern.

10. A method according to claim 1, wherein the competing stimulus in at least one of the repetitions is presented only during at least part of the first duration.

11. A method according to claim 1, wherein the competing stimulus in at least one of the repetitions is presented after at least part of the first duration.

12. A method according to claim 1, wherein the individual is subjected to the competing sensory stimulus during a period substantially coinciding with the first duration.

13. A method according to claim 1, wherein at least one of the competing stimuli comprises a stimulus that changes over the time in which the individual is subjected to the stimulus.

14. A method according to claim 1, wherein the competing stimulus comprises an auditory stimulus.

15. A method according to claim 1, wherein the competing stimulus comprises a visual stimulus.

16. A method according to claim 1, wherein the competing stimulus comprises a tactile stimulus.

17. A method according to claim 1, wherein the competing stimulus comprises a nociceptive or a somatosensory stimulus.

18. A method according to claim 1, wherein the competing stimulus is not a distortion of the test pattern.

19. A method according to claim 1, wherein the competing stimulus is different for at least some of the repetitions.

20. A method according to claim 19, wherein the competing stimulus of different repetitions has different durations or different beginning times relative to the first duration.

21. A method according to claim 19, wherein the competing stimulus of different repetitions has a different magnitude.

22. A method according to claim 19, wherein the competing stimulus is a visual competing stimulus and wherein the competing stimulus of different repetitions has a different shape, pattern, color, or intensity.

23. A method according to claim 1, wherein said competing stimulus is not a part of the test pattern.

24. A method according to claim 1, wherein said competing stimulus is a noisy visual background of the test pattern.

25. A method according to claim 1, wherein said competing stimulus is within the test pattern.

26. A method according to claim 25, wherein said competing stimulus comprises an artificial distortion which mimics the appearance of a distortion perceived by an individual when the test pattern is presented at a location of the retina of the individual which comprises an abnormality.

27. A method according to claim 25, wherein at least one of the inputs of the individual are analyzed to determine a probability that the input is due to the competing stimulus.

28. A method according to claim 25, wherein the indications are given a weight for use in the analysis responsive to a distance between the indications and the competing stimulus.

29. A method according to claim 1, comprising fixating the individual's vision at or about a fixation target before presenting the test pattern.

30. A method according to claim 1, wherein receiving input indicative of a difference between the perceived image and the test pattern comprises receiving input on a temporary distortion of the test pattern.

31. A method according to claim 1, wherein receiving input indicative of a difference between the perceived image and the test pattern comprises receiving input on perceived relative motion in the test pattern.

32. A method according to claim 1, wherein receiving input indicative of a difference between the perceived image and the test pattern comprises receiving input on a misaligned segment in the perceived image of the test pattern.

33. A method according to claim 1, wherein receiving input indicative of a difference between the perceived image and the test pattern comprises receiving input on a blurring of the perceived image relative to the test pattern.

34. A method according to claim 1, wherein the test pattern is presented at different locations in at least some of the repetitions.

35. A method according to claim 34, wherein the different locations of the test pattern map a selected region of a patient's retina at a desired resolution.

36. A method according to claim 1, wherein the test pattern is presented with different orientations in at least some of the repetitions.

37. A method according to claim 1, wherein said test pattern is a straight line or a segmented straight line.

38. A method according to claim 1, wherein presenting the test pattern comprises displaying on a display device or projecting with a beam scanning device.

39. A method according to claim 1, wherein said first duration is in the range of 10 milliseconds to 20 seconds.

40. A method according to claim 19, wherein at least some of the competing stimuli of different repetitions have at least one stimulus parameter having a different value than the value of the same parameter of other stimuli, said at least one stimulus parameter is selected from the competing stimulus duration, the competing stimulus beginning time point relative to the first duration, the competing stimulus ending time point relative to the first duration, and combinations thereof.

41. A method according to claim 37, wherein said competing stimulus is selected from a competing stimulus comprising at least one segment of said segmented line being displaced relative to said segmented line, and a competing stimulus comprising at least one portion of said segmented line being displaced relative to said straight line.

42. A method according to claim 37, wherein said competing stimulus is selected from a competing stimulus comprising at least one segment of said segmented line being absent, a competing stimulus comprising at least one portion of said segmented line being absent, a competing stimulus comprising at least one segment of said segmented line being blurred and a competing stimulus comprising at least one portion of said segmented line being blurred.

43. A method for obtaining data on an eye in an individual, comprising:
    presenting for a first duration a test pattern to the individual, to allow the individual to form a perceived image of said test pattern;
    receiving from said individual, input indicative of a difference between said perceived image and the test pattern, if said individual perceived a difference; and
    the presenting and receiving being repeated one or more times, wherein for at least one of the repetitions said individual is subjected to a predetermined visual competing sensory stimulus, within the test pattern; and
    analyzing the received input to determine information on an eye of said individual.

44. A method according to claim 43, wherein the competing stimulus of different repetitions have different magnitudes.

45. A method according to claim 44, wherein the analysis is at least partially responsive to the magnitude of the competing sensory stimulus.

46. A method according to claim 43, wherein said first duration is in the range of 100–160 milliseconds.

47. A method according to claim 43, wherein said first duration is in the range of 10 milliseconds to 20 seconds.

48. Apparatus for eye analysis, comprising:
    a pattern presenting unit;
    an input device operative to receive input from an individual; and
    a processing unit adapted to generate one or more patterns to be presented sequentially to the individual through the pattern presenting unit, to generate a competing stimulus to which the individual is subjected with relation to at least one of the test patterns, to receive, through the input device, input indications representing, for at least one of the test patterns, a difference observed by said individual between a perceived image of the test pattern and the test pattern, and to analyze the received input indications to determine information on the vision of the individual.

49. Apparatus according to claim 48, wherein the processing unit is adapted to analyze the input indications at least partially responsive to one or more characteristics of the competing stimulus corresponding to one or more of the test patterns.

50. Apparatus according to claim 49, wherein the processing unit is adapted to analyze the input indications at least partially responsive to a magnitude of the competing stimulus corresponding to one or more of the test patterns.

51. Apparatus according to claim 48, wherein the processing unit is adapted to generate for each of a plurality of the presented patterns, a competing stimulus with a magnitude level, the magnitude levels of at least two of the competing stimulus being different from each other.

52. Apparatus according to claim 48, wherein the processing unit is adapted to provide an indication on whether the individual has an eye disease.

53. Apparatus according to claim 48, wherein the processing unit is adapted to provide an indication on whether the individual belongs to a group having a defined clinical stage of an eye disease.

54. Apparatus according to claim 48, wherein processing unit is adapted to receive indications of locations within the patterns of the differences between the perceived image and the test pattern.

55. Apparatus according to claim 48, wherein the generated competing stimuli are presented to the patient through the pattern presenting unit.

56. Apparatus according to claim 55, wherein the processing unit is adapted to assign the input indications weights responsive to a distance between the indications and the competing stimuli.

57. Apparatus according to claim 55, wherein at least one of the competing sensory stimuli comprises a bluffing of a segment of the test pattern.

58. Apparatus according to claim 55, wherein at least one of the competing sensory stimuli comprises a change in the shape of the test pattern.

59. Apparatus according to claim 48, comprising a speaker and wherein the competing stimuli are provided to the individual through the speaker.

60. Apparatus according to claim 48, wherein the competing stimulus with relation to at least one of the test patterns is provided to the individual at least partially before or after the test pattern is presented.

61. Apparatus according to claim 48, wherein the processing unit analyzes at least one of the inputs of the individual to determine a probability that the input is due to a competing stimulus.

62. Apparatus according to claim 48, wherein the processing unit is adapted to generate at least some of the one or more patterns to be presented sequentially, in different locations on the eye of the individual.

63. Apparatus according to claim 48, comprising a competing stimuli generating unit adapted to provide the individual with tactile stimuli.

64. Apparatus according to claim 48, wherein the pattern presenting unit comprises a display device or a beam scanning device.

* * * * *